United States Patent
Matsumoto et al.

(10) Patent No.: US 6,596,445 B1
(45) Date of Patent: Jul. 22, 2003

(54) O-ACYLOXIME PHOTOINITIATORS

(75) Inventors: Akira Matsumoto, Kyoto (JP); Hidetaka Oka, Hyogo (JP); Masaki Ohwa, Kobe (JP); Hisatoshi Kura, Hyogo (JP); Jean-Luc Birbaum, Binningen (CH); Kurt Dietliker, Allschwil (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/338,152

(22) Filed: Jun. 23, 1999

(30) Foreign Application Priority Data

Jun. 26, 1998 (EP) .............................. 98810595

(51) Int. Cl.$^7$ ..................... C07C 251/64; C07C 323/47; C07D 295/12; G03F 7/031; G02B 5/20
(52) U.S. Cl. ........................ 430/7; 430/270.1; 522/39; 564/254
(58) Field of Search ............................ 564/254; 430/7, 430/270.1; 522/39

(56) References Cited

U.S. PATENT DOCUMENTS

| | | | | |
|---|---|---|---|---|
| 3,558,309 A | | 1/1971 | Laridon et al. | 96/35.1 |
| 4,202,697 A | | 5/1980 | Van Goethem et al. | 430/306 |
| 4,255,513 A | | 3/1981 | Laridon et al. | 430/281 |
| 4,590,145 A | | 5/1986 | Itoh et al. | 430/281 |
| 5,019,482 A | | 5/1991 | Ai et al. | 430/283 |
| 6,159,654 A | * | 12/2000 | Machida et al. | 430/270.1 |
| 2001/0012596 A1 | * | 8/2001 | Kunimoto et al. | 430/138 |

FOREIGN PATENT DOCUMENTS

| | | | |
|---|---|---|---|
| EP | 0304136 | | 2/1989 |
| EP | 0320264 | | 6/1989 |
| EP | 0636939 | | 2/1995 |
| JP | 62-201859 | * | 9/1987 |

OTHER PUBLICATIONS

Micovic et al., Glas. Hem. Drus. Beograd., (1981), vol. 46, (6), pp. 215–230.
Chem. Abstr. 96:52526c.
J. Chem. Eng. Data, vol. 9, (3), (1964), pp. 403–404.
Chem. Abstr. 61:6944c.
Zee et al., Journal of the Chinese Chemical Society, vol. 41, (1994) pp. 573–577.
Chem. Abstr. 123:111206z.
Chem. Abstr. 109:83463w and Derwent Abstr. 87–273259 for JP 62273259.
Derwent Abstr. 88–025703/04 for JP 62286961.
Derwent Abstr. 87–288481/41 for JP 62201859.
Derwent Abstr. 87–266739/38 for JP 62184056.
Groenenboom et al., Journal of Photochemistry and Photobiology A: Chemistry, vol. 107, (1997), pp. 261–269.
Derwent Abstr. 1998–418102 for JP 10171119.
Patent Abstracts of Japan for JP 09297400.
Derwent Abstract 88–010468 for JP 62273259.
Derwent Abstract for JP1043562.

* cited by examiner

Primary Examiner—John A. McPherson
(74) Attorney, Agent, or Firm—Luther A. R. Hall; David R. Crichton

(57) ABSTRACT

Oximeester compounds of the formulae I, II, III and IV

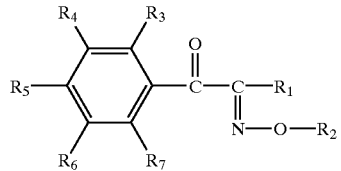
(I)

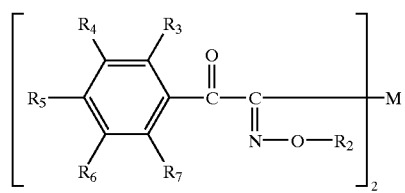

(II)

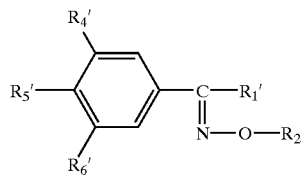

(III)

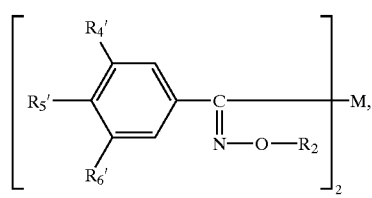

(IV)

wherein $R_1$ is phenyl, $C_1$–$C_{20}$alkyl or $C_2$–$C_{20}$alkyl optionally interrupted by —O—, $C_2$–$C_{20}$alkanoyl or benzoyl, or $R_1$ is $C_2$–$C_{12}$alkoxycarbonyl or phenoxycarbonyl; $R_1'$ is $C_2$–$C_{12}$alkoxycarbonyl, or $R_1'$ is phenoxycarbonyl, or $R_1'$ is —CONR$_{10}$R$_{11}$ or CN; $R_2$ is $C_2$–$C_{12}$alkanoyl, $C_4$–$C_6$alkenoyl, benzoyl, $C_2$–$C_6$alkoxycarbonyl or phenoxycarbonyl; $R_3$, $R_4$, $R_5$, $R_6$ and $R_7$ are hydrogen, halogen, $C_1$–$C_{12}$alkyl, cyclopentyl, cyclohexyl, phenyl, benzyl, benzoyl, $C_2$–$C_{12}$alkanoyl, $C_2$–$C_{12}$alkoxycarbonyl, phenoxycarbonyl or a group OR$_8$, SR$_9$, SOR$_9$, SO$_2$R$_9$ or NR$_{10}$R$_{11}$; $R_4'$, $R_5'$ and $R_6'$ are hydrogen, halogen, $C_1$–$C_{12}$alkyl, cyclopentyl, cyclohexyl, phenyl, benzyl, benzoyl, $C_2$–$C_{12}$-alkanoyl, $C_2$–$C_{12}$alkoxycarbonyl, phenoxycarbonyl, or are a group OR$_8$, SR$_9$, SOR$_9$, SO$_2$R$_9$, NR$_{10}$R$_{11}$; provided that at least one of $R_3$, $R_4$, $R_5$, $R_6$, $R_7$, $R'_4$, $R'_5$ and $R'_6$ is OR$_8$, SR$_9$ or NR$_{10}$R$_{11}$; $R_8$, $R_9$, $R_{10}$ and $R_{11}$ are for example hydrogen, $C_1$–$C_{12}$alkyl, phenyl; are suitable as initiators for the photopolymerization of radically polymerizable compounds.

18 Claims, No Drawings

O-ACYLOXIME PHOTOINITIATORS

The invention pertains to new O-acyloxime compounds and their use as photoinitiators in photopolymerizable compositions.

From U.S. Pat. No. 3,558,309 it is known that certain oxime ester derivatives are photoinitiators. In U.S. Pat. No. 4,255,513 oxime ester compounds are disclosed. In U.S. Pat. No. 4,590,145 several p-dimethyl- and p-diethylamino-substituted oxime ester compounds are disclosed. U.S. Pat. No. 4,202,697 discloses acrylamino-substituted oxime esters. In Chemical Abstract No. 96:52526c, J. Chem. Eng. Data 9(3), 403–4 (1964), J. Chin. Chem. Soc. (Taipei) 41 (5) 573–8, (1994), JP 62-273259-A (=Chemical Abstract 109:83463w), JP 62-286961-A (=Derwent No. 88-025703/04), JP 62-201859-A (=Derwent No. 87-288481/41), JP 62-184056-A (=Derwent No. 87-266739/38), U.S. Pat. No. 5,019,482 and J. of Photochemistry and Photobiology A 107, 261-269 (1997) some p-alkoxy-phenyl oxime ester compounds are described.

In photopolymerization technology there still exists a need for highly reactive, easy to prepare and easy to handle photoinitiators. In addition, such new photoinitiators must meet the high requirements of the industry regarding properties like, for example, thermal stability and storage stability.

Surprisingly it was found, that compounds of the formulae I, II, III and IV

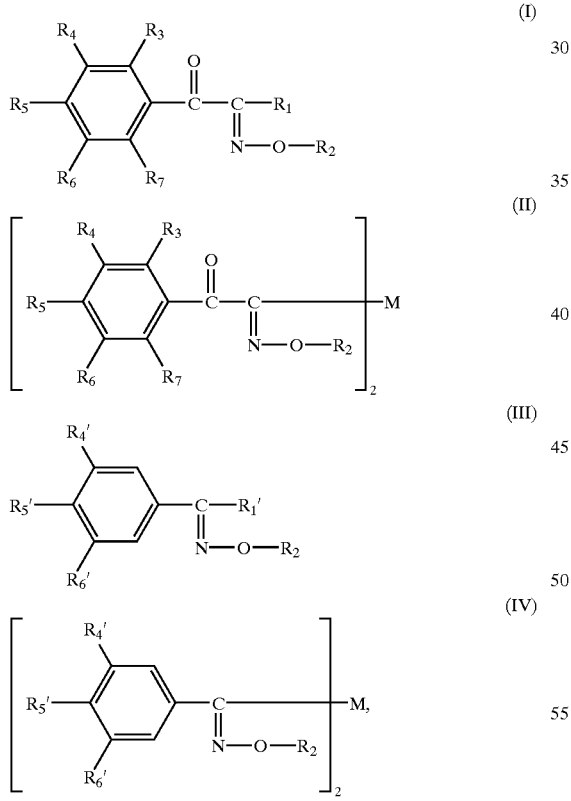

wherein $R_1$ is phenyl which is unsubstituted or substituted by one or more $C_1$–$C_6$alkyl, phenyl, halogen, $OR_8$, $SR_9$ or $NR_{10}R_{11}$; or $R_1$ is $C_1$–$C_{20}$alkyl or $C_2$–$C_{20}$alkyl optionally interrupted by one or more —O— and/or optionally substituted by one or more hydroxyl groups; or $R_1$ is $C_5$–$C_8$cycloalkyl, $C_2$–$C_{20}$alkanoyl; or benzoyl which is unsubstituted or substituted by one or more $C_1$–$C_6$-alkyl, phenyl, $OR_8$, $SR_9$ or $NR_{10}R_{11}$; or $R_1$ is $C_2$–$C_{12}$alkoxycarbonyl optionally interrupted by one or more —O— and/or optionally substituted by one or more hydroxyl groups; or $R_1$ is phenoxycarbonyl which is unsubstituted or substituted by $C_1$–$C_6$alkyl, halogen, phenyl, $OR_8$ or $NR_{10}R_{11}$; or $R_1$ is —$CONR_{10}R_{11}$, CN, $NO_2$, $C_1$–$C_4$haloalkyl, $S(O)_mC_1$–$C_6$alkyl; unsubstituted or $C_1$–$C_{12}$alkyl-substituted $S(O)_m$—$C_6$–$C_{12}$aryl; $SO_2O$—$C_1$–$C_6$alkyl, $SO_2O$—$C_6$–$C_{10}$aryl, or diphenylphosphinoyl;

m is 1 or 2;

$R_1'$ is $C_2$–$C_{12}$alkoxycarbonyl optionally interrupted by one or more —O— and/or optionally substituted by one or more hydroxyl groups; or $R_1'$ is phenoxycarbonyl which is unsubstituted or substituted by one or more $C_1$–$C_6$alkyl, halogen, phenyl, $OR_8$ or $NR_{10}R_{11}$; or $R_1'$ is $C_5$–$C_8$cycloalkyl, —$CONR_{10}OR_{11}$, CN; or phenyl which is substituted by $SR_9$, wherein optionally a 5- or 6-membered ring is formed via the group $R_9$ by building a link to a carbon atom of the phenyl ring bearing the groups $R_4'$, $R_5'$ and $R_6'$; or, if at least one of $R_4'$, $R_5'$ or $R_6'$ is —$SR_9R_1'$ additionally is $C_1$–$C_{12}$alkyl which is unsubstituted or substituted by one or more halogen, OH, $OR_2$, phenyl, halogenated phenyl or phenyl substituted by $SR_9$, and which $C_1$–$C_{12}$alkyl otpionally is interrupted by —O— or —NH—(CO)—;

$R_2$ is $C_2$–$C_{12}$alkanoyl which is unsubstituted or substituted by one or more halogen or CN; or $R_2$ is $C_4$–$C_6$alkenoyl, provided that the double bond is not conjugated with the carbonyl group; or $R_2$ is benzoyl which is unsubstituted or substituted by one or more $C_1$–$C_6$alkyl, halogen, CN, $OR_8$, $SR_9$ or $NR_{10}R_{11}$; or $R_2$ is $C_2$–$C_6$alkoxycarbonyl; or phenoxycarbonyl which is unsubstituted or substituted by $C_1$–$C_6$alkyl or halogen;

$R_3$, $R_4$, $R_5$, $R_6$ and $R_7$ independently of one another are hydrogen, halogen, $C_1$–$C_{12}$alkyl, cyclopentyl, cyclohexyl; or phenyl which is unsubstituted or substituted by one or more $OR_8$, $SR_9$ or $NR_{10}R_{11}$; or $R_3$, $R_4$, $R_5$, $R_6$ and $R_7$ are benzyl, benzoyl, $C_2$–$C_{12}$alkanoyl; $C_2$–$C_{12}$-alkoxycarbonyl optionally interrupted by one or more —O— and/or optionally substituted by one or more hydroxyl groups; or $R_3$, $R_4$, $R_5$, $R_6$ and $R_7$ are phenoxycarbonyl or a group $OR_8$, $SR_9$, $SOR_9$, $SO_2R_9$ or $NR_{10}R_{11}$, wherein the substituents $OR_8$, $SR_9$ and $NR_{10}R_{11}$ optionally form 5- or 6-membered rings via the radicals $R_8$, $R_9$, $R_{10}$ and/or $R_{11}$ with further substituents on the phenyl ring or with one of the carbon atoms of the phenyl ring;

provided that at least one of the groups $R_3$, $R_4$, $R_5$, $R_6$ or $R_7$ is $OR_8$, $SR_9$ or $NR_{10}R_{11}$;

$R_4'$, $R_5'$ and $R_6'$ independently of one another are hydrogen, halogen, $C_1$–$C_{12}$alkyl, cyclopentyl, cyclohexyl; phenyl which is unsubstituted or substituted by $OR_8$, $SR_9$ or $NR_{10}R_{11}$; or $R_4'$, $R_5'$ and $R_6'$ are benzyl, benzoyl, $C_2$–$C_{12}$alkanoyl; $C_2$–$C_{12}$alkoxycarbonyl optionally interrupted by one or more —O— and/or optionally substituted by one or more hydroxyl groups; or $R_4'$, $R_5'$ and $R_6'$ are phenoxycarbonyl; or are a group $OR_8$, $SR_9$, $SOR_9$, $SO_2R_9$, $NR_{10}R_{11}$, wherein the substituents $OR_8$, $SR_9$ and $NR_{10}R_{11}$ optionally form 5- or 6-membered rings via the radicals $R_8$, $R_9$, $R_{10}$ and/or $R_{11}$ with further substituents on the phenyl ring or with one of the carbon atoms of the phenyl ring;

provided that at least one of $R'_4$, $R'_5$ and $R'_6$ is $OR_8$, $SR_9$ or $NR_{10}R_{11}$;

and provided that if $R'_5$ is methoxy and $R'_4$ and $R'_6$ are both simultaneously hydrogen and $R'_1$ is CN, $R'_2$ is not benzoyl or 4-($C_1$–$C_{10}$alkyl)benzoyl;

$R_8$ is hydrogen, $C_1$–$C_{12}$alkyl; or $C_2$–$C_6$alkyl which is substituted by —OH, —SH, —CN, $C_1$–$C_4$-alkoxy, $C_3$–$C_6$alkenoxy, —$OCH_2CH_2CN$, —$OCH_2CH_2(CO)O$ ($C_1$–$C_4$alkyl), —$O(CO)$—$C_1$–$C_4$alkyl, —$O(CO)$-phenyl, —$(CO)OH$ or —$(CO)O(C_1$–$C_4$alkyl); or $R_8$ is $C_2$–$C_6$alkyl which is interrupted by one or more —O—; or $R_8$ is —$(CH_2CH_2O)_nH$, $C_2$–$C_8$alkanoyl, $C_3$–$C_{12}$alkenyl, $C_3$–$C_6$alkenoyl, cyclohexyl; or phenyl which is unsubstituted or substituted by halogen, $C_1$–$C_{12}$alkyl or $C_1$–$C_4$alkoxy; or $R_8$ is phenyl-$C_1$–$C_3$alkyl, $Si(C_1$–$C_8$alkyl)r(phenyl)$_{3-r}$, or a group

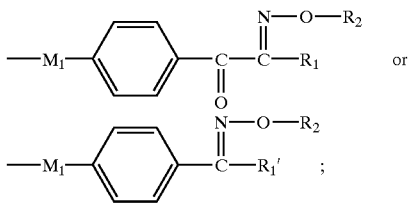

n is 1–20;
r is 1, 2 or 3;

$R_9$ is hydrogen, $C_1$–$C_{12}$alkyl, $C_3$–$C_{12}$alkenyl, cyclohexyl; $C_2$–$C_6$alkyl which is substituted by —OH, —SH, —CN, $C_1$–$C_4$alkoxy, $C_3$–$C_6$alkenoxy, —$OCH_2CH_2CN$, —$OCH_2CH_2(CO)O(C_1$–$C_4$alkyl), —$O(CO)$—$C_1$–$C_4$alkyl, —$O(CO)$-phenyl, —$(CO)OH$ or —$(CO)O(C_1$–$C_4$alkyl); or $R_9$ is $C_2$–$C_{12}$alkyl which is interrupted by one or more —O— or —S—; or $R_9$ is phenyl which is unsubstituted or substituted by halogen, $C_1$–$C_{12}$alkyl or $C_1$–$C_4$alkoxy; or $R_9$ is phenyl-$C_1$–$C_3$alkyl or a group

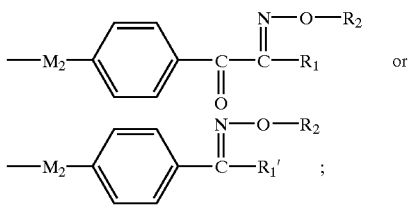

$R_{10}$ and $R_{11}$ independently of each other are hydrogen, $C_1$–$C_{12}$alkyl, $C_2$–$C_4$hydroxyalkyl, $C_2$–$C_{10}$alkoxyalkyl, $C_3$–$C_5$alkenyl, $C_5$–$C_{12}$cycloalkyl, phenyl-$C_1$–$C_3$alkyl; phenyl which is unsubstituted or substituted by $C_1$–$C_{12}$alkyl or $C_1$–$C_4$alkoxy; or $R_{10}$ and $R_{11}$ are $C_2$–$C_3$alkanoyl, $C_3$–$C_6$-alkenoyl or benzoyl; or $R_{10}$ and $R_{11}$ together are $C_2$–$C_6$alkylene optionally interrupted by —O— or —$NR_8$— and/or optionally substituted by hydroxyl, $C_1$–$C_4$alkoxy, $C_2$–$C_4$alkanoyloxy or benzoyloxy; or, when $R_{10}$ is hydrogen, $R_{11}$ may be a group of formula

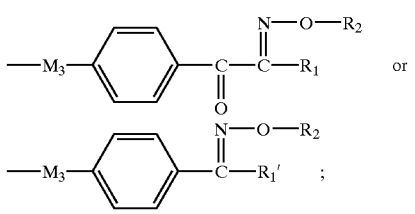

M is $C_1$–$C_{12}$alkylene, cyclohexylene, phenylene, —$(CO)O$—$(C_2$–$C_{12}$alkylene)—$O(CO)$—, —$(CO)O$—$(CH_2CH_2O)_n$—$(CO)$— or —$(CO)$—$(C_2$–$C_{12}$-alkylene)-$(CO)$—;

$M_1$ is a direct bond; or $C_1$–$C_{12}$alkyleneoxy-, optionally interrupted by 1 to 5 —O—, —S— and/or —$NR_{10}$—;

$M_2$ is a direct bond; or $C_1$–$C_{12}$alkylene-S-, optionally interrupted by 1 to 5 —O—, —S— and/or —$NR_{10}$—;

$M_3$ is a direct bond, a piperazino group; or $C_1$–$C_{12}$alkylene-NH— optionally interrupted by 1 to 5 —O—, —S— and/or —$NR_{10}$—;

provided that
(i) if $R_5$ is methoxy and $R_2$ is benzoyl or acetyl then $R_1$ is not phenyl;
(ii) if $R_5$ is methoxy and $R_1$ is ethoxycarbonyl, then $R_2$ is not benzoyl or ethoxycarbonyl;
(iii) if $R_5$ is methoxy and $R_1$ is 4-methoxybenzoyl, then $R_2$ is not ethoxycarbonyl;
(iv) if $R_5$ is methacryloylamino and $R_1$ is methyl, then $R_2$ is not benzoyl;
(v) if both, $R_5$ and $R_4$ or $R_5$ and $R_6$, are $OR_8$ and these $OR_8$ groups together form a ring via $R_8$ and thereby give —O—$CH_2$—O—, and $R_1$ is methyl, then $R_2$ is not acetyl;
(vi) if $R_4$, $R_5$ and $R_6$ simultaneously are methoxy and $R_1$ is ethoxycarbonyl, then $R_2$ is not acetyl;
(vii) if $R_5$ is methoxy and simultaneously $R_4$ or $R_6$ are acetoxy and RI is ethyl, then $R_2$ is not acetyl;
(viii) if, in formula III, $R_1$' is methyl, $R_5$' is phenylthio, and $R_4$' and $R_6$' both are H, then $R_2$ is not 4-chlorobenzoyl.

exhibit an unexpectedly good performance in photopolymerization reactions.

The compounds of the formulae I, II, III and IV are characterized in that they contain at least one alkoxy, aryloxy, alkylthio, arylthio, alkylamino or arylamino substituent directly connected to the phenyl or benzoyl group linked to the carbon atom of the oximino function.

Substituted radicals phenyl are substituted one to four times, for example one, two or three times, especially two times. Substituents on the phenyl ring are preferably in positions 4 or in 3,4-, 3,4,5-, 2,6-, 2,4- or 2,4,6-configuration on the phenyl ring, in particular in 4- or 3,4-position.

$C_1$–$C_{20}$alkyl is linear or branched and is, for example, $C_1$–$C_{18}$-, $C_1$–$C_{14}$-, $C_1$–$C_{12}$-, $C_1$–$C_8$-, $C_1$–$C_6$- or $C_1$–$C_4$alkyl or $C_4$–$C_{12}$- or $C_4$–$C_8$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl, octadecyl and icosyl. $C_1$–$C_{12}$alkyl, $C_2$–$C_{12}$alkyl, $C_1$–$C_8$alkyl, $C_1$–$C_6$alkyl, $C_2$–$C_6$alkyl and $C_1$–$C_4$alkyl have the same meanings as given above for $C_1$–$C_{20}$alkyl up to the corresponding number of C-atoms.

$C_2$–$C_{20}$alkyl which is interrupted by one or more —O— is for example interrupted 1-9, 1-5, 1-3 or once or twice by —O—. Two O-atoms are separated by at least two methylene groups, namely ethylene. The alkyl groups are linear or branched. For example the following structural units will occur, —$CH_2$—$CH_2$—O—$CH_2CH_3$, —$[CH_2CH_2O]_y$-$CH_3$, wherein y=1-9, —$(CH_2$—$CH_2O)_7CH_2CH_3$, —$CH_2$—CH($CH_3$)—O—$CH_2$—$CH_2CH_3$ or —$CH_2$—$CH(CH_3)$—O—$CH_2$—$CH_3$. $C_2$–$C_6$alkyl which is interrupted by 1 or 2 —O— is for example —$CH_2CH_2$—O—$CH_2CH_2$—$OCH_2CH_3$ or —$CH_2CH_2$ $C_2$–$C_4$hydroxyalkyl means $C_2$–$C_4$alkyl, which substituted by one or two O-atoms. The alkyl radical is linear or branched. Examples are 2-hydroxyethyl, 1 -hydroxyethyl, 1-hydroxypropyl, 2-hydroxypropyl, 3-hydroxypropyl, 1-hydroxybutyl, 4-hydroxybutyl, 2-hydroxybutyl, 3-hydroxybutyl, 2,3-dihydroxypropyl, or 2,4-dihydroxybutyl.

$C_5$–$C_{12}$Cycloalkyl is for example cyclopentyl, cyclohexyl, cyclooctyl, cyclododecyl, especially cyclopentyl and cyclohexyl, preferably cyclohexyl.

$C_1$–$C_4$alkoxy is linear or branched, for example, methoxy, ethoxy, propoxy, isopropoxy, n-butyloxy, sec-butyloxy, isobutyloxy, tert-butyloxy.

$C_2$–$C_{10}$alkoxyalkyl is $C_2$–$C_{10}$alkyl, which is interrupted by one O-atom. $C_2$–$C_{10}$alkyl has the same meanings as given above for $C_1$–$C_{20}$alkyl up to the corresponding number of C-atoms. Examples are methoxymethyl, methoxyethyl, methoxypropyl, ethoxymethyl, ethoxyethyl, ethoxypropyl, porpoxymethyl, prpopxyethyl, propoxypropyl.

$C_2$–$C_{20}$alkanoyl is linear or branched and is, for example, $C_2$–$C_{18}$-, $C_2$–$C_{14}$-, $C_2$–$C_{12}$-, $C_2$–$C_8$-, $C_2$–$C_6$- or $C_2$–$C_4$alkanoyl or $C_4$–$C_{12}$- or $C_4$–$C_8$alkanoyl. Examples are acetyl, propionyl, butanoyl, isobutanoyl, pentanoyl, hexanoyl, heptanoyl, octanoyl, nonanoyl, decanoyl, dodecanoyl, tetradecanoyl, pentadecanoyl, hexadecanoyl, octadecanoyl, icosanoyl, preferably acetyl.

$C_2$–$C_{12}$alkanoyl, $C_2$–$C_8$alkanoyl, $C_2$–$C_6$alkanoyl and $C_2$–$C_4$alkanoyl have the same meanings as given above for $C_2$–$C_{20}$alkanoyl up to the corresponding number of C-atoms.

$C_2$–$C_4$alkanoyloxy is linear or branched, for example acetyloxy, propionyloxy, butanoyloxy, isobutanoyloxy, preferably acetyloxy.

$C_2$–$C_{12}$alkoxycarbonyl is a linear or branched and is, for example, methoxycarbonyl, ethoxycarbonyl, propoxycarbonyl, n-butyloxycarbonyl, isobutyloxycarbonyl, 1,1-dimethylpropoxycarbonyl, pentyloxycarbonyl, hexyloxycarbonyl, heptyloxycarbonyl, octyloxycarbonyl, nonyloxycarbonyl, decyloxycarbonyl or dodecyloxycarbonyl, especially methoxycarbonyl, ethoxycarbonyl, propoxycarbonyl, n-butyloxycarbonyl or iso-butyloxycarbonyl, preferably methoxycarbonyl.

$C_2$–$C_6$alkoxycarbonyl and $C_2$–$C_4$alkoxycarbonyl have the same meanings as given above for $C_2$–$C_{12}$alkoxycarbonyl up to the corresponding number of C-atoms.

$C_2$–$C_{12}$alkoxycarbonyl which is interrupted by one or more —O— is linear or branched. Two O-atoms are separated by at least two methylene groups, namely ethylene.

Phenoxycarbonyl is

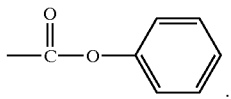

Substituted phenoxycarbonyl radicals are substituted one to four times, for example one, two or three times, especially two or three times. Substituents on the phenyl ring are preferably in positions 4 or in 3,4-, 3,4,5-, 2,6-, 2,4- or 2,4,6-position on the phenyl ring, in particular in 4- or 3,4-position.

Phenyl-$C_1$–$C_3$alkyl is for example benzyl, phenylethyl, α-methylbenzyl or α,α-dimethylbenzyl, especially benzyl.

$C_3$–$C_{12}$alkenyl radicals may be mono- or polyunsaturated and are for example allyl, methallyl, 1,1-dimethylallyl, 1-butenyl, 3-butenyl, 2-butenyl, 1,3-pentadienyl, 5-hexenyl, 7-octenyl or dodecenyl, especially allyl.

$C_3$–$C_6$alkenoxy radicals may be mono- or polyunsaturated and are for example allyloxy, methallyloxy, butenyloxy, pentenoxy, 1,3-pentadienyloxy, 5-hexenyloxy.

$C_3$–$C_6$alkenoyl radicals may be mono- or polyunsaturated and are for example propenoyl, 2-methyl-propenoyl, butenoyl, pentenoyl, 1,3-pentadienoyl, 5-hexenoyl.

Methylsulfanyl is —SCH$_3$.

Halogen is fluorine, chlorine, bromine and iodine, especially fluorine, chlorine and bromine, preferably fluorine and chlorine.

$C_6$–$C_{12}$aryl is for example phenyl, 1-naphthyl, 2-naphthyl, preferably phenyl.

If the substituents OR$_8$, SR$_9$ and NR$_{10}$R$_{11}$ on a phenyl ring form 5- or 6-membered rings via the radicals R$_8$, R$_9$, R$_{10}$ and/or R$_{11}$ with further substituents on the phenyl ring or with one of the carbon atoms of the phenyl ring, structures comprising two or four rings (inclusive the phenyl ring) are obtained. Examples are

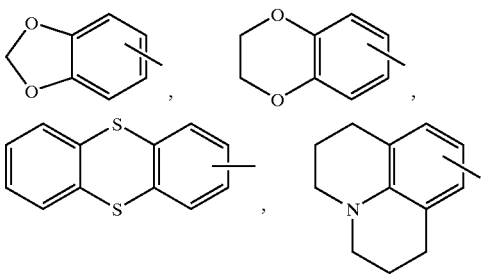

If R$_1$' is phenyl which is substituted by SR$_9$, wherein optionally a 5- or 6-membered ring is formed via the group R$_9$ by building a link to a carbon atom of the phenyl ring bearing the groups R$_4$', R$_5$' and R$_6$', for example, the following structure may be formed

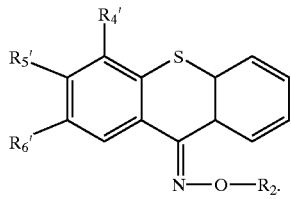

Compounds of formula II, wherein R$_9$ is phenyl and R$_2$ is halogen-substituted benzoyl preferably are excluded from the aforementioned definition.

Preferred are compounds of formula I and III, wherein

R$_1$ is phenyl which is unsubstituted or substituted by $C_1$–$C_6$alkyl, phenyl, OR$_8$, SR$_9$ or NR$_{10}$R$_{11}$; or R$_1$ is $C_1$–$C_{20}$alkyl, optionally interrupted by one or more —O— and/or optionally substituted by one or more hydroxyl groups; or R$_1$ is $C_1$–$C_4$haloalkyl;

R$_1$' is phenoxycarbonyl which is unsubstituted or substituted by $C_1$–$C_6$alkyl, halogen, phenyl, OR$_8$, NR$_{10}$R$_{11}$; or R$_1$' is —CONR$_{10}$R$_{11}$; or, if at least one of R$_4$', R$_5$' or R$_6$' is —SR$_9$, R$_1$' additionally is $C_1$–$C_{12}$alkyl which is unsubstituted or substituted by one or more halogen, OH, OR$_2$, phenyl, halogenated phenyl or phenyl substituted by SR$_9$, and which $C_1$–$C_{12}$alkyl otpionally is interrupted by —O— or —NH—(CO)—;

R$_2$ is $C_2$–$C_{12}$alkanoyl which is unsubstituted or substituted by halogen; or R$_2$ is $C_4$–$C_6$alkenoyl provided that the double bond is not conjugated with the carbonyl group; or R$_2$ is benzoyl which is unsubstituted or substituted by one or more $C_1$–$C_6$alkyl or halogen;

R$_3$ and R$_7$ are hydrogen;

R$_4$, R$_6$, R$_4$' and R$_6$' independently of one another are hydrogen, halogen, $C_1$–$C_{12}$alkyl, OR$_8$ or SR$_9$, wherein the substituents OR$_8$ and SR$_9$ optionally form 5- or 6-membered rings via the radicals R$_8$ and/or R$_9$ with further substituents on the phenyl ring or with one of the carbon atoms of the phenyl ring; and R$_5$ and R$_5$' are OR$_8$ or SR$_9$.

Particularly preferred are compounds of formula I or 111, wherein at least one of R$_3$, R$_4$, R$_5$, R$_6$ or R$_7$ or R$_4$', R$_5$' or R$_6$' is SR$_9$ or NR$_{10}$R$_{11}$.

Other preferred compounds of the formula I are such, wherein formula I, R$_3$ and R$_7$ are hydrogen and R$_4$ and R$_5$ both are OR$_8$.

In particular compounds of the formula I or III, wherein $R_3$, $R_4$ and $R_7$ or $R_4'$ and $R_6'$ are hydrogen and $R_5$ or $R_5'$ is $SR_9$. In particular preferred are such compounds wherein $R_9$ is phenyl, i.e. compounds wherein $R_5$ or $R_5'$ is

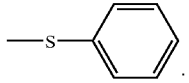

Compounds of formula III, wherein $R_1'$ is $C_1$–$C_{12}$alkyl which is unsubstituted or substituted by halogen or phenyl are preferred, especially those, wherein $R_5'$ is $SR_9$, in particular

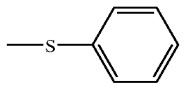

Further interest is directed to of formula I, II, III or IV wherein $R_1$ is phenyl, $C_1$–$C_{12}$alkyl;

$R_1'$ is $C_2$–$C_4$alkoxycarbonyl, or phenyl which is substituted by $SR_9$, wherein a 5- or 6-membered ring is formed via the group $R_9$ by building a link to a carbon atom of the phenyl ring bearing the groups $R_4'$, $R_5'$ and $R_6'$; or, if at least one of $R_4'$, $R_5'$ or $R_6'$ is —$SR_9$, $R_1'$ is $C_1$–$C_{12}$alkyl which is unsubstituted or substituted by phenyl or one or more fluorine;

$R_2$ is $C_2$–$C_4$alkanoyl, or benzoyl which is unsubstituted or substituted by one or more $C_1$–$C_4$alkyl or halogen;

$R_3$, $R_6$ and $R_7$ are hydrogen;

$R_4$ and $R_5$ independently of one another are hydrogen or a group $OR_8$, $SR_9$, or $NR_{10}R_{11}$;

$R_4'$ and $R_5'$ independently of one another are hydrogen or a group $OR_8$, $SR_9$, or $NR_{10}R_{11}$;

$R_6'$ is hydrogen; F $R_8$ and $R_9$ are $C_1$–$C_4$alkyl, phenyl or a group

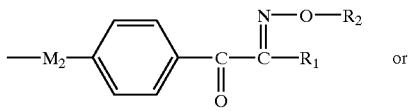

or

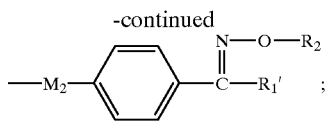

$R_{10}$ and $R_{11}$ are methyl or ethyl, or $R_{10}$ and $R_{11}$ together are $C_2$–$C_6$alkylene which is interrupted by —O—

M is $C_1$–$C_{12}$alkylene; and $M_2$ is a direct bond.

Of further interest are compounds of the formula III, wherein $R_4'$ and $R_6'$ are hydrogen and $R_5'$ is $SR_9$.

$R_1$ preferably is phenyl which is unsubstituted or substituted by one or more $C_1$–$C_6$alkyl, phenyl, halogen, $OR_8$, $SR_9$ or $NR_{10}R_{11}$, or $R_1$ is $CO_1$–$C_{20}$alkyl which is unsubstituted or substituted by one or more $C_1$–$C_6$alkyl, phenyl, $OR_8$, $SR_9$ or $NR_{10}R_{11}$.

In particular preferred are compounds, wherein at least one of the groups $R_3$–$R_7$ is $SR_9$, $OR_8$ or, especially those, wherein at least one of the groups $R_3$–$R_7$ is $NR_{10}R_{11}$ or $SR_9$, in particular $SR_9$.

$R_5$ preferably is $SR_9$, $OR_8$ or $NR_{10}R_{11}$, in particular $SR_9$ or $NR_{10}R_{11}$, especially $SR_9$. Preferred are compounds of formulae I and III.

Preferred are further compounds, wherein $R_3$ and $R_7$ are hydrogen.

$R_1$ is preferably $C_1$–$C_{12}$alkyl.

$R_2$ is preferably benzoyl, methylbenzoyl, dimethylbenzoyl or acetyl.

$R_6'$ preferably is hydrogen.

$R_1'$ preferably is $C_1$–$C_{12}$alkyl or 4-($C_1$–$C_4$alkylthio) phenyl $R_5'$ preferably is $C_1$–$C_4$alkylthio or phenylthio.

Preferred compounds according to the present invention are 1-(4-phenylsulfanyl-phenyl)-butan-1,2-dione 2-oxime-O-benzoate, 1-(4-phenylsulfanyl-phenyl)-octan-1,2-dione 2-oxime-O-benzoate, 1-(4-phenylsulfanyl-phenyl)-octan-1-one oxime-O-acetate, 1-(4-phenylsulfanyl-phenyl)-butane-1-one oxime-O-acetate, in particular 1-(4-phenylsulfanyl-phenyl)-octan-1,2-dione 2-oxime-O-benzoate.

Oxime esters of formulae I, II, III and IV are prepared by methods described in the literature, for example by reaction of the corresponding oximes ($R_2$=H) with an acyl chloride or an anhydride in an inert solvent such as for example tetrahydrofuran or dimethylformamide in the presence of a base, for example a tertiary amine, such as triethylamine, or in a basic solvent such as pyridine.

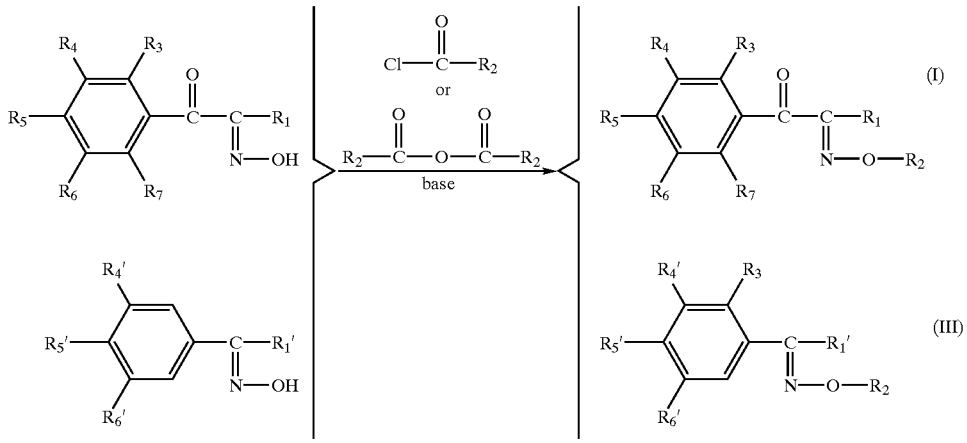

Such reactions are well known to those skilled in the art, and are generally carried out at temperatures of −15 to +50° C., preferably 0 to 20° C.

The compounds of formulae II and IV can be obtained analogously by using the appropriate oximes as starting materials:

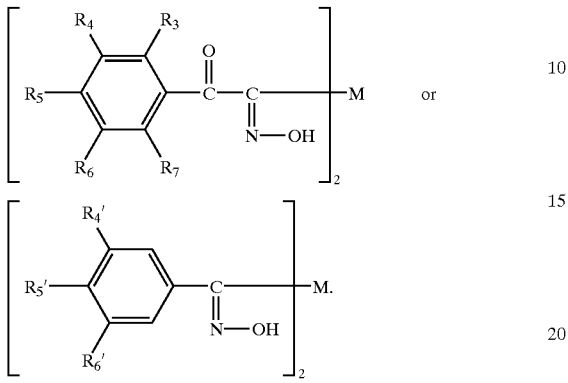

$R_1$–$R_7$ and $R_1'$, $R_4'$, $R_5'$, $R_6'$ and M have the meanings given above.

The oximes required as starting materials can be obtained by a variety of methods described in standard chemistry textbooks (for instance in J. March, Advanced Organic Chemistry, 4th Edition, Wiley Interscience, 1992), or in specialized monographs, for example, S. R. Sandier & W. Karo, Organic functional group preparations, Vol. 3, Academic Press. One of the most convenient methods is, for example, the reaction of ketones with hydroxylamine or its salt in polar solvents like ethanol or aqueous ethanol. In that case, a base such as sodium acetate is added to control the pH of the reaction mixture. It is well known that the rate of the reaction is pH-dependent, and the base can be added at the beginning or continuously during the reaction. Basic solvents such as pyridine can also be used as base and/or solvent or cosolvent. The reaction temperature is generally the refluxing temperature of the mixture, usually 60–120° C. Another convenient synthesis of oximes is the nitrosation of "active" methylene groups with nitrous acid or an alkyl nitrite. Both alkaline conditions, as described for example in Organic Syntheses coll. Vol. VI (J. Wiley & Sons, New York, 1988), pp 199 and 840, and acidic conditions, as described, for example, in Organic Synthesis coll. vol V, pp 32 and 373, coll. vol. III, pp 191 and 513, coll. vol.II, pp. 202, 204 and 363, are suitable for the preparation of the oximes used as starting materials in the invention. Nitrous acid is usually generated from sodium nitrite. The alkyl nitrite can be for example methyl nitrite, ethyl nitrite, isopropyl nitrite, butyl nitrite, isoamyl nitrite.

Every oxime ester group can exist in two configurations, (Z) or (E). It is possible to separate the isomers by conventional methods, but it is also possible to use the isomeric mixture as photoinitiating species. Therefore the invention also relates to mixtures of configurational isomers of compounds of the formulae I, II, III and IV.

In accordance with the invention, the compounds of the formulae I, II, III and IV can be used as photoinitiators for the photopolymerization of ethylenically unsaturated compounds or of mixtures which comprise such compounds.

The invention therefore also relates to photopolymerizable compositions comprising
 (a) at least one ethylenically unsaturated photopolymerizable compound and
 (b) as photoinitiator, at least one compound of the formula I, II, III and/or IV

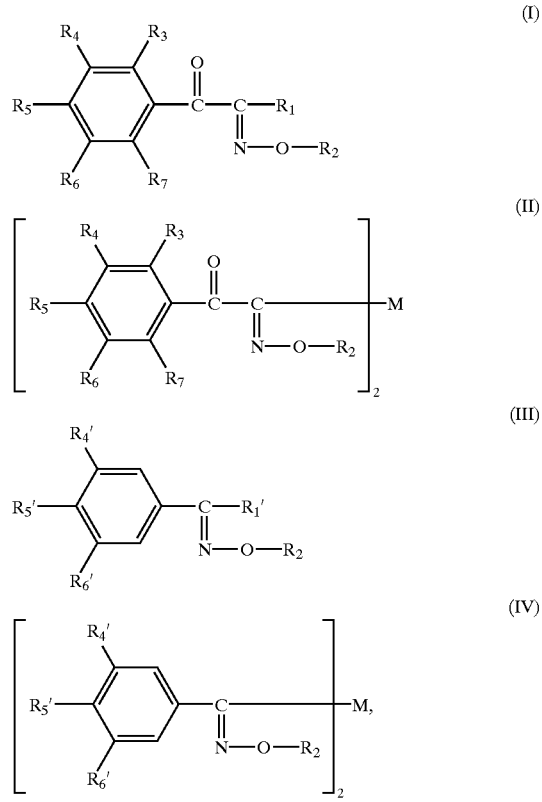

wherein
$R_1$ is phenyl which is unsubstituted or substituted by one or more $C_1$–$C_6$alkyl, phenyl, halogen, $OR_8$, $SR_9$ or $NR_{10}R_{11}$; or $R_1$ is $C_5$–$C_8$cycloalkyl, $C_1$–$C_{20}$alkyl; or $C_2$–$C_{20}$alkyl optionally interrupted by one or more —O— and/or optionally substituted by one or more hydroxyl groups; or $R_1$ is $C_2$–$C_{20}$alkanoyl; or is benzoyl which is unsubstituted or substituted by one or more $C_1$–$C_6$alkyl, phenyl, $OR_8$, $SR_9$ or $NR_{10}R_{11}$; or $R_1$ is $C_2$–$C_{12}$alkoxycarbonyl optionally interrupted by one or more —O— and/or optionally substituted by one or more hydroxyl groups; or $R_1$ is phenoxycarbonyl which is unsubstituted or substituted by $C_1$–$C_6$alkyl, halogen, phenyl, $OR_8$ or $NR_{10}R_{11}$; or $R_1$ is —$CONR_{10}R_{11}$, CN, $NO_2$, $C_1$–$C_4$haloalkyl, $S(O)_mC_1$–$C_6$alkyl; unsubstituted or $C_1$–$C_{12}$alkyl-substituted $S(O)_m$–$C_6$–$C_{12}$aryl; $SO_2O$—$C_1$–$C_6$alkyl, $SO_2O$—$C_6$–$C_{10}$aryl, phosphinoyl;
m is 1 or 2;
$R_1'$ is $C_2$–$C_{12}$alkoxycarbonyl optionally interrupted by one or more —O— and/or optionally substituted by one or more hydroxyl groups; or $R_1'$ is phenoxycarbonyl which is unsubstituted or substituted by one or more $C_1$–$C_6$alkyl, halogen, phenyl, $OR_8$ or $NR_{10}R_{11}$; or $R_1'$ is $C_5$–$C_8$cycloalkyl, —$CONR_{10}R_{11}$, CN; or phenyl which is substituted by $SR_9$, wherein optionally a 5- or 6-membered ring is formed via the group $R_9$ by building a link to a carbon atom of the phenyl ring bearing the groups $R_4'$, $R_5'$ and $R_6'$; or, if at least one of $R_4'$, $R_5'$ or $R_6'$ is —$SR_9R_1'$ additionally is $C_1$–$C_{12}$alkyl which is unsubstituted or substituted by one or more halogen, OH, $OR_2$, phenyl, halogenated phenyl or phenyl substituted by $SR_9$, and which $C_1$–$C_{12}$alkyl otpionally is interrupted by —O— or —NH—(CO)—;

$R_2$ is $C_2$–$C_{12}$alkanoyl which is unsubstituted or substituted by one or more halogen or CN; or $R_2$ is $C_4$–$C_6$alkenoyl, provided that the double bond is not conjugated with the carbonyl group; or $R_2$ is benzoyl which is unsubstituted or substituted by one or more $C_1$–$C_6$alkyl, halogen CN, $OR_8$, $SR_9$ or $NR_{10}R_{11}$; or $R_2$ is $C_2$–$C_6$alkoxycarbonyl; or phenoxycarbonyl which is unsubstituted or substituted by $C_1$–$C_6$alkyl or halogen;

$R_3$, $R_4$, $R_5$, $R_6$ and $R_7$ independently of one another are hydrogen, halogen, $C_1$–$C_{12}$alkyl, cyclopentyl, cyclohexyl; or phenyl which is unsubstituted or substituted by one or more $OR_8$, $SR_9$ or $NR_{10}R_{11}$; or $R_3$, $R_4$, $R_5$, $R_6$ and $R_7$ are benzyl, benzoyl, $C_2$–$C_{12}$alkanoyl; $C_2$–$C_{12}$alkoxycarbonyl optionally interrupted by one or more —O— and/or optionally substituted by one or more hydroxyl groups; or $R_3$, $R_4$, $R_5$, $R_6$ and $R_7$ are phenoxycarbonyl; $OR_8$, $SR_9$, $SOR_9$, $SO_2R_9$ or $NR_{10}R_{11}$, wherein the substituents $OR_8$, $SR_9$ and $NR_{10}R_{11}$ optionally form 5- or 6-membered rings via the radicals $R_8$, $R_9$, $R_{10}$ and/or $R_{11}$ with further substituents on the phenyl ring or with one of the carbon atoms of the phenyl ring; provided that at least one of the groups $R_3$, $R_4$, $R_5$, $R_6$ or $R_7$ is $OR_8$, $SR_9$ or $NR_{10}R_{11}$;

$R_4'$, $R_5'$ and $R_6'$ independently of one another are hydrogen, halogen, $C_1$–$C_{12}$alkyl, cyclopentyl, cyclohexyl; phenyl which is unsubstituted or substituted by $OR_8$, $SR_9$ or $NR_{10}R_{11}$; or $R_4'$, $R_5'$ and $R_6'$ are benzyl, benzoyl, $C_2$–$C_{12}$alkanoyl; $C_2$–$C_{12}$alkoxycarbonyl optionally interrupted by one or more —O— and/or optionally substituted by one or more hydroxyl groups; or $R_4'$, $R_5'$ and $R_6'$ are phenoxycarbonyl; $OR_8$, $SR_9$, $SOR_9$, $SO_2R_9$, $NR_{10}R_{11}$ wherein the substituents $OR_8$, $SR_9$ and $NR_{10}R_{11}$ optionally form 5- or 6-membered rings via the radicals $R_8$, $R_9$, $R_{10}$ and/or $R_{11}$ with further substituents on the phenyl ring or with one of the carbon atoms of the phenyl ring; provided that at least one of $R'_4$, $R'_5$ and $R'_6$ is $OR_8$, $SR_9$ or $NR_{10}R_{11}$, and provided that if $R'_5$ is methoxy and $R'_4$ and $R'_6$ are both simultaneously hydrogen and $R'_1$ is CN, $R'_2$ is not benzoyl or 4-($C_1$–$C_{10}$alkyl)benzoyl;

$R_8$ is hydrogen, $C_1$–$C_{12}$alkyl; or $C_2$–$C_6$alkyl which is substituted by —OH, —SH, —CN, $C_1$–$C_4$alkoxy, $C_3$–$C_6$alkenoxy, —OCH$_2$CH$_2$CN, —OCH$_2$CH$_2$(CO)O($C_1$–$C_4$alkyl), —O(CO)—$C_1$–$C_4$alkyl, —O(CO)-phenyl, —(CO)OH or —(CO)O($C_1$–$C_4$alkyl); or $R_8$ is $C_2$–$C_6$alkyl which is interrupted by one or more —O—; or $R_8$ is —(CH$_2$CH$_2$O)$_n$H, $C_2$–$C_8$alkanoyl, $C_3$–$C_{12}$alkenyl, $C_3$–$C_6$alkenoyl, cyclohexyl; or is phenyl which is unsubstituted or substituted by halogen, $C_1$–$C_{12}$alkyl or $C_1$–$C_4$alkoxy; or $R_8$ is phenyl-$C_1$–$C_3$alkyl, Si($C_1$–$C_8$alkyl)$_r$(phenyl)$_{3-r}$, or a group

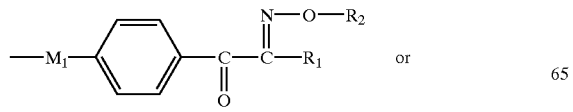

or

-continued

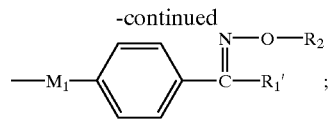

n is 1–20;

r is 1, 2 or 3;

$R_9$ is hydrogen, $C_1$–$C_{12}$alkyl, $C_3$–$C_{12}$alkenyl, cyclohexyl; $C_2$–$C_6$ alkyl which is substituted by —OH, —SH, —CN, $C_1$–$C_4$alkoxy, $C_3$–$C_6$alkenoxy, —OCH$_2$CH$_2$CN, —OCH$_2$CH$_2$(CO)O($C_1$–$C_4$alkyl), —O(CO)—$C_1$–$C_4$alkyl, —O(CO)-phenyl, —(CO)OH or —(CO)O($C_1$–$C_4$alkyl); or $R_9$ is $C_2$–$C_{12}$alkyl which is interrupted by one or more —O— or —S—; or $R_9$ is phenyl which is unsubstituted or substituted by halogen, $C_1$–$C_{12}$alkyl or $C_1$–$C_4$alkoxy; or $R_9$ is phenyl-$C_1$–$C_3$alkyl or a group

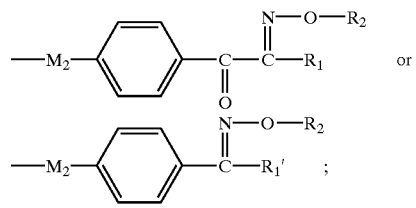

$R_{10}$ and $R_{11}$ independently of each other are hydrogen, $C_1$–$C_{12}$alkyl, $C_2$–$C_4$hydroxyalkyl, $C_2$–$C_{10}$alkoxyalkyl, $C_3$–$C_5$alkenyl, $C_5$–$C_{12}$cycloalkyl, phenyl-$C_1$–$C_3$alkyl; phenyl which is unsubstituted or substituted by $C_1$–$C_{12}$alkyl or $C_1$–$C_4$alkoxy; or $R_{10}$ and $R_{11}$ together are $C_2$–$C_3$alkanoyl, $C_3$–$C_6$-alkenoyl or benzoyl; or $R_{10}$ and $R_{11}$ together are $C_2$–$C_6$alkylene optionally interrupted by —O— or —NR$_8$—, and/or optionally substituted by hydroxyl, $C_1$–$C_4$alkoxy, $C_2$–$C_4$alkanoyloxy or benzoyloxy; or, when $R_{10}$ is hydrogen, $R_{11}$ may be a group of formula

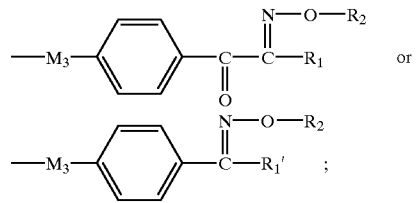

M is $C_1$–$C_{12}$alkylene, cyclohexylene, phenylene, —(CO)O—($C_2$–$C_{12}$alkylene)-O(CO)—, —(CO)O—(CH$_2$CH$_2$O)$_n$—(CO)— or —(CO)—($C_2$–$C_{12}$-alkylene)-(CO)—;

$M_1$ is a direct bond; or $C_1$–$C_{12}$alkyleneoxy-, optionally interrupted by 1 to 5 —O—, —S— and/or —NR$_{10}$—;

$M_2$ is a direct bond; or $C_1$–$C_{12}$alkylene-S—, optionally interrupted by 1 to 5 —O—, —S— and/or —NR$_{10}$—;

$M_3$ is a direct bond, a piperazino group; or $C_1$–$C_{12}$alkylene-NH—, optionally interrupted by 1 to 5 —O—, —S— and/or —NR$_{10}$—;

provided that (i) if $R_5$ is methoxy and $R_2$ is benzoyl or acetyl, then $R_1$ is not phenyl;

(ii) if $R_5$ is methoxy and $R_1$ is ethoxycarbonyl, then $R_2$ is not benzoyl or ethoxycarbonyl;

(iii) if $R_5$ is methoxy and $R_1$ is 4-methoxybenzoyl, then $R_2$ is not ethoxycarbonyl;

(iv) if $R_5$ is methacryloylamino and $R_1$ is methyl, then $R_2$ is not benzoyl;

(v) if both, $R_5$ and $R_4$ or $R_5$ and $R_6$, are $OR_8$ and these $OR_8$ groups together form a ring via $R_8$ and thereby give —O—$CH_2$—O—, and $R_1$ is methyl, then $R_2$ is not acetyl;

(vi) if $R_4$, $R_5$ and $R_6$ simultaneously are methoxy and R, is ethoxycarbonyl, then $R_2$ is not acetyl.

The composition may comprise additionally to the component (b) at least one further photoinitiator (c), and/or further coinitiators (d) and/or other additives.

The unsaturated compounds (a) may include one or more olefinic double bonds. They may be of low (monomeric) or high (oligomeric) molecular mass. Examples of monomers containing a double bond are alkyl or hydroxyalkyl acrylates or methacrylates, for example methyl, ethyl, butyl, 2-ethylhexyl or 2-hydroxyethyl acrylate, isobornyl acrylate, methyl methacrylate or ethyl methacrylate. Silicone acrylates are also advantageous. Other examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride.

Examples of monomers containing two or more double bonds are the diacrylates of ethylene glycol, propylene glycol, neopentyl glycol, hexamethylene glycol or of bisphenol A, and 4,4'-bis(2-acryl-oyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

Examples of polyunsaturated compounds of relatively high molecular mass (oligomers) are acrylated epoxy resins, acrylisized polyesters, polyesters containing vinyl ether or epoxy groups, and also polyurethanes and polyethers. Further examples of unsaturated oligomers are unsaturated polyester resins, which are usually prepared from maleic acid, phthalic acid and one or more diols and have molecular weights of from about 500 to 3000. In addition it is also possible to employ vinyl ether monomers and oligomers, and also maleate-terminated oligomers with polyester, polyurethane, polyether, polyvinyl ether and epoxy main chains. Of particular suitability are combinations of oligomers which carry vinyl ether groups and of polymers as described in WO 90/01512. However, copolymers of vinyl ether and maleic acid-functionalized monomers are also suitable. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, polymers and copolymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxydiphenyl, 2,2-di(4-hydroxyphenyl)propane, and also novolaks and resols.

Examples of polyepoxides are those based on the above-mentioned polyols, especially the aromatic polyols, and epichlorohydrin. Other suitable polyols are polymers and copolymers containing hydroxyl groups in the polymer chain or in side groups, examples being polyvinyl alcohol and copolymers thereof or polyhydroxyalkyl methacrylates or copolymers thereof. Further polyols which are suitable are oligoesters having hydroxyl end groups.

Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glcyol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or completely esterified with one carboxylic acid or with different unsaturated carboxylic acids, and in partial esters the free hydroxyl groups may be modified, for example etherified or esterified with other carboxylic acids.

Examples of esters are:

trimethylolpropane triacrylate, trimethylolethane triacrylate, trimethylolpropane trimeth-acrylate, trimethylolethane trimethacrylate, tetramethylene glycol dimethacrylate, triethylene glypcol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripen-taerythritol octamethacrylate, pentaerythritol diitaconate, dipentaerythritol tris-itaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetra methacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol with a molecular weight of from 200 to 1500, or mixtures thereof.

Also suitable as components (a) are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)- or di(β-aminopropoxy)ethane. Other suitable polyamines are polymers and copolymers, preferably with additional amino groups in the side chain, and oligoamides having amino end groups. Examples of such unsaturated amides are methylenebisacrylamide, 1,6- hexamethylenebisacrylamide, diethylenetriaminetrismethacrylamide, bis(methacrylamidopropoxy)ethane, β-methacrylamidoethyl methacrylate and N[(3-hydroxyethoxy)ethyl]acrylamide.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, especially from those with relatively long chains of, for example 6 to 20 C atoms. Examples of polyurethanes are those composed of saturated or unsaturated diisocyanates and of unsaturated or, respectively, saturated diols.

Polymers with (meth)acrylate groups in the side chain are likewise known. They may, for example, be reaction products of epoxy resins based on novolaks with (meth)acrylic acid, or may be homo- or copolymers of vinyl alcohol or hydroxyalkyl derivatives thereof which are esterified with (meth)acrylic acid, or may be homo- and copolymers of (meth)acrylates which are esterified with hydroxyalkyl (meth)acrylates.

The photopolymerizable compounds can be used alone or in any desired mixtures. It is preferred to use mixtures of polyol (meth)acrylates.

Examples of the component (a) are also polymers or oligomers having at least two ethylenically unsaturated groups and at least one carboxyl function within the molecule structure, such as acid modified epoxyacrylates (for example, EB9696, UCB Chemicals; KAYARAD TCR1025, Nippon Kayaku Co.,LTD.), or acrylated acrylcopolymers (for example, ACA200M, Daicel Industries, Ltd.).

As diluent, a mono- or multi-functional ethylenically unsaturated compound, or mixtures of several of said compounds, can be included in the above composition up to 70% by weight based on the solid portion of the composition.

Binders (e) as well can be added to the novel compositions. This is particularly expedient when the photopolymerizable compounds are liquid or viscous substances. The quantity of binder may, for example, be 2–98%, preferably 5–95% and especially 20–90%, by weight relative to the overall solids content. The choice of binder is made depending on the field of application and on properties required for this field, such as the capacity for development in aqueous and organic solvent systems, adhesion to substrates and sensitivity to oxygen.

Examples of suitable binders are polymers having a molecular weight of about 2,000 to 2,000,000, preferably 5,000 to 1,000,000. Examples of alkali developable binders are acrylic polymer having carboxylic acid function as a pendant group, such as conventionally known copolymers obtained by copolymerizing an ethylenic unsaturated carboxylic acid such as (meth)acrylic acid, 2-carboxyethyl (meth)acrylic acid, 2-carboxypropyl (meth)acrylic acid ithaconic acid, crotonic acid, maleic acid and fumaric acid, with one or more monomers selected from esters of (meth)acrylic acid, such as methyl (meth)acrylate, ethyl (meth)acrylate, propyl (meth)acrylate, butyl (meth)acrylate, benzyl (meth)acrylate, 2-ethylhexyl (meth)acrylate, hydroxyethyl (meth)acrylate, hydroxypropyl (meth)acrylate, benzyl (meth)acrylate; vinyl aromatic compounds, such as styrene, cc-methylstyrene, vinyltoluene, p-chlorostyrene; amide type unsaturated compounds, (meth)acrylamide diacetonacrylamide, N-methylolacrylamide, N-butoxymethacrylamide; and polyolefin type compounds, such as butadiene, isoprene, chloroprene and the like; methacrylonitrile, methyl isopropenyl ketone, vinyl acetate, vinyl propionate, or vinyl pivalate. Examples of copolymers are copolymers of acrylates and methacrylates with acrylic acid or methacrylic acid and with styrene or substituted styrene, phenolic resins, for example novolak, (poly) hydroxystyrene, and copolymers of hydroxystyrene with alkyl acrylates, acrylic acid and/or methacrylic acid. Preferable examples of copolymers are copolymers of methyl methacrylate/methacrylic acid, copolymers of benzyl methacrylate/methacrylic acid, copolymers of methyl methacrylate/ethyl acrylate/methacrylic acid, copolymers of benzyl methacrylate/methacrylic acid/styrene, copolymers of benzyl methacrylate/methacrylic acid/hydroxyethyl methacrylate, copolymers of methyl methacrylate/butyl methacrylate/methacrylic acid/styrene, copolymers of methyl methacrylate/benzyl methacrylate/methacrylic acid/hydroxyphenyl methacrylate. Examples of solvent developable binder polymers are poly(alkyl methacrylates), poly (alkyl acrylates), poly(benzylmethacrylate-co-hydroxyethylmethacrylate-co-methacrylic acid), poly (benzylmethacrylate-co-methacrylic acid); cellulose esters and cellulose ethers, such as cellulose acetate, cellulose acetobutyrate, methylcellulose, ethylcellulose; polyvinylbutyral, polyvinylformal, cyclized rubber, polyethers such as polyethylene oxide, polypropylene oxide and polytetrahydrofuran; polystyrene, polycarbonate, polyurethane, chlorinated polyolefins, polyvinyl chloride, vinyl chloride/vinylidene copolymers, copolymers of vinylidene chloride with acrylonitrile, methyl methacrylate and vinyl acetate, polyvinyl acetate, copoly(ethylene/vinyl acetate), polymers such as polycaprolactam and poly (hexamethylenadipamide), and polyesters such as poly (ethylene glycol terephtalate) and poly(hexamethylene glycol succinate) and polyimide binder resins.

The polyimide binder resin in the present invention can either be a solvent soluble polyimide or a polymimide precursor, for example a poly(amic acid ester) compound, optionally having photopolymerizable side groups either attached to the backbone or to the ester groups in the molecule, or it can be, for example, a poly(amic acid) to which preferably an acrylate or methacrylate having at least one basic group in its molecule is added in solution, for example an aminoacrylate or aminomethacrylate.

Preferred is a photopolymerizable composition, comprising as binder polymer (e), a copolymer of methacrylate and methacrylic acid. Interesting further are polymeric binder components as described e.g. in JP 10-171119-A, in particular for use in color filters.

The unsaturated compounds (a) can also be used as a mixture with non-photopolymerizable, film-forming components. These may, for example, be physically drying polymers or solutions thereof in organic solvents, for instance nitrocellulose or cellulose acetobutyrate. They may also, however, be chemically and/or thermally curable (heat-curable) resins, examples being polyisocyanates, polyepoxides and melamine resins, as well as polyimide precursors. The use of heat-curable resins at the same time is important for use in systems known as hybrid systems, which in a first stage are photopolymerized and in a second stage are crosslinked by means of thermal aftertreatment.

In addition to the photoinitiator the photopolymerizable mixtures may include various additives (d). Examples of these are thermal inhibitors, which are intended to prevent premature polymerization, examples being hydroquinone, hydroquinone derivatives, p-methoxyphenol, β-naphthol or sterically hindered phenols, such as 2,6-di-tert-butyl-p- cresol In order to increase the stability on storage in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. To exclude atmospheric oxygen during the polymerization it is possible to add paraffin or similar wax-like substances which, being of inadequate solubility in the polymer, migrate to the surface in the beginning of polymerization and form a transparent surface layer which prevents the ingress of air. It is also possible to apply an oxygen-impermeable layer on top of the coating, for example poly(vinylalcohol-co-vinylacetate). Light stabilizers which can be added in a small quantity are UV absorbers, for example those of the hydroxyphenylbenzotriazole, hydroxyphenyl-benzophenone, oxalamide or hydroxyphenyl-s-triazine type. These compounds can be used individually or in mixtures, with or without sterically hindered amines (HALS).

Examples of such UV absorbers and light stabilizers are 1. 2-(2'-hydroxyphenyl)benzotriazoles for example 2-(2'-hydroxy-5'-methylphenyl)benzotriazole, 2-(3',5'-di-tert-butyl-2'-hydroxyphenyl)benzotriazole, 2-(5'-tert-butyl-2-hydro-xyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotrizole, 2-(2'-hydroxy-4'-octoxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)-benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethyl-hexyl-oxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)-benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazol-2-yl-phenol]; transesterification product of 2-[3'-tert-butyl-5'-(2-methoxycarbonylethyl)-2'-hydroxy-phenyl]-benzotriazole with polyethylene glycol 300; [R—CH$_2$CH$_2$—COO(CH$_2$)$_3$]$_2$— where R=3'-tert-butyl-4'-hydroxy-5'-2H-benzotrialzol-2-yl-phenyl.

2. 2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy derivative.

3. Esters of substituted or unsubstituted benzoicacids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, and 2-methyl-4,6-di-tert-butylphenyl 3,5-di-tert-butyl-4-hydroxybenzoate.

4. Acrylates, for example isooctyl or ethyl α-cyano-β,β-diphenyl acrylate, methyl α-carbomethoxycinnamate, butyl or methyl (α-cyano-β-methyl-p-methoxycinnamate, methyl α-carboxymethoxy-p-methoxycinnamate and N-(β-carbomethoxy-β-cyanovinyl)-2-methylindoline.

5. Sterically hindered amines, for example bis-(2,2,6,6-tetramethylpiperidyl) sebacate, bis-(2,2,6,6-tetramethylpiperidyl) succinate, bis-(1,2,2,6,6-pentamethylpiperidyl) sebacate, bis-(1,2,2,6,6-pentamethylpiperidyl) n-butyl-3,5-di-tert-butyl-4-hydroxybenzylmalonate, condensation product of 1-hydroxyethyl-2,2,6,6-tetramethyl-4-hydroxypiperidine and succinic acid, condensation product of N,N'-bis-(2,2,6,6-tetramethyl-4-piperidyl)hexa-methylenediamine and 4-tert-octylamino-2,6-dichloro-1,3,5-s-triazine, tris-(2,2,6,6-tetramethyl-4-piperidyl) nitrilotriacetate, tetrakis-(2,2,6,6-tetramethyl-4-piperidyl)-1,2,3,4-butane tetraoate, 1,1'-(1,2-ethandiyl)bis(3,3,5,5-tetramethyl-piperazinone), 4-benzoyl-2,2,6,6-tetramethylpiperidine, 4-stearyloxy-2,2,6,6-tetramethylpiperidine, bis-(1,2,2,6,6-pentamethylpiperidyl) 2-n-butyl-2-(2'-hydroxy-3,5-di-tert-butylbenzyl) malonate, 3-n-octyl-7,7,9,9-tetramethyl-1,3,8-triazaspiro-[4.5]decane-2,4-dione, bis-(1-octyloxy-2,2,6,6-tetramethylpiperidyl) sebacate, bis-(1-octyloxy-2,2,6,6-tetramethylpiperidyl) succinate, condensation product of N,N'-bis-(2,2,6,6-tetramethyl-4-piperidyl)hexamethylenediamine and 4-morpholino-2,6-dichloro-1,3,5-triazine, condensation product of 2-chloro-4,6-di-(4-n-butylamino-2,2,6,6-tetramethylpiperidyl)-1,3,5-triazine and 1,2-bis-(3-aminopropyl-amino)ethane, condensation product of 2-chloro-4,6-di-(4-n-butylamino-1,2,2,6,6-pentamethylpiperidyl)-1,3,5-triazine and 1,2-bis-(3-aminopropylamino)-ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione and 3-dodecyl-1-(1,2,2,6,6-penta-methyl-4-piperidyl)-pyrrolidine-2,5-dione. 6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'di-tert-butyloxanilide, 2-ethoxy-2'-ethyloxanilide, N,N'-bis-(3-dimethylaminopropyl)oxalamide, 2-ethoxy-5-tert-butyl-2'-ethyloxanilide and its mixture with 2-ethoxy-2'-ethyl-5,4'-di-tert-butyloxanilide, mixtures of o- and p-methoxy- and of o- and p-ethoxy-disubstituted oxanilides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis-(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxy-phenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-[2-hydroxy-4-(2-hydroxy-3-butyloxy-propyloxy)phenyl]-4,6bis(2,4-dimethylphenyl)-1,3,5-triazine, 2-[2-hydroxy-4-(2-hydroxy-3-octyloxy-propyloxy)phenyl]-4,6-bis(2,4-dimethylphenyl)-1,3,5-triazine, 2-[4-dodecyl/tridecyl-oxy-(2-hydroxypropyl)oxy-2-hydroxy-phenyl]-4,6-bis(2,4-dimethylphenyl)-1,3,5-triazine.

8. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythrityl diphosphite, tris-(2,4-di-tert-butylphenyl) phosphite, diisodecyl pentaerythrityl diphosphite, bis-(2,4-di-tert-butylphenyl) pentaerythrityl diphosphite, bis-(2,6-di-tert-butyl-4-methylphenyl) pentaerythrityl diphosphite, bis-isodecyloxy pentaerythrityl diphosphite, bis-(2,4-di-tert-butyl-6- methylphenyl) pentaerythrityl diphosphite, bis-(2,4,6-tri-tert-butylphenyl) pentaerythrityl diphosphite, tristearyl sorbityl triphosphite, tetrakis-(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyl-dibenzo[d,g]-1,3,2-dioxaphosphocine, bis-(2,4-di-tert-butyl-6-methylphenyl) methyl phosphite and bis(2,4-di-tert-butyl-6-methylphenyl) ethyl phosphite.

Further additives known in the art may be added as component (d), as for example flow improvers, adhesion promoters, such as vinyltrimethoxysilane, vinyltriethoxysilane vinyltris(2-methoxyethoxy)silane, N-(2-aminoethyl)-3-aminopropylmethyldimethoxysilane, N-(2-aminoethyl) 3 aminopropyltrimethoxysilane, 3-aminopropyltriethoxysilane, 3-glycidoxypropyltrimethoxysilane, 3-glycidoxypropylmethyldimethoxysilane, 2-(3,4-epoxycyclohexyl)ethyltrimethoxysilane, 3-chloropropylmethyldimethoxysilane, 3-chloropropyltrimethoxysilane, 3-methacryloxypropyltrimethoxysilane and 3-mercaptopropyltrimethoxysilane. Surfactants, aggregation preventers, antioxidants, photosensitizers, or fillers are further examples for additives (d).

To accelerate the photopolymerization it is possible to add amines, for example triethanolamine, N-methyldiethanolamine, p-dimethylaminobenzoate or Michler's ketone. The action of the amines can be intensified by the addition of aromatic ketones of the benzophenone type. Examples of amines which can be used as oxygen scavengers are substituted N,N-dialkylanilines, as are described in EP 339841. Other accelerators, coinitiators and autoxidizers are thiols, thioethers, disulfides, phosphonium salts, phosphine oxides or phosphines, as described, for example, in EP 438123, in GB 2180358 and in JP Kokai Hei 6-68309.

It is further possible to add chain transfer agents which are customary in the art to the compositions according to the invention. Examples are mercaptans, amines and benzothiazol.

Photopolymerization can also be accelerated by adding further photosensitizers or coinitiators (as component (d)) which shift or broaden the spectral sensitivity. These are, in particular, aromatic compounds, for example benzophenone and derivatives thereof, thioxanthone and derivatives thereof, anthraquinone and derivatives thereof, coumarin and phenothiazine and derivatives thereof, and also 3-(aroylmethylene)thiazolines, rhodanine, camphorquinone, but also eosine, rhodamine, erythrosine, xanthene, thioxanthene, acridine, e.g. 9-phenylacridine, 1,7-bis(9-acridinyl)heptane, 1,5-bis(9-acridinyl)pentane, cyanine and merocyanine dyes.

Specific examples of such compounds are

1. Thioxanthones

Thioxanthone, 2-isopropylthioxanthone, 2-chlorothioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)-thioxanthone, 4-butoxycarbonylthioxanthone, 3-butoxycarbonyl-7-methylthioxanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfurylthioxanthone, 3,4-di-[2-(2-methoxyethoxy)-ethoxycarbonyl]-thioxanthone, 1-ethoxycarbonyl-3-(1-methyl-1-morpholinoethyl)-thioxanthone, 2-methyl-6-dimethoxymethyl-thioxanthone, 2-methyl-6-(1,1-dimethoxybenzyl)-thioxathone, 2-morpholinomethylthioxanthone, 2-methyl-6-morpholinomethylthioxanthone, N-allylthioxanthone-3,4-dicarboximide, N-octylthioxanthone-3,4-dicarboximide, N-(1,1,3,3-tetramethylbutyl)-thioxanthone-3,4-dicarboximide, 1-phenoxythioxanthone, 6-ethoxycarbonyl-2-methoxythioxanthone, 6-ethoxycarbonyl-2-methylthioxanthone, thioxanthone-2-carboxylic acid polyethyleneglycol ester, 2-hydroxy-3-(3,4-dimethyl-9-oxo-9H-thioxanthon-2-yloxy)-N,N,N-trimethyl-1-propanaminium chloride;

2. Benzophenones benzophenone, 4-phenyl benzophenone, 4-methoxy benzophenone, 4,4'-dimethoxy benzophenone, 4,4'-dimethyl benzophenone, 4,4'-dichlorobenzophenone 4,4'-bis(dimethylamino)benzophenone, 4,4'-bis(diethylamino)benzophenone, 4-methyl benzophenone, 2,4,6-trimethylbenzophenone, 4-(4-methylthiophenyl)-benzophenone, 3,3'-dimethyl-4-methoxy benzophenone, methyl-2-benzoylbenzoate, 4-(2-hydroxyethylthio)-benzophenone, 4-(4-tolylthio) benzophenone, 4-benzoyl-N, N, N-trimethylbenzenemethanaminium chloride, 2-hydroxy-3-(4-benzoylphenoxy)-N,N,N-trimethyl-1-propanaminium chloride monohydrate, 4-(13-acryloyl-1,4,7,10,13-pentaoxatridecyl)-benzophenone, 4-benzoyl-N , N-dimethyl-N-[2-(1-oxo-2-propenyl)oxy]ethyl-benzenemethanaminium chloride;

3. Coumarins

Coumarin 1, Coumarin 2, Coumarin 6, Coumarin 7, Coumarin 30, Coumarin 102, Coumarin 106, Coumarin 138, Coumarin 152, Coumarin 153, Coumarin 307, Coumarin 314, Coumarin 314T, Coumarin 334, Coumarin 337, Coumarin 500, 3-benzoyl coumarin, 3-benzoyl-7-methoxycoumarin, 3-benzoyl-5,7-dimethoxycoumarin, 3-benzoyl-5,7-dipropoxycoumarin, 3-benzoyl-6,8-dichlorocoumarin, 3-benzoyl-6-chloro-coumarin, 3,3'-carbonyl-bis[5,7-di(propoxy)-coumarin], 3,3'-carbonyl-bis(7-methoxycoumarin), 3,3'-carbonyl-bis(7-diethylamino-coumarin), 3-isobutyroylcoumarin, 3-benzoyl-5,7-dimethoxy-coumarin, 3-benzoyl-5,7-diethoxy-coumarin, 3-benzoyl-5,7-dibutoxycoumarin, 3-benzoyl-5,7-di(methoxyethoxy)-coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 5,7-dimethoxy-3-(1-naphthoyl)-coumarin, 5,7-diethoxy-3-(1-naphthoyl)-coumarin, 3-benzoylbenzo[f]coumarin, 7-diethylamino-3-thienoylcoumarin, 3-(4-cyanobenzoyl)-5,7-dimethoxycoumarin, 3-(4-cyanobenzoyl)-5,7-dipropoxycoumarin, 7-dimethylamino-3-phenylcoumarin, 7-diethylamino-3-phenylcoumarin, the coumarin derivatives disclosed in JP 09-179299-A and JP 09-325209-A, for example 7-[{4-chloro-6-(diethylamino)-S-triazine-2-yl}amino]-3-phenylcoumarin;

4. 3-(aroylmethylene)-thiazolines 3-methyl-2-benzoylmethylene-β-naphthothiazoline, 3-methyl-2-benzoylmethylene-benzothiazoline, 3-ethyl-2-propionylmethylene-p-naphthothiazoline;

5. Rhodanines 4-dimethylaminobenzalrhodanine, 4-diethylaminobenzalrhodanine, 3-ethyl-5-(3-octyl-2-benzothiazolinylidene)-rhodanine, the rhodanine derivatives, formulae [1], [2], [7], disclosed in JP 08-305019A;

6. Other compounds acetophenone, 3-methoxyacetophenone, 4-phenylacetophenone, benzil, 4,4'-bis(dimethylamino)benzil, 2-acetylnaphthalene, 2-naphthaldehyde, dansyl acid derivatives, 9,10-anthraquinone, anthracene, pyrene, aminopyrene, perylene, phenanthrene, phenanthrenequinone, 9-fluorenone, dibenzosuberone, curcumin, xanthone, thiomichler's ketone, α-(4-dimethylaminobenzylidene) ketones, e.g. 2,5-bis(4-diethylaminobenzylidene)cyclopentanone, 2-(4-dimethylamino-benzylidene)-indan-1-one, 3-(4-dimethylamino-phenyl)-1-indan-5-yl-propenone, 3-phenylthiophthalimide, N-methyl-3,5-di(ethylthio)-phthalimide, N-methyl-3,5-di(ethylthio)-phthalimide, phenothiazine, methylphenothiazine, amines, e.g. N-phenylglycine, ethyl 4-dimethylaminobenzoate, butoxyethyl 4-dimethylaminobenzoate, 4-dimethylaminoacetophenone, triethanolamine, methyldiethanolamine, dimethylaminoethanol, 2-(dimethylamino)ethyl benzoate.

A photopolymerizable composition, comprising as photosensitizer (d) a compound selected from the group consisting of benzophenone and its derivatives, thioxanthone and its derivatives, anthraquinone and its derivatives, or coumarin derivatives is preferred.

The curing process can be assisted by adding photosensitizers, in particular, in compositions which are pigmented (for example with titanium dioxide), and also by adding a component which under thermal conditions forms free radicals, for example an azo compound such as 2,2'-azobis(4-methoxy-2,4-dimethylvaleronitrile), a triazene, diazo sulfide, pentazadiene or a peroxy compound, for instance a hydroperoxide or peroxycarbonate, for example t-butyl hydroperoxide, as described for example in EP 245639.

The compositions according to the invention may comprise as further additive (d) a photoreducable dye, e.g., xanthene-, benzoxanthene-, benzothioxanthene, thiazine-, pyronine-, porphyrine- or acridine dyes, and/or trihalogenmethyl compounds which can be cleaved by irradiation. Similar compositions are for example described in EP 445624.

Further customary additives, depending on the intended use, are optical brighteners, fillers, pigments, dyes, wetting agents, levelling assistants, dispersants and adhesion promoters, e.g. methacryloxypropyl trimethoxysilane.

In order to cure thick and pigmented coatings it is appropriate to add glass microspheres or pulverized glass fibres, as described for example in U.S. Pat. No. 5,013,768.

The choice of additive(s) (d) is made depending on the field of application and on properties required for this field. The additives described above are customary in the art and accordingly are added in amounts which are usual in the respective application.

The invention also provides compositions comprising as component (a) at least one ethylenically unsaturated photopolymerizable compound which is emulsified or dissolved in water. Many variants of such radiation-curable aqueous prepolymer dispersions are commercially available. A prepolymer dispersion is understood as being a dispersion of water and at least one prepolymer dispersed therein. The concentration of water in these systems is, for example, from 5 to 80% by weight, in particular from 30 to 60% by weight. The concentration of the radiation-curable prepolymer or prepolymer mixture is, for example, from 95 to 20% by weight, in particular from 70 to 40% by weight. In these compositions the sum of the percentages given for water and prepolymer is in each case 100, with auxiliaries and additives being added in varying quantities depending on the intended use. The radiation-curable, film-forming prepolymers which are dispersed in water and are often also dissolved are aqueous prepolymer dispersions of mono- or polyfunctional, ethylenically unsaturated prepolymers which are known per se, can be initiated by free radicals and have for example a content of from 0.01 to 1.0 mol of polymerizable double bonds per 100 g of prepolymer and an average molecular weight of, for example, at least 400, in particular from 500 to 10,000. Prepolymers with higher molecular weights, however, may also be considered depending on the intended application. Use is made, for example, of polyesters containing polymerizable C—C double bonds and having an acid number of not more than 10, of polyethers containing polymerizable C—C double bonds, of hydroxyl-containing reaction products of a polyepoxide, containing at least two epoxide groups per molecule, with at least one a,β-ethylenically unsaturated carboxylic acid, of polyurethane (meth)acrylates and of α-crylic copolymers which contain α,β-ethylenically unsaturated acrylic radicals, as are described in EP 12339. Mixtures of these prepolymers can likewise be used. Also suitable are the polymerizable prepolymers described in EP 33896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions, based on specific alkyl (meth)acrylate polymers, are described in EP 41125, and suitable waterdispersible, radiation-curable prepolymers of urethane acrylates can be found in DE 2936039.

Further additives which may be included in these radiation-curable aqueous prepolymer dispersions are dispersion auxiliaries, emulsifiers, antioxidants, e.g. 2,2-thiobis (4-methyl-6-t-butylphenol) or 2,6-di-t-butylphenol, light stabilizers, dyes, pigments, fillers, such as glass or alumina, for example talc, gypsum, silicic acid, rutile, carbon black, zinc oxide, iron oxides, reaction accelerators, levelling agents, lubricants, wetting agents, thickeners, flatting agents, antifoams and other auxiliaries customary in paint technology. Suitable dispersion auxiliaries are water-soluble organic compounds which are of high molecular mass and contain polar groups, examples being polyvinyl alcohols, polyvinylpyrrolidone or cellulose ethers. Emulsifiers which can be used are nonionic emulsifiers and, if desired, ionic emulsifiers as well.

In certain cases it may be of advantage to use mixtures of two or more of the novel photoinitiators. It is of course also possible to use mixtures with known photoinitiators (c), for example mixtures with camphor quinone, benzophenone, benzophenone derivatives, acetophenone, acetophenone derivatives, for example α-hydroxycycloalkyl phenyl ketones or 2-hydroxy-2-methyl-1-phenyl-propanone, dialkoxyacetophenones, α-hydroxy- or α-aminoacetophenones, e.g. (4-methylthiobenzoyl)-1-methyl-i-morpholinoethane, (4-morpholinobenzoyl)-1-benzyl-1-dimethylaminopropane, 4-aroyl-1,3-dioxolanes, benzoin alkyl ethers and benzil ketals, e.g. dimethyl benzil ketal, phenylglyoxalic esters and derivatives thereof, dimeric phenylglyoxalic esters, diacetyl, peresters, e,g. benzophenone tetracarboxylic peresters as described for example in EP 126541, monoacyl phosphine oxides, e.g. (2,4,6-trimethylbenzoyl)diphenylphosphine oxide, bisacylphosphine oxides, bis(2,6-dimethoxy-benzoyl)-(2,4,4-trimethyl-pentyl)phosphine oxide, bis(2,4,6-trimethylbenzoyl)-phenylphosphine oxide, bis(2,4,6-trimethylbenzoyl)-2,4-dipentoxyphenylphosphine oxide, trisacylphosphine oxides, halomethyltriazines, e.g. 2-[2-(4-methoxy-phenyl)-vinyl]-4,6-bis-trichloromethyl-[1,3,5]triazine, 2-(4-methoxy-phenyl)-4,6-bis-trichloromethyl-[1,3,5]triazine, 2-(3,4-dimethoxy-phenyl)-4,6-bis-trichloromethyl-[1,3,5]triazine, 2-methyl-4,6-bis-trichloromethyl-[1,3,5]triazine, 2-(p-N,N-di(ethoxycarbonylmethyl)aminophenyl)-4,6-di(trichloromethyl)-[1,3,5]triazine, 2-(4-methoxy-naphthyl)-4,6-bis-trichloromethyl-[1,3,5]triazine, 2-(1,3-benzodioxol-5-yl)-4,6-bis-trichloromethyl-[1,3,5]triazine, 2-[2-[4-(pentyloxy)phenyl]ethenyl]-4,6-bis-trichloromethyl-[1,3, 5-9 triazine, 2-[2-(3-methyl-2-furanyl)-ethenyl]-4,6-bis-trichloromethyl-[1,3,5]triazine, 2-[2-(5-methyl-2-furanyl)-ethenyl]-4,6-bis-trichloromethyl-[1,3,5]triazine, 2-[2-(2,4-dimethoxy-phenyl)-ethenyl]-4,6-bis-trichloromethyl-[1,3,5]triazine, 2-[2-(2-methoxy-phenyl)ethenyl]-4,6-bis-trichloromethyl-[-1,3,5]triazine, 2-[2-[4-isopropyloxy-phenyl]-ethenyl]-4,6-bis-trichloromethyl-[1,3,5]triazine, 2-[2-(3-chloro-4-methoxy-phenyl)ethenyl]-4,6-bis-trichloromethyl-[1,3,5]triazine, 2-[2-bromo-4-N,N-di(ethoxycarbonylmethyl)amino-phenyl]-4,6-bis-trichloromethyl-[1,3,5]triazine, 2-[2-chloro-4-N,N-di(ethoxycarbonylmethyl)amino-phenyl]-4,6-bis-trichloromethyl-[1,3,5]triazine, 2-[3-bromo-4-N, N-di(ethoxycarbonylmethyl)amino-phenyl]-4,6-bis-trichloromethyl-[1,3,5]triazine, 2-[3-chloro-4-N,N-di(ethoxycarbonylmethyl)amino-phenyl]-4,6-bis-trichloromethyl-[1,3,5]triazine, or other halomethyltriazines as described for example in G.Buhr, R. Dammel and C. Lindley Polym. Mater. Sci. Eng. 61,269 (1989), and EP 0262788; halomethyl-oxazol photoinitiators, such as described in U.S. Pat. Nos. 4,371,606 and 4,371,607; 1,2-disulfones, such as described in E. A. Bartmann, Synthesis 5, 490 (1993); hexaarylbisimidazole, and hexaarylbisimidazole/coinitiators systems, e.g. ortho-chlorohexaphenyl-bisimidazole combined with 2-mercaptobenzthiazole, ferrocenium compounds, or titanocenes, e.g. bis(cyclopentadienyl)-bis(2,6-difluoro-3-pyrryl-phenyl)titanium. Where the novel photoinitiator systems are employed in hybrid systems, use is made, in addition to the novel free-radical hardeners, of cationic photoinitiators, of peroxide compounds, such as benzoyl peroxide (other suitable peroxides are described in U.S. Pat. No. 4,950,581 column 19, lines 17–25), of aromatic sulfonium-, phosphonium- or iodonium salts as described for example in U.S. Pat. No. 4,950,581, column 18, line 60 to column 19, line 10 or cyclopentadienyl-arene-iron(II) complex salts, for example ($\eta^6$-iso-propylbenzene)($\eta^5$-cyclopentadienyl)-iron(II) hexafluorophosphate, as well as oxime sulfonic acid esters, as are, for example described in EP 780729. Also pyridinium and (iso)quinolinium salts as described e.g. in EP 497531 and EP 441232 may be used in combination with the new photoinitiators.

Subject of the invention are compositions comprising besides the compound of formula I, II, III or IV at least one α-aminoketone, in particular (4-methylthiobenzoyl)-1-methyl-1-morpholinoethane.

The photopolymerizable compositions generally comprise 0.005 to 25% by weight, preferably 0.01 to 10% by weight, in particular 0.01 to 5% by weight of the photoinitiator, based on the solid composition. The amount refers to the sum of all photoinitiators added, if mixtures of initiators are employed. Accordingly, the amount either refers to the photoinitiator (b) or the photoinitiators (b)+(c).

The photopolymerizable compositions can be used for various purposes, for example as printing ink, as a clear finish, as a white finish, for example for wood or metal, as powder coating, as a coating material, inter alia for paper, wood, metal or plastic, as a daylight-curable coating for the marking of buildings and roadmarking, for photographic reproduction techniques, for holographic recording materials, for image recording techniques or to produce printing plates which can be developed with organic solvents or with aqueous alkalis, for producing masks for screen printing, as dental filling compositions, as adhesives, as pressure-sensitive adhesives, as laminating resins, as etch resists, electroplating resists, or permanent resists, both liquid and dry films, as photostructurable dielectric and as solder masks for printed circuit boards and electronic circuits, as resists to manufacture color filters for a variety of display applications or to generate structures in the manufacturing process of plasma-display panels and electroluminescence displays, (as for example described in U.S. Pat. No. 5,853,446, EP 863534, JP 09-244230-A, JP 10-62980-A, JP 08-171863-A, U.S. Pat. No. 5,840,465, EP 855731, JP 05-271576-A, JP 05-67405-A) for the production of optical switches, optical lattices (interference lattice), light circuits, for producing three-dimensional articles by mass curing (UV curing in transparent moulds) or by the stereolithography technique, as is described, for example, in U.S. Pat. No. 4,575,330, to produce composite materials (for example styrenic polyesters, which may, if desired, contain glass fibres and/or other fibres and other auxiliaries) and other thick-layered compositions, for coating or sealing electronic components and integrated circuits, or as coatings for optical fibres, or for producing optical lenses, e.g. contact lenses or Fresnel lenses. The compositions according to the invention are further suitable for the production of medical equipment, auxiliaries or implants. Further, the compositions according to the invention are suitable for the preparation of gels with thermotropic properties, as for example described in DE 19700064 and EP 678534.

The novel photoinitiators may additionally be employed as initiators for emulsion polymerizations, pearl polymerizations or suspension polymerizations, as polymerization initiators for fixing ordered states of liquid-crystalline monomers and oligomers, or as initiators for fixing dyes on organic materials.

In coating materials, use is frequently made of mixtures of a prepolymer with polyunsaturated monomers, which may additionally include a monounsaturated monomer as well. It is the prepolymer here which primarily dictates the properties of the coating film, and by varying it the skilled worker is able to influence the properties of the cured film. The polyunsaturated monomer functions as a crosslinking agent which renders the film insoluble. The monounsaturated monomer functions as a reactive diluent, which is used to reduce the viscosity without the need to employ a solvent. Unsaturated polyester resins are usually used in two-component systems together with a monounsaturated monomer, preferably with styrene. For photoresists, specific one-component systems are often used, for example polymaleimides, polychalcones or polyimides, as described in DE 2308830.

The novel photoinitiators and mixtures thereof can also be used for the polymerization of radiation-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (for example methyl methylacrylamidoglycolate) and a novel free-radical photoinitiator, such formulations being as described, for example, in the paper "Radiation Curing of Powder Coating", Conference Proceedings, Radtech Europe 1993 by M. Wittig and Th. Gohmann. The powder coatings can also contain binders, as are described, for example, in DE 4228514 and in EP 636669. Free-radically UV-curable powder coatings can also be formulated by mixing unsaturated polyester resins with solid acrylates, methacrylates or vinyl ethers and with a novel photoinitiator (or photoinitiator mixture). The powder coatings may also comprise binders as are described, for example, in DE 4228514 and in EP 636669. The UV-curable powder coatings may additionally comprise white or coloured pigments. For example, preferably rutiletitanium dioxide can be employed in concentrations of up to 50% by weight in order to give a cured powder coating of good hiding power. The procedure normally comprises electrostatic or tribostatic spraying of the powder onto the substrate, for example metal or wood, melting of the powder by heating, and, after a smooth film has formed, radiation-curing of the coating with ultraviolet and/or visible light, using for example medium-pressure mercury lamps, metal halide lamps or xenon lamps. A particular advantage of the radiation-curable powder coatings over their heat-curable counterparts is that the flow time after melting the powder particles can be delayed in order to ensure the formation of a smooth, high-gloss coating. In contrast to heat-curable systems, radiation-curable powder coatings can be formulated to melt at lower temperatures without the unwanted effect of shortening their lifetime. For this reason, they are also suitable as coatings for heat-sensitive substrates, for example wood or plastics. In addition to the novel photoinitiator systems, the powder coating formulations may also include UV absorbers. Appropriate examples are listed above in sections 1.–8.

The novel photocurable compositions are suitable, for example, as coating materials for substrates of all kinds, for example wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which it is intended to apply a protective layer or, by means of imagewise exposure, to generate an image.

Coating of the substrates can be carried out by applying to the substrate a liquid composition, a solution or a suspension. The choice of solvents and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate, ethyl 3-ethoxypropionate, 2-methoxypropylacetate, methyl-3-methoxypropionate, 2-heptanone, 2-pentanone, and ethyl lactate. The solution is applied uniformly to a substrate by means of known coating techniques, for example by spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, or a glass substrate by transferring the layer via lamination. The quantity applied (coat thickness) and the nature of the substrate (layer support) are dependent on the desired field of application. The range of coat thicknesses generally comprises values from about 0.1 $\mu$m to more than 100 $\mu$m, for example 0.1 $\mu$m to 1 cm, preferably 1 $\mu$m to 1000 $\mu$m.

The novel radiation-sensitive compositions further find application as negative resists, having a very high sensitivity to light and being able to be developed in an aqueous alkaline medium without swelling. They are suitable as photoresists for electronics like electroplating resist, etch resist, both liquid and dry films, solder resist, as resists to manufacture color filters for a variety of display applications or to generate structures in the manufacturing process of plasma-display panels and electroluminescence displays, the production of printing plates, such as offset printing plates or screen printing plates, for the production of printing forms for relief printing, planographic printing, photogravure or of screen printing forms, for the production of relief copies, for example for the production of texts in braille, for the production of stamps, for use in chemical milling or as a microresist in the production of integrated circuits. The compositions further may be used as photopatternable dielectric layer or coating, encapsulating material and isolating coating in the production of computer chips, printed boards and other electric or electronic components. The possible layer supports, and the processing conditions of the coating substrates, are just as varied.

Because the photocurable compositions according to the invention have a good thermal stability and are sufficiently resistant to inhibition by oxygen, they are particularly suitable for the production of color filters or color mosaic systems, such as described, for example, in EP 320 264. Color filters usually are employed in the manufacturing of LCD displays, projection systems and image sensors. The color filters can be used, for example, for display and image scanner in television receivers, video monitors or computers, in flat panel display technology etc.

In a process to form a color filter, the coloring matters, dyes and pigments of red, green and blue colors are added to the light-sensitive resin composition of the present invention to provide a light-sensitive resin composition layer of any color on a transparent substrate, and then it is subjected to the processes such as exposing, developing, and according to necessity, heating to form an image.

The development is carried out by washing out the areas which were not polymerized with a suitable alkali developing solution. This process is repeated to form the image having plural colors.

In the light-sensitive resin composition of the present invention, with a process in which at least one or more picture elements are formed on a transparent substrate and then an exposure is given from a side of the transparent substrate, on which the above picture elements are not formed, the above picture elements can be utilized as a light-shielding mask. In this case, for example, in the case where an overall exposure is given, a position adjustment of a mask gets unnecessary and a concern on a position slippage thereof is removed. And, it is possible to cure all of the part on which the above picture elements are not formed. Further, in this case, it is possible as well to develop and remove a part of the portion on which the above picture elements are not formed by using partially a light-shielding mask.

Since in either case, no gap is formed between the picture elements which are formed formerly and those which are formed later, the composition of the present invention is suitable for, for example, a forming material for a color filter. To be concrete, the coloring matters, dyes and pigments of red, green and blue colors are added to the light-sensitive resin composition of the present invention, and the processes for forming an image are repeated to form the picture elements of red, green and blue colors. Then, the light-sensitive resin composition to which, for example, the black coloring materials, dyes and pigments are added is provided on an overall face. An overall exposure (or a partial exposure via a light-shielding mask) can be provided thereon to form the picture elements of a black color all over the spaces (or all but a partial region of the light-shielding mask) between the picture elements of red, green and blue colors.

In addition to a process in which the light-sensitive resin composition is coated on a substrate and dried, the light-sensitive resin composition of the present invention can be used as well for a layer transfer material. That is, the light-sensitive resin composition is layer-wise provided directly on a temporary support, preferably on a polyethylene terephthalate film, or on a polyethylene terephthalate film on which an oxygen-shielding layer and a peeling layer or the peeling layer and the oxygen-shielding layer are provided. Usually, a removable cover sheet made of a synthetic resin is laminated thereon for a protection in handling. Further, there can be applied as well a layer structure in which an alkali soluble thermoplastic resin layer and an intermediate layer are provided on a temporary support and further a light-sensitive resin composition layer is provided thereon (JP-A-5-173320).

The above cover sheet is removed in use and the light-sensitive resin composition layer is laminated on a permanent support. Subsequently, peeling is carried out between those layer and a temporary support when an oxygen-shielding layer and a peeling layer are provided, between the peeling layer and the oxygen-shielding layer when the peeling layer and the oxygen-shielding layer are provided, and between the temporary support and the light-sensitive resin composition layer when either the peeling layer or the oxygen-shielding layer is not provided, and the temporary support is removed.

A metal support, glass, ceramics, and a synthetic resin film can be used as a support for a color filter. Glass and a synthetic resin film which is transparent and have an excellent dimension stability is particularly preferred.

The thickness of the light-sensitive resin composition layer is usually 0.1 to 50 micrometers, in particular 1 to 5 micrometers.

A diluted aqueous solution of an alkaline substance is used as a developing solution for the light-sensitive resin composition of the present invention, and further a solution prepared by adding a small amount of a water-miscible organic solvent thereto is included as well.

Examples of suitable alkaline materials include alkali metal hydroxides (for example, sodium hydroxide and potassium hydroxide), alkali metal carbonates (for example, sodium carbonate and potassium carbonate), alkali metal bicarbonates (for example, sodium bicarbonate and potassium bicarbonate), alkali metal silicates (for example, sodium silicate and potassium silicate), alkali metal metasilicates (for example, sodium metasilicate and potassium metasilicate), triethanolamine, diethanolamine, monoethanolamine, morpholine, tetraalkylammonium hydroxides (for example, tetramethylammonium hydroxide), or trisodium phosphate. The concetration of the alkaline substance is 0.01 to 30 weight %, and pH is preferably 8 to 14.

Suitable organic solvents which are miscible with water include methanol, ethanol, 2-propanol, 1-propanol, butanol, diacetonealcohol, ethylene glycol monomethyl ether, ethylene glycol monoethyl ether, ethylene glycol mono-n-buthyl ether, benzyl alcohol, acetone, methyl ethyl ketone, cyclohexanone, epsilon-caprolactone, gamma-butylolactone, dimethylformamide, dimethylacetoamide, hexamethylphosphoramide, ethyl lactate, methyl lactate, epsilon-caprolactam, and N-methyl-pyrrolidone. The concentration of the organic solvent which is miscible with water is 0.1 to 30 weight %.

Further, a publicly known surface active agent can be added. The concentration of the surface active agent is preferably 0.001 to 10 weight %.

The developing solution can be used in either form of a bath solution or a spraying solution. In order to remove the non-cured portion of the light-sensitive resin composition layer, there can be combined the methods such as rubbing with a rotary brush and rubbing with a wet sponge. Usually, the temperature of the developing solution is preferably at and around room temperature to 40° C. The developing time is changeable according to the specific kind of the light-sensitive resin composition, the alkalinity and temperature of the developing solution, and the kind and concentration of the organic solvent in the case where it is added. Usually, it is 10 seconds to 2 minutes. It is possible to put a rinsing step after the development processing.

A final heat treatment is preferably carried out after the development processing. Accordingly, a support having a layer which is photopolymerized by exposing (hereinafter referred to as a photocured layer) is heated in an electric furnace and a drier, or the photocured layer is irradiated with an infrared lamp or heated on a hot plate. The heating temperature and time depend on the composition used and the thickness of the formed layer. In general, heating is preferably applied at about 120° C. to about 250° C., for about 5 to about 60 minutes.

The light-sensitive composition of the present invention can suitably be used for forming a color filter but will not be limited to this application. It is useful as well for a recording material, a display, a display element, a paint, and a printing ink.

Because the photocurable compositions according to the invention have a good thermal stability and are sufficiently resistant to inhibition by oxygen, they are particularly suitable for the production of color filters or color mosaic systems, such as described, for example, in EP 320 264. Color filters usually are employed in the manufacturing of LCD displays, projection systems and image sensors. The color filters usually are prepared by forming red, green and blue pixels and a black matrix on a glass substrate. In these processes photocurable compositions according to the invention can be employed. A particularly preferred method of use comprises the coating of the substrate with the composition of the invention, drying of the coating with a short heat treatment, patternwise exposure of the coating to actinic radiation and subsequent development of the pattern in an aqueous alkaline developer solution and optionally a heat treatment. Thus, by subsequently applying a red, green and blue pigmented coating, in any desired order, on top of each other with this process a color filter layer with red, green and blue color pixels can be produced. The color filters can be used, for example, for display and image scanner in television receivers, video monitors or computers, in flat panel display technology etc.

The pigment which can be comprised in the composition according to the present invention, including a pigmented color filter resist composition, is preferably a processed pigment, for example a powdery or pasty product prepared by finely dispersing a pigment into at least one resin selected from the group consisting of acrylic resin, vinyl chloride-vinyl acetate copolymer, maleic acid resin and ethyl cellulose resin.

The red pigment comprises, for example, an anthraquinone type pigment alone, a perylene type pigment alone, or a mixture consisting of at least one of them and a disazo type yellow pigment or an isoindoline type yellow pigment, in particular C. I. Pigment Red 177 alone, C. I. Pigment Red 155 alone or a mixture consisting of at least one member of C. I. Pigment Red 177, C. I. Pigment Red 155 and C. I. Pigment Yellow 83 or C. I. Pigment Yellow 139 ("C.I." refers to the Color Index, known to the person skilled in the art and publicly available). Further suitable examples for the pigment are C.I. Pigment Red 105, 144, 149, 176, 177, 185, 202, 209, 214, 222, 242, 254, 255, 264, 272 and C.I. Pigment Yellow 24, 31, 53, 83, 93, 95, 109, 110, 128, 129, 138, 139, 166 and C.I. Pigment Orange 43.

The green pigment comprises for instance a halogenated phthalocyanine type pigment alone or its mixture with a disazo type yellow pigment or an isoindoline type yellow pigment, in particular C. I. Pigment Green 7 alone, C. I. Pigment Green 36 alone, C. I. Pigment Green 37 alone or a mixture consisting of at least one member of C. I. Pigment Green 7, C. I. Pigment Green 36, C. I. Pigment Green 37, C.I. Pigment Green 136 and C. I. Pigment Yellow 83 or C. I. Pigment Yellow 139. Other suitable green pigments are C.I. Pigment Green 15 and 25.

Examples for suitable blue pigments are phthalocyanine type pigments, used either alone or in combination with an dioxazine type violet pigment, for instance, a combination of C. I. Pigment Blue 15:3 and C. I. Pigment Violet 23. Further examples for blue pigments are such of C.I. Blue 15:3, 15:4, 15:6, 16 and 60, i.e. Phthalocyanine Cl Pigment Blue 15:3, or Phthalocyanine C.I. Pigment Blue 15:6. Other suitable pigments are such of C.I. Pigment Blue 22, 28, C.I. Pigment Violet 14,19, 23, 29, 32, 37, 177 and C.I. Orange 73.

The pigment of the black matrix photopolymeric composition preferably comprises at least one member selected from the group consisting of carbon, titanium black and iron oxide. However, a mixture of other pigments which, in total, give the black appearance, can also be used. For example, also C.I. Pigment Black 1 and 7 can be used alone or in combination.

For any color, combinations of more than two pigments can also be used. Especially suitable in color filter applications are powdery processed pigments prepared by finely dispersing the above mentioned pigments into a resin.

The concentration of the pigment in the total solid component (pigments of various colors and resin) is for example in the range of 5% to 80% by weight, in particular in the range of 20% to 40% by weight.

The pigments in the color filter resist composition have preferably a mean particle diameter smaller than the wavelength of visible light (400 nm to 700 nm). Particularly preferred is a mean pigment diameter of <100 nm.

The concentration of the pigment in the total solid component in each color is in the range from 5% by weight to 80% by weight, preferably in the range of 20% to 45%.

If necessary, the pigments may be stabilized in the photosensitive composition by pretreatment of the pigments with a dispersant to improve the dispersion stability of the pigment in the liquid formulation.

Examples for color filter resists, the composition of such resists and the processing conditions are given by T. Kudo et al., Jpn. J. Appl. Phys. Vol. 37 (1998) 3594; T. Kudo et al., J. Photopolym. Sci. Technol. Vol 9 (1996) 109; K. Kobayashi, Solid State Technol. November 1992, p. S15–S18; U.S. Pat. Nos. 5,368,976; 5,800,952; 5,882,843; 5,879,855; 5,866,298; 5,863,678; JP 06-230212-A; EP 320264; JP 09-269410-A; JP 10-221843-A; JP 01-090516-A; JP 10-171119-A, U.S. Pat. Nos. 5821016, 5,847,015, 5,882,843, 5,719,008, EP 881541, or EP 902327.

The photoinitiators of the present invention can be used in color filter resists, for example, such as those given as examples above, or can partially or fully replace the known photoinitiators in such resists. It is understood by a person skilled in the art that the use of the new photoinitiators of the present invention is not limited to the specific binder resins, crosslinkers and formulations of the color filter resist examples given hereinbefore but can be used in conjunction with any radically polymerizable component in combination with a dye or color pigment or latent pigment to form a photosensitive color filter ink or color filter resist.

Accordingly, subject of the invention also is a color filter prepared by providing red, green and blue (RGB) colour elements and, optionally a black matrix, all comprising a photosensitive resin and a pigment on a transparent substrate and providing a transparent electrode either on the surface of the substrate or on the surface of the color filter layer, wherein said photosensitive resin comprises a polyfunctional acrylate monomer, an organic polymer binder and a photopolymerization initiator of formula I, II, III or IV as described above. The monomer and binder components, as well as suitable pigments are as described above. In the manufacture of color filters the transparent electrode layer can either be applied on the surface of the transparent substrate or can be provided on the surface of the red, green and blue picture elements and the black matrix. The transparent substrate is for example a glass substrate which can additionally have an electrode layer on its surface. It is preferred to apply a black matrix between the color areas of different color in order to improve the contrast of a color filter.

Instead of forming a black matrix using a photosensitive composition and patterning the black photosensitive composition photolithographically by patternwise exposure (i.e. through a suitable mask) to form the black pattern separating the red green and blue coloured areas on the tranparent substrate it is alternatively possible to use an inorganic black matrix. Such inorganic black matrix can be formed from deposited (i.e. sputtered) metal (i.e. chromium) film on the transparent substrate by a suitable imaging process, for example utilizing photolithographic patterning by means of an etch resist, etching the inorganic layer in the areas not protected by the etch resist and then removing the remaining etch resist.

There are different methods known how and at which step in the color filter manufacturing process the black matrix can be applied. It can either be applied directly on the transparent substrate prior to formation of the red, green and blue (RGB) colour filter as already mentioned above, or it can be applied after the RGB colour filter is formed on the substrate.

In a different embodiment of a color filter for a liqid crystal display, according to U.S. Pat. No. 5,626,796, the black matrix can also be applied on the substrate opposite to the RGB color filter element-carrying substrate, which is separated from the former by a liquid crystal layer.

If the transparent electrode layer is deposited after applying the RGB color filter elements and—optionally—the black matrix, an additional overcoat film as aprotective layer can be applied on the color filter layer prior to deposition of the electrode layer, for example, as described in U.S. Pat. No. 5,650,263.

It is obvious to those skilled in the art, that the photosensitive compositions of the present invention can be used for generating red, green and blue color pixels and a black matrix, for the manufacture of a color filter, regardless of the above described differences in processing, regardless, of additional layers which can be applied and regardless of differences in the design of the color filter. The use of a composition according to the present invention to form colored elements shall not be regarded as limited by different designs and manufacturing processes of such color filters.

Preferably, the organic polymer binder in the color filter resist composition comprises an alkali soluble copolymer comprising, as addition polymerizable monomer units, at least an unsaturated organic acid compound such as acrylic acid, methacrylic acid and the like. It is preferred to use as a further co-monomer for the polymer binder an unsaturated organic acid ester compound such as methyl acrylate, ethyl (meth)acrylate, benzyl (meth)acrylate, styrene and the like to balance properties such as alkaline solubility, adhesion rigidity, chemical resistance etc.

The organic polymer binder can either be a random co-polymer or a block-co-polymer, for example, such as described in U.S. Pat. No. 5,368,976.

Preferably, the color filter resist composition according to the present invention contains additionally at least one addition polymerizable monomeric compound.

For example, the following compounds can be used singly or in combination with the other monomers as the addition-polymerizable monomer having an ethylenically unsaturated double bond used in the present invention. Specifically, they include t-butyl(meth)acrylate, ethylene glycol di(meth) acrylate, 2-hydroxypropyl (meth)acrylate, triethylene glycol di(meth)acrylate, trimethylolpropane tri(meth)acrylate, 2-ethyl-2-butylpropanediol di(meth)acrylate, pentaerythritol tri(meth)acrylate, pentaerythritol tetra(meth)acrylate, dipentaerythritol hexa(meth)acrylate, dipentaerythritol penta (meth)acrylate, polyoxyethylated trimethylolpropane tri (meth)acrylate, tris(2-(meth)acryloyloxyethyl)isocyanurate, 1,4-diisopropenyl-benzene, 1,4-dihydroxybenzene (meth) acrylate, decamethylene glycol di(meth)acrylate, styrene, diallyl fumarate, triallyl trimellitate, lauryl (meth)acrylate, (meth)acrylamide, and xylenebis(meth)acrylamide. Further, there can be used a reaction product of a compound having a hydroxyl group, such as 2-hydroxyethyl (meth)acrylate, 2-hydroxypropyl (meth)acrylate, and polyethylene glycol mono(meth)acrylate with diisocyanate such as hexamethylenediisocyanate, toluenediisocyanate, and xylenediisocyanate. Particularly preferred are pentaerythritol tetraacrylate, dipentaerythritol hexaacrylate, dipentaerythritol pentaacrylate, and tris(2-acyloyloxyethyl)-isocyanurate.

In a color filter resist composition the whole amount of the monomers contained in the photopolymerizable composition is preferably 5 to 80% by weight, in particular 10 to 70% by weight based on the whole components of the composition.

As the binder used in the color filter resist composition, which is soluble in an alkaline aqueous solution and insoluble in water, for example, a homopolymer of a polymerizable compound having one or more acid groups and one or more polymerizable unsaturated bonds in the molecule, or a copolymer of two or more kinds thereof, and a copolymer of one or more polymerizable compounds having one or more unsaturated bonds copolymerizable with these compounds and containing no acid group, can be used. Such compounds can be obtained by copolymerizing one or more kinds of a low molecular compound having one or more acid groups and one or more polymerizable unsaturated bonds in the molecule with one or more polymerizable compounds having one or more unsaturated bonds copolymerizable with these compounds and containing no acid group. Examples of acids groups are, a —COOH group, a —SO$_3$H group, a —SO$_2$NHCO— group, a phenolic hydroxy group, a —SO$_2$NH— group, and a —CO—NH—CO— group. Among those, a high molecular compound having a —COOH group is particularly preferred.

Examples of polymerizable compounds having one or more acid group and one or more polymerizable unsaturated bond in the molecule include the following compounds: Acrylic acid, methacrylic acid, itaconic acid, crotonic acid, maleic acid, vinylbenzoic acid, and cinnamic acid are examples of the polymerizable compounds having one or more —COOH groups and one or more polymerizable unsaturated bonds in a molecule. Vinylbenzenesulfonic acid and 2-(meth)acrylamide-2-methylpropanesulfonic acid are examples of the polymerizable compounds having one or more —SO$_3$H groups and one or more polymerizable unsaturated bonds. N-methylsulfonyl (meth)acrylamide, N-ethylsulfonyl (meth)acrylamide, N-phenylsulfonyl (meth)acrylamide, and N-(p-methylphenylsulfonyl) (meth) acrylamide are examples of the polymerizable compounds having one or more —SO$_2$NHCO— groups and one or more polymerizable unsaturated bonds.

Examples of polymerizable compounds having one or more phenolic hydroxy groups and one or more polymerizable unsaturated bonds in a molecule include hydroxyphenyl (meth)acrylamide, dihydroxyphenyl (meth)acrylamide, hydroxyphenyl-carbonyloxyethyl (meth)acrylate, hydroxyphenyloxyethyl (meth)acrylate, hydroxyphenylthioethyl (meth)acrylate, dihydroxyphenylcarbonyloxyethyl (meth) acrylate, dihydroxyphenyloxyethyl (meth)acrylate, and dihydroxy-phenylthioethyl (meth)acrylate.

Examples of the polymerizable compound having one or more —SO$_2$NH— groups and one or more polymerizable unsaturated bonds in the molecule include compounds represented by formula (a) or (b):

  (a)

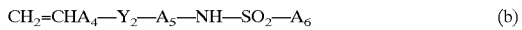  (b)

wherein Y$_1$ and Y$_2$ each represents —COO—, —CONA$_7$—, or a single bond; A$_1$ and A$_4$ each represents H or CH$_3$; A$_2$ and A$_5$ each represents C$_1$–C$_{12}$alkylene optionally having a substituent, cycloalkylene, arylene, or aralkylene, or C$_2$–C$_{12}$alkylene into which an ether group and a thioether group are inserted, cycloalkylene, arylene, or aralkylene; A$_3$ and A$_6$ each represents H, C$_1$–C$_{12}$alkyl optionally having a substituent, a cycloalkyl group, an aryl group, or an aralkyl group; and A$_7$ represents H, C$_1$–C$_{12}$alkyl optionally having a substituent, a cycloalkyl group, an aryl group, or an aralkyl group.

The polymerizable compounds having one or more —CO—NH—CO— group and one or more polymerizable unsaturated bond include maleimide and N-acryloyl-acrylamide. These polymerizable compounds become the high molecular compounds comprising a —CO—NH—CO— group, in which a ring is formed together with a primary chain by polymerization. Further, a methacrylic acid derivative and an acrylic acid derivative each having a —CO—NH—CO— group can be used as well. Such methacrylic acid derivatives and the acrylic acid derivatives include, for example, a methacrylamide derivative such as N-acetylmethacrylamide, N-propionylmethacrylamide, N-butanoylmethacrylamide, N-pentanoylmethacrylamide, N-decanoylmethacrylamide, N-dodecanoylmethacrylamide, N-benzoylmethacrylamide, N-(p-methylbenzoyl)methacrylamide, N-(p-chlorobenzoyl)methacrylamide, N-(naphthylcarbonyl)methacrylamide, N-(phenylacetyl)-methacrylamide, and 4-methacryloylaminophthalimide, and an acrylamide derivative having the same substituent as these. These polymerizable compounds polymerize to be compounds having a —CO—NH—CO— group in a side chain.

Examples of polymerizable compounds having one or more polymerizable unsaturated bond and containing no acid group include a compound having a polymerizable unsaturated bond, selected from (meth)acrylates, (meth) acrylamides, an acrylic compound, vinyl ethers, vinyl esters, styrenes, and crotonates, and specifically, include (meth) acrylates such as alkyl (meth)acrylate or substituted alkyl (meth)acrylate (for example, methyl (meth)acrylate, ethyl (meth)acrylate, propyl (meth)acrylate, isopropyl (meth) acrylate, butyl (meth)acrylate, amyl (meth)acrylate, hexyl (meth)acrylate, cyclohexyl (meth)acrylate, ethylhexyl (meth)acrylate, octyl (meth)acrylate, t-octyl (meth)acrylate, chloro-ethyl (meth)acrylate, allyl (meth)acrylate, 2-hydroxy-ethyl (meth)acrylate, 2-hydroxypropyl (meth) acrylate, 4-hydroxybutyl (meth)acrylate, 2,2-dimethyl-3-hydroxy-propyl (meth)acrylate, 5-hydroxypentyl (meth) acrylate, trimethylolpropane mono (meth)acrylate, pentaerythritol mono (meth)acrylate, benzyl (meth)acrylate, methoxy-benzyl (meth)acrylate, chlorobenzyl (meth) acrylate, furfuryl (meth)acrylate, tetrahydrofurfuryl (meth) acrylate, phenoxyethyl (meth)acrylate, and aryl (meth) acrylate (for example, phenyl (meth)acrylate, cresyl (meth) acrylate, and naphthyl (meth)acrylate); (meth)acrylamides such as (meth)acryl-amide, N-alkyl(meth)acrylamide (the alkyl group includes, for example, methyl, ethyl, propyl, butyl, t-butyl, heptyl, octyl, ethylhexyl, cyclohexyl, hydroxyethyl, and benzyl), N-aryl(meth)acrylamide (the aryl group includes, for example, phenyl, tolyl, nitrophenyl, naphthyl, and hydroxyphenyl), N,N-dialkyl(meth)acrylamide (the alkyl group includes, for example, methyl, ethyl, butyl, isobutyl, ethylhexyl, and cyclohexyl), N,N-diaryl (meth)acrylamide (the aryl group includes, for example, phenyl), N-methyl-N-phenyl (meth)acryl-amide, N-hydroxyethyl-N-methyl (meth)acrylamide, N-2-acetoamidethyl-N-acetyl(meth)acrylamide, N-(phenylsulfonyl)(meth)acrylamide, and N-(p-methylphenylsulfonyl)(meth)acrylamide;

an allyl compound such as allyl esters (for example, allyl acetate, allyl caproate, allyl caprylate, allyl laurate, allyl palmitate, allyl stearate, allyl benzoate, allyl acetoacetate, and allyl lactate), and allyloxyethanol; vinyl ethers such as alkyl vinyl ether (the alkyl group includes, for example, hexyl, octyl, decyl, ethylhexyl, methoxyethyl, ethoxyethyl, chloroethyl, 1-methyl-2,2-dimethylpropyl, 2-ethylbutyl, hydroxyethyl, hydroxyethoxyethyl, dimethylaminoethyl, diethylamino-ethyl, butylamino-ethyl, benzyl, and tetrahydrofurfuryl), and vinyl aryl ether (the aryl group includes, for example, phenyl, tolyl, chlorophenyl, 2,4-dichloro-phenyl, naphthyl, and anthranyl);

vinyl esters such as vinyl butylate, vinyl isobutylate, vinyl trimethylacetate, vinyl diethyl-acetate, vinyl barate, vinyl caproate, vinyl chloro-acetate, vinyl dichloroacetate, vinyl methoxyacetate, vinyl butoxyacetate, vinyl phenylacetate, vinyl aceto-acetate, vinyl lactate, vinyl-b-phenylbutylate, vinyl cyclohexylcarboxylate, vinyl benzoate, vinyl salicylate, vinyl chlorobenzoate, vinyl tetrachlorobenzoate, and vinyl naphthoate;

styrenes such as styrene, alkylstyrene (for example, methylstyrene, dimethylstyrene, trimethyl-styrene, ethylstyrene, diethylstyrene, isopropylstyrene, butylstyrene, hexylstyrene, cyclohexylstyrene, decylstyrene, benzylstyrene, chloromethylstyrene, trifluoromethylstyrene, ethoxymethylstyrene, and acetoxymethyl-styrene), alkoxystyrene (for example, methoxystyrene, 4-methoxy-3-methylstyrene, and dimethoxystyrene), and halogenostyrene (for example, chlorostyrene, dichlorostyrene, trichlorostyrene, tetrachlorostyrene, penta-chlorostyrene, bromostyrene, dibromostyrene, iodostyrene, fluorostyrene, trifluorostyrene, 2-bromo-4-trifluoromethylstyrene, and 4-fluoro-3-trifluoromethyl-styrene);

crotonates such as alkyl crotonate (for example, butyl crotonate, hexyl crotonate, and glycerine monocrotonate);

dialkyl itaconates (for example, dimethyl itaconate, diethyl itaconate, and dibutyl itaconate); dialkyl maleates or fumarates (for example, dimethyl maleate and dibutyl fumarate); and (meth)acrylonitrile.

There can be used as well hydroxystyrene homo- or co-polymers or a novolak type phenol resin, for example, poly(hydroxystyrene) and poly(hydroxystyrene-co-vinylcyclohexanol), a novolak resin, a cresol novolak resin, and a halogenated phenol novolak resin. More specifically, it includes, for example, the methacrylic acid copolymers, the acrylic acid copolymers, the itaconic acid copoymers, the crotonic acid copolymers, the maleic anhydride co-polymers, for example, with styrene as a co-monomer, and maleic acid copolymers, and partially esterified maleic acid copolymers each described in, for example, JP 59-44615-B4 (the term "JP-B4" as used herein means an examined Japanese patent publication), JP 54-34327-B4, JP 58-12577-B4, and JP 54-25957-B4, JP 59-53836-A, JP 59-71048-A, JP 60-159743-A, JP 60-258539-A, JP 1-152449-A, JP 2-199403-A, and JP 2-199404-A, and which copolymers can be further reacted with an amine, as e.g disclosed in U.S. Pat. No. 5,650,263; further, a cellulose derivative having a carboxyl group on a side chain can be used, and particularly preferred are copolymers of benzyl (meth)acrylate and (meth)acrylic acid and copolymers of benzyl (meth)acrylate, (meth)acrylic acid and other monomers, for example as described in U.S. Pat. No. 4,139,391, JP 59-44615-B4, JP 60-159743-A and JP 60-258539-A.

With respect to those having carboxylic acid groups among the above organic binder polymers, it is possible to react some or all of the carboxylic acid groups with glycidyl (meth)acrylate or an epoxy(meth)acrylate to obtain photopolymerizable organic binder polymers for the purpose of improving the photosensitivity, coating film strength, the coating solvent and chemical resistance and the adhesion to the substrate. Examples are disclosed in, JP 50-34443-B4 and JP 50-34444-B4, U.S. Pat. No. 5,153,095, by T. Kudo et al. in J. Appl. Phys., Vol. 37 (1998), p. 3594-3603, U.S. Pat. Nos. 5,677,385, and 5,650,233.

The weight-average molecular weight of the binders is preferably 500 to 1,000,000, e.g. 3,000 to 1,000,000, more preferably 5,000 to 400,000.

These compounds may be used singly or as a mixture of two or more kinds. The content of the binder in the light-sensitive resin composition is preferably 10 to 95 weight %, more preferably 15 to 90 weight % based on the whole solid matters.

Further, in the color filter the total solid component of each color may contain an ionic impurity-scavenger, e.g. an organic compound having an epoxy group. The concentration of the ionic impurity scavenger in the total solid component generally is in the range from 0.1% by weight to 10% by weight. Examples of color filters, especially with respect to the above described combinations of pigments and ionic impurity scavenger are given in EP 320264. It is understood, that the photoinitiators according to the present invention, i.e. the compounds of the formula I, II, III and IV in the color filter formulations described in EP 320264 can replace the triazine initiator compounds.

The compositions according to this invention can comprise additionally a crosslinking agent which is activated by an acid, for example as described in JP 10 221843-A, and a compound which generates acid thermally or by actinic radiation and which activates a crosslinking reaction.

The compositions according to this invention can also comprise latent pigments which are transformed into finely dispersed pigments during the heat treatment of the latent pigment containing photosensitive pattern or coating. The heat treatment can be performed after exposure or after development of the latent pigment-containing photoimageable layer. Such latent pigments are soluble pigment precursors which can be transformed into insoluble pigments by means of chemical, thermal, photolytic or radiation induced methods as described, for example, in U.S. Pat. No. 5,879, 855. This transformation of such latent pigments can be enhanced by adding a compound which generates acid at actinic exposure or by adding an acidic compound to the composition. Therefore, a color filter resist can also be prepared, which comprises a latent pigment in a composition according to this invention.

The compositions according to the invention also find application for the production of one- or more-layered materials for the image recording or image reproduction (copies, reprography), which may be mono- or polychromatic. Furthermore the materials are suitable for color proofing systems. In this technology formulations containing microcapsules can be applied and for the image production the radiation curing can be followed by a thermal treatment. Such systems and technologies and their applications are for example disclosed in U.S. Pat. No. 5,376,459.

Substrates used for photographic information recordings include, for example, films of polyester, cellulose acetate or polymer-coated papers; substrates for offset printing formes are specially treated aluminium, substrates for producing printed circuits are copper-clad laminates, and substrates for producing integrated circuits are silicon wafers. The layer thicknesses for photographic materials and offset printing formes is generally from about 0.5 µm to 10 µm, while for printed circuits it is from 1.0 µm to about 100 µm. Following the coating of the substrates, the solvent is removed, generally by drying, to leave a coat of the photoresist on the substrate.

Following the coating of the substrates, the solvent is removed, generally by drying, to leave an essentially dry resist film of the photoresist on the substrate.

The term "imagewise" exposure includes both, exposure through a photomask comprising a predetermined pattern, for example a slide or a reticle, as well as exposure by means of a laser or light beam, which for example is moved under computer control over the surface of the coated substrate and in this way produces an image, and irradiation with computer-controlled electron beams. It is also possible to use masks made of liquid crystals that can be adressed pixel by pixel to generate digital images, as is, for example, described by A. Bertsch, J. Y. Jezequel, J. C. Andre in Journal of Photochemistry and Photobiology A: Chemistry 1997, 107, p. 275–281 and by K.-P. Nicolay in Offset Printing 1997, 6, p. 34–37. Following the imagewise exposure of the material and prior to development, it may be advantageous to carry out thermal treatment for a short time. After the development a thermal post bake can be performed to harden the composition and to remove all traces of solvents. The temperatures employed are generally 50–250° C., preferably 80–220° C.; the duration of the thermal treatment is in general between 0.25 and 60 minutes.

The photocurable composition may additionally be used in a process for producing printing plates or photoresists as is described, for example, in DE 4013358. In such a process the composition is exposed for a short time to visible light with a wavelength of at least 400 nm, without a mask, prior to, simultaneously with or following imagewise irradiation.

After the exposure and, if implemented, thermal treatment, the unexposed areas of the photosensitive coating are removed with a developer in a manner known per se.

As already mentioned, the novel compositions can be developed by aqueous alkalis. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents. Depending on the substrate also solvents, e.g. organic solvents, can be used as developer, or, as mentioned above mixtures of aqueous alkalis with such solvents.

Photocuring is of great importance for printings, since the drying time of the ink is a critical factor for the production rate of graphic products, and should be in the order of fractions of seconds. UV-curable inks are particularly important for screen printing and offset inks.

As already mentioned above, the novel mixtures are highly suitable also for producing printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent or aqueos solutions. Another field where photocuring is employed is the coating of metals, in the case, for example, of the coating of metal plates and tubes, cans or bottle caps, and the photocuring of polymer coatings, for example of floor or wall coverings based on PVC. Examples of the photocuring of paper coatings are the colourless varnishing of labels, record sleeves and book covers.

Also of interest is the use of the novel photoinitiators for curing shaped articles made from composite compositions. The composite compound consists of a self-supporting matrix material, for example a glass fibre fabric, or alternatively, for example, plant fibres [cf. K.-P. Mieck, T. Reussmann in Kunststoffe 85 (1995), 366–370], which is impregnated with the photocuring formulation. Shaped parts comprising composite compounds, when produced using the novel compounds, attain a high level of mechanical stability and resistance. The novel compounds can also be employed as photocuring agents in moulding, impregnating and coating compositions as are described, for example, in EP 7086. Examples of such compositions are gel coat resins, which are subject to stringent requirements regarding curing activity and yellowing resistance, and fibre-reinforced mouldings, for example, light diffusing panels which are planar or have lengthwise or crosswise corrugation. Techniques for producing such mouldings, such as hand lay-up, spray lay-up, centrifugal casting or filament winding, are described, for example, by P. H. Selden in "Glasfaserverstarkte Kunststoffe", page 610, Springer Verlag Berlin-Heidelberg-New York 1967. Examples of articles which can be produced by these techniques are boats, fibre board or chipboard panels with a double-sided coating of glass fibre-reinforced plastic, pipes, containers, etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The novel photocurable compositions can also be used for casting resins or for embedding articles, for example electronic components, etc.

The compositions and compounds according to the invention can be used for the production of holographies, waveguides, optical switches wherein advantage is taken of the development of a difference in the index of refraction between irradiated and unirradiated areas.

The use of photocurable compositions for imaging techniques and for the optical production of information carriers is also important. In such applications, as already described above, the layer (wet or dry) applied to the support is irradiated imagewise, e.g through a photomask, with UV or visible light, and the unexposed areas of the layer are removed by treatment with a developer. Application of the photocurable layer to metal can also be carried out by electrodeposition. The exposed areas are polymeric through crosslinking and are therefore insoluble and remain on the support. Appropriate colouration produces visible images. Where the support is a metallized layer, the metal can, following exposure and development, be etched away at the unexposed areas or reinforced by electroplating. In this way it is possible to produce electronic circuits and photoresists. When used in image-forming materials the novel photoinitiators provide excellent performance in generating so called printout images, whereby a color change is induced due to irradiation. To form such printout images different dyes and/or their leuco form are used and examples for such print out image systems can be fount e.g. in WO 96/41240, EP 706091, EP 511403, U.S. Pat. Nos. 3,579,339, and 4,622,286.

The photosensitivity of the novel compositions can extend in general from about 190 nm to 600 nm (UV-vis region). Suitable radiation is present, for example, in sunlight or light from artificial light sources. Consequently, a large number of very different types of light sources are employed. Both point sources and arrays ("lamp carpets") are suitable. Examples are carbon arc lamps, xenon arc lamps, medium-, high- and low-pressure mercury lamps, possibly with metal halide dopes (metal-halogen lamps), microwave-stimulated metal vapour lamps, excimer lamps, superactinic fluorescent tubes, fluorescent lamps, argon incandescent lamps, electronic flashlights, photographic flood lamps, light emitting diodes (LED), electron beams and X-rays. The distance between the lamp and the substrate to be exposed in accordance with the invention may vary depending on the intended application and the type and output of lamp, and may be, for example, from 2 cm to 150 cm. Laser light sources, for example excimer lasers, such as KrF excimer lasers for exposure at 248 nm and ArF excimer lasers for exposure at 193 nm are also suitable. Lasers in the visible region can also be employed. By this method it is possible to produce printed circuits in the electronics industry, lithographic offset printing plates or relief printing plates, and also photographic image recording materials.

The invention therefore also provides a process for the photopolymerization of monomeric, oligomeric or polymeric compounds containing at least one ethylenically unsaturated double bond, which comprises adding to the abovementioned compounds at least one photoinitiator of the formula I, II, III or IV as described above and irradiating the resulting composition with electromagnetic radiation, in particular light of the wavelength 190 to 600 nm, with electron beam, or with X-rays.

The invention additionally provides compositions for producing pigmented and nonpigmented paints and varnishes, powder coatings, printing inks, printing plates, adhesives, dental compositions, resist materials, including photoresists, color filter materials, as composition for encapsulating electrical and electronic components, for producing magnetic recording materials, micromechanical parts, waveguides, optical switches, plating masks, etch masks, colour proofing systems, glass fibre cable coatings, screen printing stencils, for producing three-dimensional objects by means of stereolithography, and as image recording material, especially for holographic recordings, microelectronic circuits, decolorizing materials, decolorizing materials for image recording materials, for image recording materials using microcapsules.

The invention further provides a coated substrate which is coated on at least one surface with a composition as described above, and describes a process for the photographic production of relief images, in which a coated substrate is subjected to imagewise exposure and then the unexposed portions are removed with a developer. Imagewise exposure may be effected by irradiating through a mask or by means of a laser beam. Of particular advantage in this context is the laser beam exposure already mentioned above.

The compounds of the invention have a high sensitivity and resolution at low concentration, even without a sensitizer. They have a good thermal stability and low volatility, and are also suitable for photopolymerisations in the presence of air (oxygen). Further, the compounds according to the present invention cause only low yellowing in the compositions after photopolymerization.

The examples which follow illustrate the invention in more detail. Parts and percentages are, as in the remainder of the description and in the claims, by weight, unless stated otherwise. Where alkyl radicals having more than three carbon atoms are referred to without any mention of specific isomers, the n-isomers are meant in each case.

EXAMPLE 1

Synthesis of 1-(4-Methylsulfanyl-phenyl)-butan-1,2-dione 2-oxime-O-acetate

In formula I: $R_1=C_2H_5$; $R_2=COCH_3$; $R_3$, $R_4$, $R_6$, $R_7=H$; $R_5=SCH_3$ 1.a. 1-(4-Methylsulfanyl-phenyl)-butan-1,2-dione 2-oxime 11.0 g (0.206 mol) of sodium methoxide is suspended in 130 ml of methanol. Then isoamyl nitrite (27 ml, 0.206 mol) and 25 g (0.129 mol) of 1-(4-Methylsulfanyl-phenyl)-butan- 1-one dissolved in 70 ml of tetrahydrofuran (THF) are added and the reaction solution is stirred at room temperature for 1.5 days. After concentrating, water and acetic acid are added to neutralise. The crude product is extracted with ethyl acetate, washed with brine, dried over $MgSO_4$, and concentrated. The residue is purified by column chromatography on silica gel with ethyl acetate-hexane (15:85) as an eluent. The structure is confirmed by the $^1$H-NMR spectrum ($CDCl_3$). δ[ppm]: 1.14 (t, 3H), 2.52 (s, 3H), 2.72 (q, 2H), 7.25 (d, 2H), 7.89 (d, 2H), 8.01 (s, 1H).

1.b. 1-(4-Methylsulfanyl-phenyl)-butan-1,2-dione 2-oxime-O-acetate 3.5 g (15.7 mmol) of 1-(4-Methylsulfanyl-phenyl)-butane-1,2-dione 2-oxime is dissolved in 20 ml of THF and the solution is cooled in an ice-bath. Acetyl chloride (1.23 ml, 17.3 mmol) and triethylamine (3.3 ml, 23.6 mmol) are added successively and the reaction solution is stirred at 0° C. for 1 hr and then poured into water. The crude product is extracted with ethyl acetate, washed with brine, dried over $MgSO_4$ and concentrated. The residue is purified by column chromatography on silica gel with ethyl acetate-hexane (20:80) as an eluent. The structure is confirmed by the $^1$H-NMR spectrum ($CDCl_3$). δ[ppm]: 1.17 (t, 3H), 2.27 (s, 3H), 2.53 (s, 3H), 2.78 (q, 2H), 7.27 (d, 2H), 8.00 (d, 2H).

EXAMPLES 2–17

The compounds of Examples 2–17 are prepared according to the method described in example 1 from the corresponding ketones, which are synthesised by Friedel-Crafts-reaction using the corresponding aromatics and acyl chlorides in the presence of aluminum chloride in dichloromethane. The compounds and $^1$H-NMR-data are given in table 1.

TABLE 1

| Example | $R_1$ | $R_2$ | $R_4$ | $R_5$ | state/mp [° C.] $^1$H-NMR, δ [ppm] |
|---|---|---|---|---|---|
| 2 | $C_2H_5$ | —CO—C$_6$H$_5$ (benzoyl) | H | —$SCH_3$ | (oil) 1.26(t, 3H), 2.53(s, 3H), 2.91(q, 2H), 7.32(d, 2H), 7.53(t, 2H), 7.66(t, 1H), 8.08–8.13(m, 4H) |
| 3 | $C_2H_5$ | —$COCH_3$ | H | morpholin-4-yl | (oil) 1.56(t, 3H), 2.28(s, 3H), 2.77(q, 2H), 3.35(t, 4H), 3.85(t, 4H), 6.87(d, 2H) 8.03(d, 2H) |
| 4 | $C_2H_5$ | —CO—C$_6$H$_5$ (benzoyl) | H | morpholin-4-yl | (oil) 1.25(t, 3H) 2.90(q, 2H) 3.36(t, 4H) 3.86(t, 4H) 6.90(d, 2H) 7.52(t, 2H) 7.65(t, 1H) 8.10–8.18(m, 4H) |
| 5 | $C_2H_5$ | —$COCH_3$ | —$OCH_3$ | —$OCH_3$ | (oil) 1.17(t, 3H) 2.27(s, 3H) 2.79(q, 2H) 3.95(s, 3H) 3.96(s, 3H) 6.92(d, 1H) 7.70(d, 1H) 7.77(dd, 1H) |
| 6 | $C_2H_5$ | —CO—C$_6$H$_5$ (benzoyl) | —$OCH_3$ | —$OCH_3$ | 89–93 1.25(t, 3H) 2.91(q, 2H) 3.97(s, 3H) 3.99(s, 3H) 6.98(d, 2H) 7.54(t, 2H) 7.65(t, 1H) 7.79(d, 1H) 7.90(dd, 1H) 8.12(d, 2H) |
| 7 | Phenyl | —$COCH_3$ | H | —$SCH_3$ | (oil) 2.02(s, 3H) 2.53(s, 3H) 7.30(d, 2H) 7.40(t, 2H) 7.48(t, 1H) 7.71(d, 2H) 7.83(d, 2H) |
| 8 | $C_2H_5$ | —$COCH_3$ | H | —$OCH_3$ | (oil) 1.16(t, 3H) 2.27(s, 3H) 2.78(q, 2H) 3.88(s, 3H) 6.96(d, 2H) 8.09(d, 2H) |
| 9 | $C_2H_5$ | —CO—C$_6$H$_5$ (benzoyl) | H | —$OCH_3$ | (oil) 1.26(t, 3H) 2.91(q, 2H) 3.90(s, 3H) 7.00(d, 2H) 7.53(t, 2H) 7.65(t, 1H) 8.13(d, 2H) 8.20(d, 2H) |
| 10 | $C_2H_5$ | —$COCH_3$ | H | —S—C$_6$H$_5$ (phenylthio) | (oil) 1.13(t, 3H) 2.25(s, 3H) 2.77(q, 2H) 7.18(d, 2H) 7.41–7.43(m, 3H) 7.51–7.54(m, 2H) 7.94(d, 2H) |

TABLE 1-continued

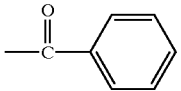

| Example | R₁ | R₂ | R₄ | R₅ | state/mp [° C.] ¹H-NMR, δ [ppm] |
|---|---|---|---|---|---|
| 11 | $C_2H_5$ | 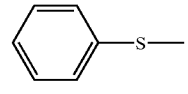 | H | 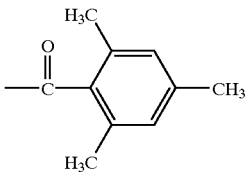 | 78–80 1.25(t, 3H) 2.89(q, 2H) 7.21(d, 2H) 7.41–7.43(m, 3H) 7.50–7.55(m, 4H) 7.65(t, 1H) 8.04(d, 2H) 8.10(d, 2H) |
| 12 | $C_2H_5$ | 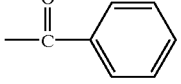 | H | —$SCH_3$ | (oil) 1.14(3H, t) 2.33(3H, s) 2.38(6H, s) 2.53(3H, s) 2.78(2H, q) 6.92(2H, s) 7.29(2H, d) 8.05(2H, d) |
| 13 | $CH_3$ | 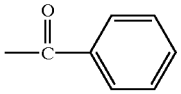 | H | —$SCH_3$ | 87–90 2.43(3H, s) 2.53(3H, s) 7.30(2H, d) 7.52(2H, t) 7.67(1H, t) 8.13(4H, d) |
| 14 | n-$C_6H_{13}$ | —$COCH_3$ | H | —$SCH_3$ | (oil) 0.88(3H, t) 1.28(4H, m) 1.35(2H, m) 1.53(2H, m) 2.26(3H, s) 2.77(2H, t) 7.27(2H, d) 8.01(2H, d) |
| 15 | n-$C_6H_{13}$ | 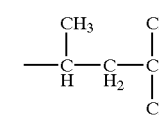 | H | —$SCH_3$ | (oil) 0.85(3H, t) 1.30(4H, m) 1.41(2H, m) 1.63(2H, m) 2.52(3H, s) 2.91(2H, t) 7.30(2H, d) 7.51(2H, t) 7.65(1H, t) 8.10(4H, d) |
| 16 | 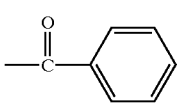 | 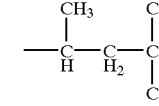 | H | —$SCH_3$ | (oil) 0.92(9H, s) 1.41(3H, d) 1.51(1H, dd) 1.98(1H, dd) 2.49(3H, s) 3.54(1H, m) 7.28(2H, d) 7.54(2H, t) 7.66(1H, t) 8.10(2H, d) 8.13(2H, d) |
| 17 | 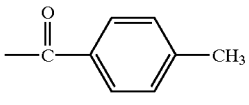 | —$COCH_3$ | H | —$SCH_3$ | (oil) 0.91(9H, s) 1.30(3H, d) 1.43(1H, dd) 1.85(1H, dd) 2.27(3H, s) 2.52(3H, s) 3.90(1H, m) 7.29(2H, d) 7.97(2H, d) |
| 18 | n-$C_6H_{13}$ | 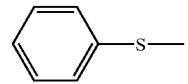 | H | 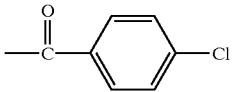 | (oil) 0.85(t, 3H), 1.22–1.44(m, 6H), 1.59–1.67(m, 2H), 2.45(s, 3H), 2.88(t, 2H), 7.21(d, 2H), 7.31(d, 2H), 7.40–7.45(m, 3H), 7.52–7.57(m, 2H), 7.98(d, 2H), 8.04(d, 2H) |
| 19 | n-$C_6H_{13}$ | 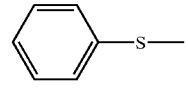 | H | 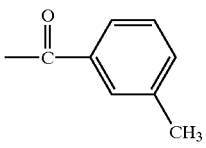 | (oil) 0.85(t, 3H), 1.23–1.44(m, 6H), 1.57–1.67(m, 2H), 2.87(t, 2H), 7.20(d, 2H), 7.39–7.56(m, 7H), 8.00–8.05(m, 4H) |
| 20 | n-$C_6H_{13}$ | 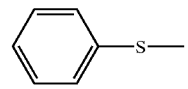 | H | 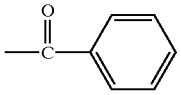 | (oil) 0.84(t, 3H), 1.23–1.44(m, 6H), 1.57–1.66(m, 2H), 2.43(s, 3H), 2.88(t, 2H), 7.21(d, 2H), 7.38–7.47(m, 5H), 7.50–7.55(m, 2H), 7.85–7.92(m, 2H), 8.05(d, 2H) |
| 21 | n-$C_6H_{13}$ | 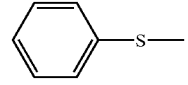 | H | 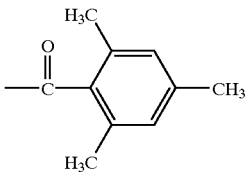 | (oil) 0.84(t, 3H) 1.28(m, 4H) 1.40(m, 2H) 1.63(m, 2H) 2.89(t, 2H) 7.22(d, 2H) 7.42(m, 3H) 7.54(m, 4H) 7.64(t, 1H) 8.06(d, 2H) 8.10(d, 2H) |

EXAMPLE 22

Synthesis of 1-(4-Methylsulfanyl-phenyl)-butan-1-one oxime-O-acetate

In formula III: $R_1'=C_3H_7$; $R_2=COCH_3$; $R_5'=SCH_3$; $R_4'$, $R_6'=H$

22.a. 1-(4-Methylsulfanyl-phenyl)-butan-1-one oxime 9.72 g (50 mmol) of 1-(4-Methylsulfanyl-phenyl)-butane-1-one is dissolved in hot ethanol. Then a solution of hydroxylammonium chloride (3.58 g, 51.5 mmol) and sodium acetate (7.0 g, 85 mmol) in 20 ml of water is added, and the reaction solution is stirred at 100° C. for 4 hrs. After cooling and concentrating, water is added. The crude product is extracted with ethyl acetate, washed with brine, dried over $MgSO_4$, and concentrated. The residue is purified by column chromatography on silica gel with ethyl acetate-hexane (20:80) as an eluent. The structure is confirmed by the $^1$H-NMR spectrum (CDCl$_3$). δ[ppm]: 0.98 (t, 3H), 1.54–1.64 (m, 2H), 2.50 (s, 3H), 2.76 (t, 2H), 7.24 (d, 2H), 7.54 (d, 2H), 7.98 (s, 1H).

22.b. 1-(4-Methylsulfanyl-phenyl)-butan-1-one oxime-O-acetate 2.0 g (9.56 mmol) of 1-(4-Methylsulfanyl-phenyl)-butan-1-one oxime is dissolved in 10 ml of tetrahydrofuran (THF) and the solution is cooled in an ice-bath. Acetyl chloride (0.75 ml, 10.5 mmol) and triethylamine (2.0 ml, 14.3 mmol) are added successively and the reaction solution is stirred at 0° C. for 1 hr and then poured into water. The crude product is extracted with ethyl acetate, washed with brine, dried over $MgSO_4$ and concentrated. The residue is purified by column chromatography on silica gel with ethyl acetate-hexane (20:80) as an eluent. The product is a colorless oil. The structure is confirmed by the $^1$H-NMR spectrum (CDCl$_3$). δ[ppm]: 0.98 (t, 3H), 1.56–1.64 (m, 2H), 2.26 (s, 3H), 2.50 (s, 3H), 2.81 (t, 2H), 7.25 (d, 2H), 7.65 (d, 2H).

EXAMPLE 23

1-(4-phenylsulfanyl-phenyl)-butane-1-one oxime-O-acetate

In formula III: $R_1'=C_3H_7$; $R_2=COCH_3$; $R_4'$, $R_6'=H$; $R_5'=-S-C_6H_5$ The compound is prepared according to the method described in example 22 using 1-(4-phenylsulfanyl-phenyl)-butane-1-one as starting material. The structure is confirmed by the $^1$H-NMR spectrum (CDCl$_3$). δ[ppm]: 1.04 (t,3H), 1.71 (m,2H), 2.93 (t, 2H), 7.32–7.52 (m,9H), 7.62 (t, 1H), 7.70 (d,2H), 8.10 (d,2H).

EXAMPLE 24

Hydroxyimino-(4-Methylsulfanyl-phenyl)-acetic acid ethyl ester-O-acetate

In formula III: $R_1'=COOC_2H_5$, $R_2=COCH_3$, $R_4'$, $R_6'=H$, $R_5'=SCH_3$

24.a. (4-Methylsulfanyl-phenyl)-oxo-acetic acid ethyl ester 37.5 g (0.3 mol) of Thioanisol and 41.4 g (0.3 mol) of chloro-oxo-acetic acid ethyl ester dissolved in 200 ml of dichloromethane are added dropwise to a suspension of 60 g (0.45 mol) of aluminum trichloride in 350 ml of dichloromethane at 0° C. The solution is stirred overnight at room temperature and then heated to reflux for two hours. After cooling to room temperature, the reaction mixture is poured on a mixture of 100 ml conc. HCl and ice/water. After extraction with dichloromethane, the organic phase is washed with water and sodium bicarbonate and dried over magnesium sulfate. The salt is filtered off and the solvent distilled to give 52.3 g (78%) of (4-methylsulfanyl-phenyl)-oxo-acetic acid ethyl ester as a yellow oil. This oil is used for the next step without further purification. The structure is confirmed by the $^1$H-NMR spectrum (in CDCl$_3$). δ[ppm]: 7.87 (d,2H), 7.24 (d,2H), 4.39 (q,2H), 2.48 (s,2H), 1.37 (t,3H).

24.b. Hydroxyimino-(4-methylsulfanyl-phenyl)-acetic acid ethyl ester 22.4 g (0.1 mol) of (4-Methylsulfanyl-phenyl)-oxo-acetic acid ethyl ester and 7.6 g (0.1 mol) of hydroxylammonium hydrochloride are dissolved in 180 ml of pyridine and the mixture is stirred at room temperature for 16 hours. The yellowish solution is diluted with water and ethyl acetate, the organic phase separated and the aqueous phase extracted several times with ethyl acetate. The combined organic extracts are washed with diluted hydrogen chloride and water and the solvent is evaporated. 24 g (100%) of crude hydroxyimino-(4-methylsulfanyl-phenyl)-acetic acid ethyl ester (66:34 mixture of the E and Z-isomers) are thus obtained and used in the next step without further purification. The structure is confirmed by the $^1$H-NMR spectrum (in CDCl$_3$). δ[ppm]: 7.46 (d,2H), 7.19 (d,2H), 4.44 (E) and 4,32 (Z) (two d,2H) 2.47 (Z) and 2.46 (E) (s,3H) 1.37 (E) and 1.28 (Z) (t,3H).

24.c. Hydroxyimino-(4-methylsulfanyl-phenyl)-acetic acid ethyl ester-O-acetate 14.35 g (0.06 mol) of crude hydroxyimino-(4-methylsulfanyl-phenyl)-acetic acid ethyl ester and 9.1 g (0.09 mol) of triethylamine are dissolved in 100 ml of THF. 5.2 g (0.066 mol) of acetylchloride, dissolved in 10 ml of THF, are added at 0° C. The suspension is warmed up to room temperature and stirred overnight. The reaction mixture is diluted with ethyl acetate and water, the water phase extracted several times with additional ethyl acetate and the combined organic fractions washed with brine and water and dried over $MgSO_4$. After distilling off the solvent, the crude product is obtained as an oil, which is purified by filtration over silica gel. 11.2 g (66%) of hydroxyimino-(4-methylsulfanyl-phenyl)-acetic acid ethyl ester-O-acetate are obtained as yellowish oil. The $^1$H-NMR spectrum reveals a 70:30 mixture of the (E) and (Z) isomers. The structure is confirmed by the $^1$H-NMR spectrum (in CDCl$_3$). δ[ppm] 7.59 and 7.43 (d,2H), 4.44 and 4.35 (q,2H), 2.48 and 2.47 (s,3H), 2.15 and 2.13 (s,3) 1.33 and 1.32 (t,3H).

| | Elemental analysis: | | | |
| --- | --- | --- | --- | --- |
| | % C | % H | % N | % S |
| calc. | 55.50 | 5.37 | 4.98 | 11.40 |
| Found | 55.54 | 5.46 | 4.95 | 11.41 |

EXAMPLE 25

Hydroxyimino-(4-methylsulfanyl-phenyl)-acetic acid ethyl ester-O-benzoate

In formula III:

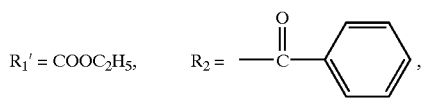

$R_4'$, $R_6'$=H, $R_5'$=SCH$_3$

As described in example 24.c., 12.3 g (0.05 mol)%) of hydroxyimino-(4-methylsulfanyl-phenyl)-acetic acid ethyl ester-O-acetate are reacted with 7.95 g (0.056 mol) of benzoyl chloride. 17.5 g of the crude product are obtained as a brownish oil, which is further purified by flash chromatography on silica gel (eluent: petroleum ether/ethyl acetate 5:1, then 3:1). A first fraction (yellowish oil, 5.4 g, 31%) are identified by $^1$H-NMR as the pure (E)-isomer of hydroxyimino-(4-methylsulfanyl-phenyl)-acetic acid ethyl ester-O-benzoate. A second fraction (yellowish oil, 7.6 g, 44%) is identified as a 45:55 mixture of the (E) and (Z) isomers of hydroxyimino-(4-methylsulfanyl-phenyl)-acetic acid ethyl ester-O-benzoate. Fraction 1 ((E)-isomer): $^1$H-NMR (CDCl$_3$), δ[ppm]: 8.01 (d,2H), 7.68 (d,2H), 7.57 (t,1H), 7.48 (t,2H), 7.25 (d,2H), 4.49 (q,2H), 2.49 (s,3H), 1.38 (t,3H).

| | Elemental analysis: | | | |
|---|---|---|---|---|
| | % C | % H | % N | % S |
| calc. | 62.96 | 4.99 | 4.08 | 9.34 |
| Found | 62.98 | 4.99 | 3.97 | 9.20 |

Fraction 2 ((E) and (Z)-isomer): $^1$H-NMR (CDCl$_3$), δ[ppm]: 8.01 and 7.89 (d,2H), 7.68–7.20 (7H), 4.49 and 4.39 (q,2H), 2.52 and 2.49 (s,3H), 1.40 and 1.38 (t,3H).

| | Elemental analysis: | | | |
|---|---|---|---|---|
| | % C | % H | % N | % S |
| calc. | 62.96 | 4.99 | 4.08 | 9.34 |
| Found | 62.79 | 4.90 | 4.34 | 9.25 |

EXAMPLE 26

Hydroxyimino-(3,4-dimethoxy-phenyl)-acetic acid ethyl ester-O-acetate

In formula III: $R_1'$=COOC$_2$H$_5$, $R_2$=COCH$_3$, $R_4'$=OCH$_3$, $R_5'$=OCH$_3$, $R_6'$=H

26.a. (3,4-Dimethoxy-phenyl)-oxo-acetic acid ethyl ester

This compound is prepared analogous to the method described in example 24.a., using veratrol instead of thioanisole as starting material. Yield: 74% of an orange oil. The structure is verified by the $^1$H-NMR spectrum (CDCl$_3$), δ[ppm]: 7.58 (dxd, 1H), 7.53 (d, 1H), 6.87 (d, 1H), 4.38 (q,2H), 3.92 (s,3H), 3.89 (s,3H), 1.37 (q,3H).

26.b. (3,4-Dimethoxy-phenyl)-hydroxyimino-acetic acid ethyl ester

This compound is prepared from (3,4-dimethoxy-phenyl)-oxo-acetic acid ethyl ester as described in example 24.b. and obtained in a yield of 83% of an 80:20 mixture of the (E) and (Z) isomers. $^1$H-NMR (CDCl$_3$), δ[ppm]: 8.43 (broad s, 1H), 7.18 and 7.17 (d, 1H), 6.99 (dxd, 1H), 6.83 (d, 1H), 4.44 and 4.33 (q,2H), 3,90, 3.89, 3.87, 3.86 (s,6H), 1.38, 1.36 (t,3H).

26.c. Ethyl 2-(3,4-dimethoxyphenyl)-2-acetyloximino-acetate

As described in example 24.c., (3,4-dimethoxy-phenyl)-hydroxyimino-acetic acid ethyl ester is reacted with acetyl chloride. The product is obtained in 79% yield as a yellowish liquid. The $^1$H-NMR spectrum (CDCl$_3$) reveals a 85:15 mixture of the (E) and (Z) isomers: δ[ppm]: 7.38 and 7.32 (d, 1H), 7.15–7.10 (1H), 6.88 and 6.83 (d, 1H), 4.44 and 4.35 (q,2H) 3.87, 3.86, 3.84, 3.83 (s,6H), 2.27 and 2.16 (s,3H), 1.37 and 1.32 (d,3H).

| | Elemental analysis: | | |
|---|---|---|---|
| | % C | % H | % N |
| calc. | 56.95 | 5.80 | 4.74 |
| Found | 56.71 | 5.76 | 4.88 |

EXAMPLE 27

Ethyl 2-(3,4-dimethoxyphenyl)-2-benzoyloximino-benzoate

In formula III:

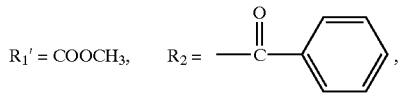

$R_4'$=OCH$_3$, $R_5'$=OCH$_3$, $R_6'$=H

This compound is prepared from (3,4-dimethoxyphenyl)-hydroxyimino-acetic acid ethyl ester by reaction with benzoyl chloride as described in example 25. The solid product is recrystallized from toluene to give the pure (E)-isomer as a white solid, m.p. 98–99° C. (yield: 49%). Evaporation of the motherliquid gives 43% of a yellow liquid, which according to the $^1$H-NMR spectrum is a crude 55:45 mixture of the (E) and the (Z) isomer. $^1$H-NMR spectrum (CDCl$_3$), (E)-isomer, δ[ppm]: 8.02 (d, 1H), 7.57, 7.49 (d), 7.48 (t,3H), 7.13 (d, 1H), 6.87 (d,2H), 4.49 (q,2H), 3.94 (s,3H), 3.92 (s,3H), 1.39 (t,3H).

| | Elemental analysis: | | |
|---|---|---|---|
| | % C | % H | % N |
| calc. | 63.86 | 5.36 | 3.92 |
| Found | 63.95 | 5.37 | 3.75 |

EXAMPLE 28

1-(4-Methylsulfanyl-phenyl)-butan-1-one oxime-O-benzoate

In formula III:

$R_1' = C_3H_7$, $R_2 =$ 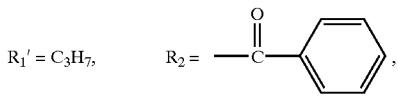

$R_4'$, $R_6'$=H=, $R_5'$=SCH$_3$

This compound is prepared as described in example 22b, using benzoyl chloride instead of acetyl chloride. The product is obtained as an oil which solidifies upon standing at room temperature (m.p. 48–53° C.). The structure is confirmed by the $^1$H-NMR spectrum, δ[ppm]: 1.04 (t, 3H), 1.71 (dt, 2H), 2.52 (s, 3H), 2.94 (t, 2H), 7.27 (d, 2H), 7.51 (t, 2H), 7.62 (t, 1H), 7.74 (d, 2H), 8.11 (d, 2H).

EXAMPLE 29

1-(4-Phenylsulfanyl-phenyl)-octan-1-one oxime-O-acetate

In formula III: $R_1'$=C$_7$H$_{15}$, $R_2$=COCH$_3$, $R_4'$, $R_6'$=H=, $R_5'$=SC$_6$H$_5$ This compound is prepared as described in example 22b from the corresponding ketone. The product is obtained as an oil. The structure is confirmed by the $^1$H-NMR spectrum, δ [ppm]: 0.87 (t, 3H), 1.20–1.39 (m, 8H), 1.49–1.60 (m, 2H), 2.25 (s, 3H), 2.79 (t, 2H), 7.26 (d, 2H), 7.31–7.38 (m, 3H), 7.42 (d, 2H), 7.61 (d, 2H).

EXAMPLE 30

1-(4-Phenylsulfanyl-phenyl)-octan-1-one oxime-O-benzoate

In formula III: $R_1'$=C$_7$H$_{15}$, $R_2$=CO—C$_6$H$_5$, $R_4'$, $R_6'$=H, $R_5'$=SC$_6$H$_5$ This compound is prepared as described in example 29 using benzoyl chloride instead of acetyl chloride. The structure is confirmed by the $^1$H-NMR spectrum, δ[ppm]: 0.85 (t, 3H), 1.25–1.44 (m, 8H), 1.65 (t, 2H), 2.94 (t, 2H), 7.20–7.45 (m, 7H), 7.50 (t, 2H), 7.62 (t, 1H), 7.69 (d, 2H), 8.10 (d, 2H).

EXAMPLE 31

2,2,2-Trifluoro-1-(4-methylsulfanyl-phenyl)-ethanone oxime O-acetate

In formula III: $R_1'$=CF$_3$, $R_2$=COCH$_3$, $R_4'$=$R_6'$=H, $R_5'$=SCH$_3$

31.1 2,2,2-Trifluoro-1-(4-methylsulfanyl-phenyl)-ethanone

To 50.0 g (403 mmol) of thioanisole and 49.2 g of (403 mmol) of 4-dimethylaminopyridine in 500 ml of CH$_2$Cl$_2$ 84.6 g (403 mmol) of trifluoroacetic anhydride and subsequently 123 g (926 mmol) of AlCl$_3$ are carefully added at 0° C. The reaction mixture is stirred at room temperature overnight and then poured onto ice. After extraction with CH$_2$Cl$_2$, the organic layer is washed with water, ammonium chloride aq. solution, and brine, followed by drying over anhydrous MgSO$_4$. After filtration and evaporation of the solvent, 50.0 g of yellow solid are obtained (56%). This solid is used for the next reaction without further purification. The structure is confirmed by the $^1$H-NMR spectrum (CDCl$_3$, ppm): d 2.55 (s, 3H), 7.32 (d, 2H), 7.97 (d, 2H).

31.2 2,2,2-Trifluoro-1-(4-methylsulfanyl-phenyl)-ethanone oxime 49.3 g (224 mmol) of 2,2,2-trifluoro-1-(4-methylsulfanyl-phenyl)-ethanone are dissolved in 250 ml of hot ethanol. To this solution is added dropwise a solution of hydroxylammonium chloride (16.3 g, 235 mmol) and sodium acetate (31.2 g, 381 mmol) in 125 ml of water, and the reaction solution is stirred under reflux for 6.5 hr. The reaction mixture was concentrated by rotary evaporation and poured into ice/water. The resulting yellow solid is filterd and washed with water. After drying under reduced pressure, recrystallization from hexane-ethyl acetate affords 28.4 g of white solid (54%). The structure is confirmed by the $^1$H-NMR spectrum (CDCl$_3$), δ[ppm]:: d 2.51 (s, 3H), 7.31 (d, 2H), 7.49 (d, 2H), 8.80 (broad s, 1H).

31.3 2,2,2-Trifluoro-1-(4-methylsulfanyl-phenyl)-ethanone oxime O-acetate

To a solution of 2,2,2-trifluoro-1-(4-methylsulfanyl-phenyl)-ethanone oxime (2.00 g, 8.50 mmol) and acetyl chloride (0.734 g, 9.35 mmol) in 30 ml of THF is triethylamine (1.29 g, 12.8 mmol) added dropwise at 0° C. After stirring at 0° C. for 3 hr, the reaction mixture is poured into ice/water. The products are extracted with ethyl acetate, and the organic layer is washed with NaHCO$_3$ aq. solution and brine, followed by drying over anhydrous MgSO$_4$. After filtration and evaporation of the solvent, the desired product is purified by column chromatography on silica gel with ethyl acetate-hexane (1:9) as eluent. 1.20 g of colorless oil are obtained (51%). The structure is confirmed by the $^1$H-NMR spectrum (CDCl$_3$), δ[ppm]: d 2.11 (s, 3H), 2.45 (s, 3H), 7.24 (d, 2H), 7.32 (d, 2H).

EXAMPLE 32

2,2,2-Trifluoro-1-(4-phenylsulfanyl-phenyl)-ethanone oxime O-acetate

In formula III: $R_1'$=CF$_3$, $R_2$=COCH$_3$, $R_4'$=$R_6'$=H, $R_5'$=SC$_6$H$_5$

32.1 2,2,2-Trifluoro-1-(4-phenylsulfanyl-phenyl)-ethanone

To 37.3 g (200 mmol) of diphenylsulfide and 36.7 g of (300 mmol) of 4-dimethylaminopyridine in 500 ml of CH$_2$Cl$_2$, 63.0 g (300 mmol) of trifluoroacetic anhydride and subsequently 92.0 g (690 mmol) of AlCl$_3$ are carefully added at 0° C. The reaction mixture is stirred at room temperature overnight and then poured onto ice. After extraction with CH$_2$Cl$_2$, the organic layer is washed with water, ammonium chloride aq. solution, and brine, followed by drying over anhydrous MgSO$_4$. After filtration and evaporation of the solvent, 54.1 g of brown oil are obtained. 10 g of this crude product are applied to column chromatography on silica gel with CH$_2$Cl$_2$-Hexane (1:4) as eluent. 7.40 g of yellow oil are obtained (13%). $^1$H-NMR (CDCl$_3$, ppm): d 7.19 (d, 2H), 7.45–7.49 (m, 3H), 7.54–7.7.58 (m, 2H), 7.90 (d, 2 H. 32.2 2,2,2-Trifluoro-1-(4-phenylsulfanyl-phenyl)-ethanone oxime 6.21 g (22.0 mmol) of 2,2,2-trifluoro-1-(4-phenylsulfanyl-phenyl)-ethanone are dissolved in 25 ml of hot Ethanol. To this solution a solution of hydroxylammonium chloride (1.61 g, 23.1 mmol) and sodium acetate (3.07 g, 37.4 mmol) in 12.5 ml of water is added dropwise, and the reaction solution is stirred under reflux for 6 hr. The reaction mixture was concentrated by rotary evaporation and poured into ice/water. The resulting white solid is filterd and washed with water. After drying under reduced pressure, recrystallization from hexane-CH$_2$Cl$_2$ affords 4.1 g of a white solid (63%). The structure is confirmed by the ¹H-NMR spectrum (CDCl₃), δ[ppm]: d 7.26 (d, 2H), 7.36–7.44 (m, 5H), 7.48–7.51 (m, 2H), 8.78 (s, 1H).

32.3 2,2,2-Trifluoro-1-(4-phenylsulfanyl-phenyl)-ethanone oxime O-acetate

To a solution of 2,2,2-trifluoro-1-(4-phenylsulfanyl-phenyl)-ethanone oxime (1.50 g, 5.05 mmol) and acetyl chloride (0.436 g, 5.56 mmol) in THF (25 ml) triethylamine (0.766 g, 7.57 mmol) is added dropwise at 0° C. After stirring at 0° C. for 3 hr, the reaction mixture is poured into ice/water. The products are extracted with ethyl acetate, and the organic layer is washed with NaHCO₃ aq. solution and brine, followed by drying over anhydrous MgSO₄. After filtration and evaporation of the solvent, the desired product is purified by column chromatography on silica gel with CH₂Cl₂-Hexane (1:1) as eluent. 0.91 g of a white solid are obtained (53%) as a isomeric mixture of syn and anti. The ratio of the major isomer to the minor one is 87:13 based on ¹H NMR. ¹H NMR (CDCl₃), δ[ppm]: d 2.18 and 2.28 (s, 3H), 7.24 (d, 2H), 7.34–7.53 (m, 7H). The signals assigned to the major isomer are as follows. d 2.18 (s, 3H), 7.34 (d, 2H), 7.53 (dd, 2H). The melting point of the solid is 76–80° C.

EXAMPLE 33

1-(4-Phenylsulfanyl-phenyl)-decan-1-one oxime O-pentafluorobenzoate

In formula III: $R_1'=C_9H_{19}$, $R_2=COC_6F_5$, $R_4'=R_6'=H$, $R_5'=SC_6H_5$

To a solution of 1-(4-phenylsulfanyl-phenyl)-decan-1-one oxime (2.00 g, 5.63 mmol) and pentafluorobenzoyl chloride (1.43 g, 6.19 mmol) in THF (25 ml) triethylamine (0.85 g, 8.45 mmol) is added dropwise at 0° C. After stirring at 0° C. for 1 hr, the reaction mixture is poured into ice/water. The products are extracted with ethyl acetate, and the organic layer is washed with NaHCO₃ aq. solution and brine, followed by drying over anhydrous MgSO₄. After filtration and evaporation of the solvent, the desired product is purified by column chromatography on silica gel with ethyl acetate-hexane (1:4) as eluent. 2.08 g of a white solid with a melting point of 56–59° C. are obtained (67%). ¹H NMR (CDCl₃), δ[ppm]: d 0.86 (t, 3H), 1.2–1.4 (m, 12H), 1.56 (broad s, 2H), 2.84 (t, 2H), 7.27 (d, 2H), 7.35–7.38 (m, 3H), 7.45 (dd, 2H), 7.64 (d, 2H).

EXAMPLE 34

3,3,3-Trifluoro-1-(4-methylsulfanyl-phenyl)-propan-1-one oxime O-acetate

In formula III: $R_1'=CF_3CH_2$, $R_2=COCH_3$, $R_4'=R_6'=H$, $R_5'=SCH_3$

34.1 N,N-Dimethyl-N'-(4-methylsulfanyl-benzylidene)-hydrazine 7.44 g (48.9 mmol) of 4-methylthiobenzaldehyde and 4.0 ml (52.7 mmol) of 1,1-dimethylhydrazine are dissolved in toluene (50 ml) and heated to reflux for 2.5 hr. Brine is added to the reaction mixture after cooling, and the product is extracted with toluene. The toluene layer is condensed and the residue is applied to column chromatography on silica gel with acetone-hexane (1:20) as eluent. 9.07 g of a pale yellow oil are obtained (96%). ¹H NMR (CDCl₃), δ[ppm]: d 2.48 (s, 3H), 2.96 (s, 6H), 7.20 (s, 1H), 7.21 (d, 2H), 7.49 (d, 2H).

34.2 3,3,3-Trifluoro-1-(4-methylsulfanyl-phenyl)-propan-1-one 64 ml (453 mmol) of trifluoroacetic anhydride are added dropwise to 8.68 g (44.7 mmol) of N,N-dimethyl-N'-(4-methylsulfanyl-benzylidene)-hydrazine in pyridine at 0° C. over 20 min. Then, the reaction solution is gradually warmed up to room temperature and stirred over-night. Excess trifluoroacetic anhydride and pyridine are removed by evaporation in vacuo. The residue is dissolved in 200 ml of acetonitrile, and 200 ml of 6N HCl aq. solution. After stirring overnight at room temperature, the reaction solution is neutralized with NaHCO₃. The removal of acetonitrile affords a white solid, which is filtered and washed with water. The product is purified by column chromatography on silica gel with CH₂Cl₂-Hexane (1:1) as eluent. 3.18 g of the white solid with a melting point of 118–120° C. are obtained (30%). ¹H NMR (CDCl₃), δ[ppm]: d 2.54 (s, 3H), 3.75 (q, 2H), 7.29 (d, 2H), 7.84 (d, 2H).

34.3 3,3,3-Trifluoro-1-(4-methylsulfanyl-phenyl)-propan-1-one oxime

Hydroxylammonium chloride (1.07 g, 15.4 mmol) and sodium acetate (1.85 g, 22.5 mmol) are dissolved in 10 ml of water. To this solution are added 2.35 g (10.0 mmol) of 3,3,3-trifluoro-1-(4-methylsulfanyl-phenyl)-propan-1-one in 30 ml of ethanol. The reaction mixture is heated to reflux for 6.5 hr. The reaction mixture was concentrated by rotary evaporation and poured into water. The product is extracted with CH₂Cl₂, and the organic layer is washed with water, followed by drying over anhydrous MgSO₄. After evaporation of the solvent, the product is purified by column chromatography on silica gel with CH₂Cl₂-Hexane (2:1) as eluent. 1.48 g of white solid melting at 106–107° C. are obtained (59%). ¹H NMR (CDCl₃), δ[ppm]: d 2.51 (s, 3H), 3.73 (q, 2H), 7.26 (d, 2H), 7.57 (d, 2H), 8.23 (s, 1H).

34.4 3,3,3-Trifluoro-1-(4-methylsulfanyl-phenyl)-propan-1-one oxime O-acetate To a solution of 3,3,3-trifluoro-1-(4-methylsulfanyl-phenyl)-propan-1-one oxime (1.12 g, 4.50 mmol) and acetyl chloride (0.35 ml, 4.92 mmol) in THF (10 ml) pyridine (0.40 ml, 4.95 mmol) is added dropwise at 0° C. After stirring at room temperature overnight, the reaction mixture is poured into water. The products are extracted with THF, and the organic layer is washed with NaHCO₃ aq. solution and brine, followed by drying over anhydrous MgSO₄. After filtration and evaporation of the solvent, the desired product is purified by column chromatography on silica gel with CH₂Cl₂-hexane (2:1) as eluent, 0.997 g of a pale yellow solid, melting at 70–71° C. are obtained (76%). ¹H NMR (CDCl₃), δ[ppm]: d 2.28 (s, 3H), 2.51 (s, 3H), 3.75 (q, 2H), 7.26 (d, 2H), 7.69 (d, 2H).

EXAMPLE 35

1-(4-Methylsulfanyl-phenyl)-2-phenyl-ethanone oxime O-acetate

In formula III: $R_1'=C_6H_5CH_2$, $R_2=COCH_3$, $R_4'=R_6'=H$, $R_5'=SCH_3$

35.1 1-(4-Methylsulfanyl-phenyl)-2-phenyl-ethanone

Thioanisole (6.22 g, 50 mmol) I) diliuted with CH₂Cl₂ (5 ml) is added to a suspension of AlCl₃. (6.8 g, 51 mmol) in 45 ml of CH₂Cl₂. Phenylacetyl chloride (7.73 g, 50.0 mmol) in CH₂Cl₂ (15 ml) is added dropwise at 0° C. over 5 min. Then, the reaction solution is gradually warmed up to room temperature and stirred overnight. The reaction solution is poured onto ice. The resulting white precipitate is extracted with CH₂Cl₂, and the organic layer is washed with water and NaHCO₃ aq. solution, followed by drying over anhydrous MgSO₄. After evaporating the solvent, the residue is purified by recrystallization from hexane-$CH_2Cl_2$. 10.4 g of a white solid are obtained (86%). $^1$H NMR ($CDCl_3$), δ[ppm]: d 2.50 (s, 3H), 4.23 (s, 2H), 7.22–7.27 (m, 5H), 7.32 (t, 2H), 7.91 (d, 2H)

35.2 1-(4-Methylsulfanyl-phenyl)-2-phenyl-ethanone oxime

Hydroxylammonium chloride (4.19 g, 60.2 mmol) and sodium acetate (7.42 g, 90.4 mmol) are dissolved in 20 ml of water. To this solution 9.72 g (40.1 mmol) of 1-(4-methylsulfanyl-phenyl)-2-phenyl-ethanone in 60 ml of ethanol are added. The reaction mixture is heated to reflux for 18.5 hr. The reaction mixture was concentrated by rotary evaporation and poured into water. The resulting white solid is filterd and washed with water. After drying under reduced pressure, recrystallization from hexane-$CH_2Cl_2$ affords 7.32 g of a white solid (71%). $^1$H NMR ($CDCl_3$), δ[ppm]: d 2.45 (s, 3H), 4.20 (s, 2H), 7.16–7.20 (m, 3H), 7.24–7.27 (m, 4H), 7.54 (d, 2H), 9.03 (s, 1H).

35.3 1-(4-Methylsulfanyl-phenyl)-2-phenyl-ethanone oxime O-acetate

To a solution of 1-(4-methylsulfanyl-phenyl)-2-phenyl-ethanone oxime (2.64 g, 10.3 mmol) and acetyl chloride (0.8 ml, 11.3 mmol) in THF (20 ml), pyridine (1.0 ml, 12.4 mmol) is added dropwise at 0° C. After stirring at room temperature overnight, the reaction mixture is poured into water. The products are extracted with THF, and the organic layer is washed with $NaH-CO_3$ aq. solution and brine, followed by drying over anhydrous $MgSO_4$. After filtration and evaporation of the solvent, the desired product is purified by column chromatography on silica gel with $CH_2Cl_2$ as eluent. 2.79 g of a white solid melting at 57–59° C. are obtained (91%). $^1$H NMR ($CDCl_3$), δ[ppm]: d 2.20 (s, 3H), 2.44 (s, 3H), 4.20 (s, 2H), 7.16–7.23 (m, 5H), 7.26 (dd, 2H), 7.67 (d, 2H).

EXAMPLE 36

1,9-Bis-(4-methylsulfanyl-phenyl)-nonane-1,2,8,9-tetraone 2,8-dioxime di(O-acetate)

In formula II: M=—$(CH_2)_5$—; $R_2$=—$COCH_3$; $R_3$, $R_4$, $R_6$, $R_7$,=H; $R_5$=—$SCH_3$

36.1 1,9-Bis-(4-methylsulfanyl-phenyl)-nonane-1,9-dione

Thioanisole (23.5 ml, 0.20 mol) is added to a suspension of $AlCl_3$ (27.3 g, 0.205 mol) in 200 ml of $CH_2Cl_2$. Azelaoyl chloride (19.7 ml, 0.10 mol) is added dropwise slowly, while the reaction mixture is cooled in an ice bath and the reaction solution is stirred for 19 h at room temperature. Then, the reaction solution is poured into ice-water. The produced white precipitate is filtered off and the crude product is extracted from the filtrate with $CH_2Cl_2$, washed with brine, dried over $MgSO_4$, and concentrated. The residue is purified by recrystallization from i-$Pr_2O$—$CHCl_3$. The product is obtained as a white solid. $^1$H NMR ($CDCl_3$), δ[ppm]: δ1.35–1.43 (m, 6H), 1.72 (t, 4H), 2.52 (s, 6H), 2.91 (t, 4H), 7.26 (d, 4H), 7.87 (d, 4H)

36.2 1,9-Bis-(4-methylsulfanyl-phenyl)-nonane-1,2,8,9-tetraone 2,8-dioxime 5.0 g (12.5 mmol) of 1,9-bis-(4-methylsulfanyl-phenyl)-nonane-1,9-dione are dissolved in 120 ml of t-butylmethyl ether and 200 ml of $CH_2Cl_2$. HCl-gas is bubbled through the mixture and successively methyl nitrite-gas is bubbled for 0.5 hr. After the bubbling is finished, the reaction solution is poured into water. The crude product is extracted with ethyl acetate, washed with water and brine, dried over $MgSO_4$, and concentrated. The residue is purified by recrystallization from methanol. The product is obtained as a slightly yellow solid. $^1$H NMR (DMSO-$d_6$), δ[ppm]: 1.25 (m, 2H), 1.41 (m, 4H), 2.45 (s, 6H), 2.50 (t, 4H), 7.24 (d, 4H), 7.69 (d, 4H).

36.3 1,9-Bis-(4-methylsulfanyl-phenyl)-nonane-1,2,8,9-tetraone 2,8-dioxime di(O-acetate)

Acetyl chloride (0.33 ml, 4.58 mmol) and triethylamine (0.91 ml, 6.54 mmol) are added to a solution of 1,9-bis-(4-methylsulfanyl-phenyl)-nonane-1,2,8,9-tetraone 2,8-dioxime (1.0 g, 2.18 mmol) in 35 ml of THF. After stirring at 0° C. for 3 h, the produced solid is filtered off. The crude product is concentrated and purified by column chromatography on silica gel with ethyl acetate-hexane (1:4 to 2:3) as an eluent. The product is obtained as a viscous oil. $^1$H NMR ($CDCl_3$), δ[ppm]: 1.40–1.49 (m, 2H), 1.52–1.64 (m, 4H), 2.25 (s, 6H), 2.52 (s, 6H), 2.76 (t, 4H), 7.26 (d, 4H), 7.98 (d, 4H).

EXAMPLE 37

1,9-Bis-(4-methylsulfanyl-phenyl)-nonane-1,9-dione dioxime di(O-acetate)

In formula IV: M=—$(CH_2)_7$—; $R_2$=—$COCH_3$; $R_4'$,$R_6'$=H; $R_5'$=—$SCH_3$

37.1 1,9-Bis-(4-methylsulfanyl-phenyl)-nonane-1,9-dione dioxime 8.0 g (20 mmol) of 1,9-bis-(4-methylsulfanyl-phenyl)-nonane-1,9-dione are dissolved in 400 ml of hot ethanol and 70 ml of hot THF. Then a solution of hydroxylammonium chloride (2.9 g, 42 mmol) and sodium acetate (5.6 g, 68 mmol) in 70 ml of water is added, and the reaction solution is stirred at 100° C. for 3 h. After cooling and concentrating, water is added. The crude product is extracted with ethyl acetate, washed with brine, dried over $MgSO_4$, and concentrated. The residue is purified by recrystallization from methanol. The product is obtained as white solid. $^1$H NMR ($CDCl_3$), δ[ppm]: 1.30–1.40 (m, 6H), 1.48–1.58 (m, 4H), 2.50 (s, 6H), 2.75 (t, 4H), 7.23 (d, 4H), 7.52 (d, 4H).

37.2 1,9-Bis-(4-methylsulfanyl-phenyl)-nonane-1,9-dione dioxime di(O-acetate)

Acetyl chloride (0.69 ml, 9.74 mmol) and triethylamine (1.9 ml, 13.9 mmol) are added to a solution of 1,9-bis-(4-methylsulfanyl-phenyl)-nonane-1,9-dione dioxime (2.0 g, 4.64 mmol) in 20 ml of THF. After stirring at 0° C. for 30 min, the produced solid is filtered off. The crude product is concentrated and purified by column chromatography on silica gel with ethyl acetate-hexane (1:4 to 2:3) as an eluent. The product is obtained as a viscous oil. $^1$H NMR ($CDCl_3$), δ[ppm]: 1.27–1.40 (m, 6H), 1.48–1.58 (m, 4H), 2.25 (s, 6H), 2.50 (s, 6H), 2.80 (t, 4H), 7.24 (d, 4H), 7.63 (d, 4H).

EXAMPLE 38

1-{4-[4-(2-acetoxyimino-butyryl)-phenylsulfanyl]-phenyl}-butane-1,2-dione 2-oxime O-acetate In formula I:

$R_1 = C_2H_5$; $R_2 = $ —COCH$_3$; $R_3$, $R_4$, $R_6$, $R_7 = H$; $R_5 = SR_9$;

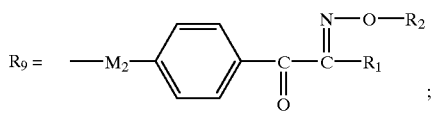

$M_2$=direct bond

38.1 1-[4-(4-Butyryl-phenylsulfanyl)-phenyl]-butan-1-one

Diphenylsulfide (33.3 ml, 0.20 mol) is added to a suspension of AlCl$_3$ (54.7 g, 0.41 mol) in 350 ml of CH$_2$Cl$_2$. n-Butyryl chloride (41.4 ml, 0.40 mol) is added dropwise slowly in an ice bath and the reaction solution is stirred at room temperature for 15 h. Then, the reaction solution is poured into ice-water. The crude product is extracted with CH$_2$Cl$_2$, washed with 1N NaOH and brine, dried over MgSO$_4$, and concentrated. The product is obtained as a white solid. $^1$H NMR (CDCl$_3$), δ[ppm]: 1.00 (t, 6H), 1.77 (tq, 4H), 2.92 (t, 4H), 7.40 (d, 4H), 7.90 (d, 4H).

38.2 1-{4-[4-(2-Hydroxyimino-butyryl)-phenylsulfanyl]-phenyl}-butane-1,2-dione 2-oxime 20 g (61 mmol) of 1-[4-(4-butyryl-phenylsulfanyl)-phenyl]-butan-1-one are dissolved in 300 ml of t-butylmethyl ether and 50 ml of CH$_2$Cl$_2$. HCl-gas is bubbled through the mixture and successively methyl nitrite-gas is bubbled for 0.5 hr. After the bubbling is finished, the reaction solution is poured into water. The crude product is extracted with ethyl acetate, washed with water and brine, dried over MgSO$_4$, and concentrated. The residue is purified by column chromatography on silica gel with ethyl acetate-hexane (1:8 to 1:3) as an eluent. The product is obtained as a yellow solid. $^1$H NMR (CDCl$_3$), δ[ppm]: 1.15 (t, 6H), 2.73 (q, 4H), 7.35 (d, 4H), 7.84 (d, 4H), 8.40 (bs, 2H).

38.3 1-{4-[4-(2-acetoxyimino-butyryl)-phenylsulfanyl]-phenyl}-butane-1,2-dione 2-oxime O-acetate Acetyl chloride (2.0 ml, 28.6 mmol) and triethylamine (5.7 ml, 40.8 mmol) are added to a solution of 1-{4-[4-(2-hydroxyimino-butyryl)-phenylsulfanyl]-phenyl}-butane-1,2-dione 2-oxime (5.0 g, 13.6 mmol) in 20 ml of THF. After stirring at 0° C. for 30 min, the produced solid is filtered off. The crude product is concentrated and purified by column chromatography on silica gel with ethyl acetate-hexane (1:8 to 1:3) as an eluent. The product is obtained as a slightly yellow oil. $^1$H NMR (CDCl$_3$), δ[ppm]: 1.18 (t, 6H), 2.27 (s, 6H), 2.80 (q, 4H), 7.44 (d, 4H), 8.04 (d, 4H).

EXAMPLE 39

1-{4-[4-(2-benzoxyimino-butyryl)-phenylsulfanyl]-phenyl}-butane-1,2-dione 2-oxime O-benzoate In formula I $R_1 = C_2H_5$; $R_2 = $ —CO-phenyl; $R_3$, $R_4$, $R_6$, $R_7 = H$; $R_5 = SR_9$;

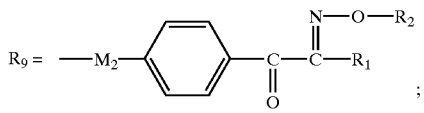

$M_2$=direct bond

Benzoyl chloride (4.72 ml, 40.7 mmol) and triethylamine (8.5 ml, 61 mmol) are added to a solution of 1-{4-[4-(2-hydroxyimino-butyryl)-phenylsulfanyl]-phenyl}-butane-1,2-dione 2-oxime (7.45 g, 20.3 mmol) in 40 ml of THF. After stirring at 0° C. for 50 min, the reaction solution is poured into water. The crude product is extracted with ethyl acetate, washed with water, dried over MgSO$_4$, and concentrated. The residue is purified by column chromatography on silica gel with ethyl acetate-hexane-CH$_2$Cl$_2$ (1:9:0 to 1:3:1) as an eluent. The product is obtained as a slightly yellow solid, melting at 110–113° C. $^1$H NMR (CDCl$_3$), δ[ppm]: 1.28 (t, 6H), 2.93 (q, 4H), 7.45–7.56 (m, 8H), 7.65 (t, 2H), 8.08–8.18 (m, 8H).

EXAMPLE 40

1-{4-[4-(1-Acetoxyimino-butyl)-phenylsulfanyl]-phenyl}-butan-1-one oxime O-acetate In formula III:

$R_1' = C_3H_7$; $R_2 = $ —COCH$_3$; $R_4'$, $R_6'$, = H; $R_5 = SR_9$;

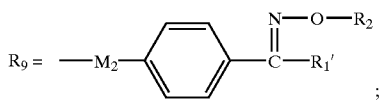

$M_2$=direct bond

40.1 1-{4-[4-(1-Hydroxyimino-butyl)-phenylsulfanyl]-phenyl}-butan-1-one oxime 20 g (61.3 mmol) of 1-[4-(4-butyryl-phenylsulfanyl)-phenyl]-butan-1-one are dissolved in 140 ml of hot ethanol. Then a solution of hydroxylammonium chloride (8.55 g, 123 mmol) and sodium acetate (17.1 g, 208 mmol) in 70 ml of water is added, and the reaction solution is stirred at 100° C. for 2 h. After cooling and concentrating, water is added. The crude product is extracted with ethyl acetate, washed with brine, dried over MgSO$_4$, and concentrated. The residue is purified by recrystallization from methanol. The product (an isomeric mixture) is obtained as white solid. <major isomer> $^1$H NMR (CDCl$_3$), δ[ppm]: 0.98 (t, 6H), 1.61 (tq, 4H), 2.76 (t, 4H), 7.34 (d, 4H), 7.55 (d, 4H).

40.2 1{4-[4-(1-Acetoxyimino-butyl)-phenyslulfanyl]-phenyl}-butan-1-one oxime O-acetate Acetyl chloride (2.1 ml, 29.4 mmol) and triethylamine (5.9 ml, 42 mmol) are added to a solution of 1-{4-[4-(1-hydroxyimino-butyl)-phenylsulfanyl]-phenyl}-butan-1-one oxime (5.0 g, 14.0 mmol) in 40 ml of THF. After stirring at 0° C. for 30 min, the produced solid is filtered off. The crude product is concentrated and purified by column chromatography on silica gel with ethyl acetate-hexane (1:4 to 2:5) as an eluent. The product is obtained as a colorless oil. $^1$H NMR (CDCl$_3$), δ[ppm]: 0.99 (t, 6H), 1.60 (tq, 4H), 2.26 (s, 6H), 2.81 (t, 4H), 7.35 (d, 4H), 7.66 (d, 4H).

EXAMPLE 41

2,4-Diethyl-thioxanthen-9-one oxime O-benzoate

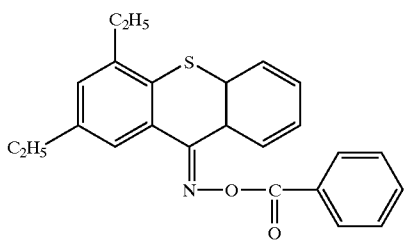

(R$_1$')

is SR$_9$ forming a ring via the radical R$_9$ with a carbon atom of the phenyl ring bearing the groups R$_4$' and R$_6$')

41.1 2,4-Diethyl-thioxanthen-9-one oxime 7.0 g (26 mmol) of diethylthioxanthen-9-one are dissolved in 15 ml of hot ethanol and 15 ml of pyridine. Then hydroxylammonium chloride (3.6 g, 52 mmol) is added, and the reaction solution is stirred at 115° C. for 21 h. After cooling, water is added. The crude product is extracted with ethyl acetate, washed with water, dried over MgSO$_4$, and concentrated. The residue is purified by column chromatography on silica gel with ethyl acetate-hexane (1:30 to 1:10) as an eluent. The product (an isomeric mixture) is obtained as a slightly yellow solid. $^1$H NMR (CDCl$_3$), δ[ppm]: 1.23–1.32 (m, 6H), 2.65–2.72 (m, 2H), 2.77–2.86 (m, 2H), 7.12(s, 1H), 7.30–7.36 (m, 2H), 7.45 (dd, 1/2H), 7.53–7.55 (m, 1H), 7.80 (dd, 1/2H), 8.03 Cd, 1/2H), 8.09–8.48 (bs, 1H), 8.34 (dd, 1/2H), wherein 1/2H means 1H of either isomer.

41.2 2,4-Diethyl-thioxanthen-9-one oxime O-benzoate

Benzoyl chloride (1.1 ml, 9.9 mmol) and triethylamine (1.9 ml, 13.5 mmol) are added to a solution of 2,4-diethyl-thioxanthen-9-one oxime (2.56 g, 9.0 mmol) in 10 ml of THF. After stirring at 0° C. for 70 min, the reaction solution is poured into water. The crude product is extracted with ethyl acetate, washed with water, dried over MgSO$_4$, and concentrated. The residue is purified by column chromatography on silica gel with ethyl acetate-hexane (1:20 to 1:8) as an eluent. The product (an isomeric mixture) is obtained as a yellow solid. $^1$H NMR (CDCl$_3$), δ[ppm]: 1.24–1.36 (m, 6H), 2.71–2.76 (q, 2H), 2.81–2.90 (m, 2H), 7.20 (d, 1/2H), 7.23 (d, 1/2H), 7.38–7.54 (m, 4H+1/2H), 7.59–7.65 (m, 1H+1/2H), 7.87 (m, 1/2H), 7.94 (m, 1/2H), 8.08 (t, 2H), 8.16 (dd, 1/2H), 8.22 (dd, 1/2H), wherein 1/2H means 1H of either isomer.

EXAMPLE 42

A photocurable formulation is prepared by mixing the following components:
  200.0 parts by weight of acrylated acrylcopolymer ($^{RTM}$ACA200M, provided by Daicel Industries, Ltd.)
  15.0 parts by weight of dipentaerythritol hexaacrylate ((DPHA), provided by UCB Chemicals),
  2.3 parts by weight of the photoinitiator to be tested.

All operations are carried out under yellow light. The formulations are applied to an aluminum plate. The solvent is removed by heating at 80° C. for 15 minutes in a convection oven. The thickness of the dry film is 25 μm. To this coating an acetate film is applied, over which a standardized test negative with 21 steps of different optical density (Stouffer step wedge) is placed. The sample is covered with a second UV-transparent film and pressed onto a metal plate by means of vacuum. Exposure is carried out in a first test series for 40 seconds, in a second series for 80 seconds and in a third series for 160 seconds, using a 3 kW metal halide lamp (ORC, model SMX 3000) at a distance of 60 cm. Following exposure, the cover films and the mask are removed and the exposed film is developed with 1% sodium carbonate aqueous solution for 180 sec. at 30° C. by using a spray type developer (Walter Lemmen, model T21). The sensitivity of the initiator system used is characterized by indicating the highest step number which remained (i.e. polymerized) after developing. The higher the number of steps, the more sensitive is the system tested. A further test series is provided, adding 0.23 part by weight of a mixture of 2-isopropylthio-xanthone and 4-isopropylthioxanthone ($^{RTM}$QUANTACURE ITX, International Biosynthetics) to the above described formulation. The results are collected in table 2.

TABLE 2

| Photoinitiator of example | Sensitizer | Number of steps reproduced after exposure time of | | |
|---|---|---|---|---|
| | | 40 sec. | 80 sec. | 160 sec. |
| 1 | — | 15 | 17 | 19 |
| 2 | — | 11 | 13 | 15 |
| 3 | — | 10 | 12 | 14 |
| 5 | — | 14 | 16 | 19 |
| 7 | — | 12 | 14 | 17 |
| 7 | Quantacure ITX | 13 | 15 | 17 |
| 8 | — | 12 | 14 | 17 |
| 10 | — | 15 | 17 | 20 |
| 11 | — | 12 | 14 | 16 |
| 12 | — | 12 | 14 | 15 |
| 13 | — | 12 | 14 | 15 |
| 14 | — | 15 | 17 | 19 |
| 15 | — | 12 | 14 | 16 |
| 18 | — | 10 | 12 | 14 |
| 19 | — | 10 | 12 | 14 |
| 20 | — | 11 | 13 | 15 |
| 29 | Quantacure ITX | 10 | 12 | 14 |
| 21 | — | 12 | 14 | 16 |

EXAMPLE 43

A photocurable formulation, which serves as a model for a dry film etch resist is prepared by mixing the following components:

45.1 parts by weight of $^{RTM}$SCRIPSET 540 (styrene-maleic anhydride copolymer, provided By Monsanto)
  48.3 parts by weight of trimetylolpropane triacrylate
  6.6 parts by weight of pentaethyleneglycol diacrylate
  105.2 parts by weight of acetone To that mixture 0.25 % (based on the solid content) of $^{RTM}$QUANTACURE ITX, 0.14% (based on the solid content) of bis(diethylamino) benzophenone and 3% (based on the solid content) of the initiator to be tested are added and stirred. All operations are carried out under yellow light conditions. The sample to which initiator has been added is applied to an aluminum foil. The solvent is removed by drying at 60° C. for 15 minutes in a convection oven. After drying the film thickness is 35–40 μm. A 76 μm thick polyester film is laminated onto the dry film and a standardized tetst negative with 21 steps of different optical density (Stouffer wedge) is placed on top. The sample is covered with a second UV-transparent film and pressed onto a metal plate by means of vacuum. Exposure is carried out in a first test series for 10 seconds, in a second series for 20 seconds and in a third series for 40 seconds, using a 5 kW metal halide lamp (MO61, Staub AG) at a distance of 30 cm. Following exposure, the cover films and the mask are removed and the exposed film is developed with 0.85% sodium carbonate aqueous solution for 8 minutes at 35° C. by using a spray type developer (Walter Lemmen, model T21). The sensitivity of the initiator system used is characterized by indicating the highest step number which remained (i.e. polymerized) after developing. The higher the number of steps, the more sensitive is the tested system.

TABLE 3

| Photoinitiator of example | Number of steps reproduced after exposure time of | | |
|---|---|---|---|
| | 10 sec. | 20 sec. | 40 sec. |
| 29 | 12 | 14 | 16 |
| 21 | 13 | 15 | 17 |
| 23 | 12 | 14 | 16 |

EXAMPLE 44

Preparation of Poly(benzylmethacrylate-co-methacrylic acid) 24 g of benzylmethacrylate, 6 g of methacrylic acid and 0.525 g of azobisisobutyronitrile (AIBN) are dissolved in 90 ml of propylene glycol 1-monomethyl ether 2-acetate (PGMEA). The resulting reaction mixture is placed in a preheated oil bath at 80° C. After stirring for 5 hours at 80° C. under nitrogen, the resulting viscous solution is cooled to room temperature and used without further purification. The solid content is about 25%.

A photocurable composition is prepared by mixing the following components:

200.0 parts by weight of copolymer of benzylmethacrylate and methacrylic acid (benzylmethacrylate:methacrylic acid=80:20 by weight) 25% propylene glycol 1-monomethyl ether 2-acetate (PGMEA) solution, prepared as described above;

50.0 parts be weight of dipentaerythritol hexaacrylate ((DPHA), provided by UCB Chemicals);

4.0 parts be weight of photoinitiator; and 150.0 parts by weight of PGMEA.

All operations are carried out under yellow light. The compositions are applied to an aluminum plate using an electric applicator with a wire wound bar. The solvent is removed by heating at 100° C. for 2 minutes in a convection oven. The thickness of the dry film is approximately 2 μm. To this coating an an acetate film is applied, over which a standardized test negative with 21 steps of different optical density (Stouffer step wedge) is placed. The sample is covered with a second UV-transparent film and pressed onto a metal plate by means of vacuum. Interference filters are placed on the top to select the wavelengths at 365 nm and 405 nm. Exposure is carried out using a 250W super high pressure mercury lamp (USHIO, USH-250By) at adistance of 15 cm. After exposure, the cover films and the mask are removed and the exposed film is developed with 1% sodium carbonate aqueous solution for 200 sec. at 30° C. by using a spray type developer (Walter Lemmen, model T21). The sensitivity of the initiator system used is characterized by the minimum dose required to cure upon irradition at each wavelength, which is calculated from the transmittance of the step with the highest number that is cured. The smaller the dose, the more sensitive is the tested initiator system at the selected wavelength. The results are collected in table 4.

TABLE 4

| Photoinitiator of example | Sensitizer | Sensitivity [mJ/cm$^2$] | |
|---|---|---|---|
| | | at 365 nm | at 405 nm |
| 2 | — | 4 | 161 |
| 2 | S-1 | 4 | 29 |
| 4 | — | 129 | >1000 |
| 4 | S-1 | 129 | 323 |
| 6 | — | 6 | 161 |
| 6 | S-1 | 6 | 20 |
| 9 | — | 46 | >1000 |
| 9 | S-1 | 8 | 29 |
| 13 | — | 4 | 57 |
| 13 | S-1 | 11 | 29 |
| 25 | — | 523 | >1000 |
| 25 | S-1 | 182 | 645 |
| 27 | — | >1000 | >1000 |
| 27 | S-1 | 65 | 114 |
| 28 | — | >1000 | >1000 |
| 28 | S-1 | 8 | 14 |
| 30 | — | 182 | >1000 |
| 30 | S-1 | 6 | 14 |
| 21 | — | 4 | 114 |
| 21 | S-1 | 4 | 14 |

S-1 is 4,4'-Bis(diethylamino)benzophenone (added in 2.4 parts by weight)

EXAMPLE 45

A photocurable composition is prepared by mixing the following components:

200.0 parts by weight of a copolymer of benzylmethacrylate and methacrylic acid (benzylmethacrylate:methacrylic acid=80:20 by weight) 25% propylene glycol 1-monomethyl ether 2-acetate (PGMEA) solution, prepared as described in example 33;

50.0 parts by weight of dipentaerythritol hexaacrylate ((DPHA), provided by UCB Chemicals), 2.0 parts by weight of photoinitiator, and 150.0 parts by weight of PGMEA All operations are carried out under yellow light. The compositions are applied to an aluminum applicator with a wire wound bar. The solvent is removed by heating at 100° C. minutes in a convection oven. The thickness of the dry film is approximately 2 μm. A standardized test negative film with 21 steps of different optical density (Stouffer step wedge) is placed with an air gap of around 100 μm between the film and the resist. An interference filter is placed on the top to select the wavelength at 365 nm. Exposure is carried out using a 250 W super high pressure mercury lamp (USHIO, USH-250BY) at a distance of 15 cm. After exposure, the exposed film is developed with 1% sodium carbonate aqueous solution for 200 sec. at 30° C. by using a spray type developer (Walter Lemmen, model T21). The sensitivity of the initiator system used is characterized by the minimum dose required to cure upon irradiation at each wavelength, which is calculated from the transmittance of the step with the highest number that is cured. The smaller the dose, the more sensitive is the tested initiator system at the selected wavelength. The results are listed in table 5

TABLE 5

| Photoinitiator of example | Sensitizer | Sensitivity [mJ/cm$^2$] at 365 nm |
|---|---|---|
| 21 | — | 57 |
| 21 | S-1 | 114 |
| 21 | S-2 | 57 |

S-1 is 4,4'-Bis(diethylamino)benzophenone (added in 1.2 parts by weight)
S-2 is Coumarin 106

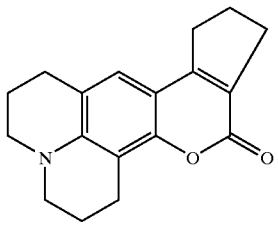

(added in 1.2 parts by weight)

EXAMPLE 46

A polyamic acid ester is prepared from oxydiphthalic acid dianhydride, methacrylic acid -2 hydroxyethylester and 4,4'-diaminodiphenylether according to example I.1. of EP 624826. The intrinsic viscosity is 0.3 dl/g and the average molecular weights are Mw=2550 g/mol and Mn=3800 g/mol. A formulation is prepared by dissolving 16.97 g of the above precursor, 2.545 g of tetraethylene glycol dimethacrylate (SR 209, Cray Valley), and 0.85 g of the compound of example 21 in 29.52 g of N-methyl pyrrolidinone. The formulation is spin-coated onto a silicon wafer with a spin cycle of 5 seconds at 1500 rpm for spreading, followed by 30 seconds at 5000 rpm. The coated wafer is dried for 5 minutes at 100° C. on a hot plate. A photosensitive tack-free film of 6 μm thickness is obtained. The wafer is then exposed through a step-wedge using an ORIEL (Model 87532) exposure tool equipped with a 350 W mercury arc either through a 365 nm narrow bandpass filter or the full arc spectrum. Vacuum contact of the step wedge mask is obtained on a vacuum table using a polyester foil covering the substrate and the stepwedge mask. Intensities are measured using a OAI power meter equipped with a 365 nm sensor. The exposed film is immersion developed in cyclopentanone for 60 seconds, rinsed two times with a 1:1 mixture of cyclopentanone/isopropanol for 10 seconds and finally with pure isopropanol for 10 seconds. With monochromatic exposure at 365 nm, a dose of 28 mJ/cm$^2$ is necessary to cross-link the film sufficiently to make it insoluble in the developer. Using the full spectrum of the mercury arc a dose of 38 mJ/cm$^2$ is needed to crosslink the film so that it does not dissolve in the developer.

EXAMPLE 47

A formulation is prepared by mixing 16.97 g of the polyimide precursor described in example A, 2.545 g of tetraethylene glycol dimethacrylate ($^{RTM}$SR 209, Cray Valley), 0.85 g of the initiator of example 29, 0.17 g of Michler's Ketone and 29.52 g of N-methyl pyrrolidinone. The formulation is spin-coated onto a silicon wafer with a spin cycle of 5 seconds at 1500 rpm for spreading, followed by 30 seconds at 5000 rpm. The coated wafer is dried for 5 minutes at 100° C. on a hot plate A photosensitive tack-free film of 6 μm thickness is obtained. The wafer is then exposed through a step-wedge using an ORIEL (Model 87532) exposure tool equipped with a 350 W mercury arc either through a 365 nm narrow band pass filter or the full arc spectrum. Vacuum contact of the step wedge mask is obtained on a vacuum table using a polyester foil covering the substrate and the stepwedge mask. Intensities are measured using a OAI power meter equipped with a 365 nm sensor. The exposed film is immersion developed in cyclopentanone for 60 seconds, rinsed two times with a 1:1 mixture of cyclopentanone/isopropanol for 10 seconds and finally with pure isopropanol for 10 seconds. With monochromatic exposure at 365 nm, a dose of 36 mJ/cm$^2$ is necessary to make the film insoluble in the developer. Using the full spectrum a dose of 75 mJ/cm$^2$ is needed to crosslink the film so that it does not dissolve in the developer.

What is claimed is:

1. Compounds of the formulae I, II, III and IV

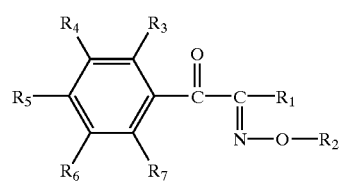

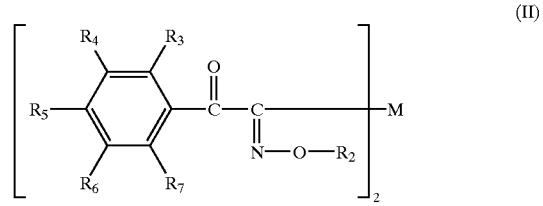

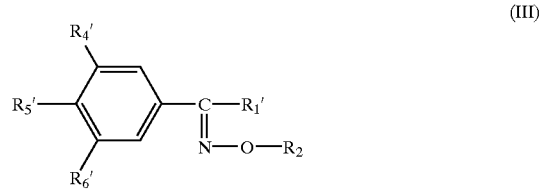

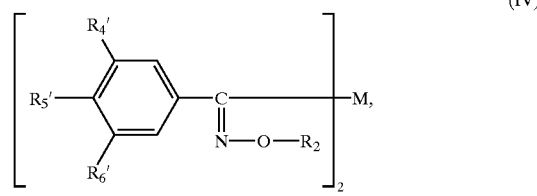

wherein
$R_1$ is phenyl which is unsubstituted or substituted by one or more $C_1$–$C_6$alkyl, phenyl, halogen, $OR_8$, $SR_9$ or $NR_{10}R_{11}$; or $R_1$ is $C_1$–$C_{20}$alkyl or $C_2$–$C_{20}$alkyl optionally interrupted by one or more —O— and/or optionally substituted by one or more hydroxyl groups; or $R_1$ is $C_5$–$C_8$cycloalkyl, $C_2$–$C_{20}$alkanoyl; or benzoyl which is unsubstituted or substituted by one or more $C_1$–$C_6$alkyl, phenyl, $OR_8$, $SR_9$ or $NR_{10}R_{11}$; or $R_1$ is $C_2$–$C_{12}$alkoxycarbonyl optionally interrupted by one or more —O— and/or optionally substituted by one or more hydroxyl groups; or $R_1$ is phenoxycarbonyl which is unsubstituted or substituted by $C_1-C_6$alkyl, halogen, phenyl, $OR_8$ or $NR_{10}R_{11}$; or $R_1$ is —$CONR_{10}R_{11}$, CN, $NO_2$, $C_1-C_4$haloalkyl, $S(O)_mC_1-C_6$alkyl; unsubstituted or $C_1-C_{12}$alkyl-substituted $S(O)_m$—$C_6-C_{12}$aryl; $SO_2O$—$C_1-C_6$alkyl, $SO_2O$—$C_6-C_{10}$aryl, or diphenyl-phosphinoyl; m is 1 or 2;

$R_1'$ is $C_2-C_{12}$alkoxycarbonyl optionally interrupted by one or more —O— and/or optionally substituted by one or more hydroxyl groups; or $R_1'$ is phenoxycarbonyl which is unsubstituted or substituted by one or more $C_1-C_6$alkyl, halogen, phenyl, $OR_8$ or $NR_{10}R_{11}$; or $R_1'$ is $C_5-C_8$cycloalkyl, —$CONR_{10}R_{11}$, CN; or phenyl which is substituted by $SR_9$, wherein optionally a 5- or 6-membered ring is formed via the group $R_9$ by building a link to a carbon atom of the phenyl ring bearing the groups $R_4'$, $R_5'$ and $R_6'$; or, if at least one of $R_4'$, $R_5'$ or $R_6'$ is —$SR_9$, $R_1'$ additionally is $C_1-C_{12}$alkyl which is unsubstituted or substituted by one or more halogen, OH, $OR_2$, phenyl, halogenated phenyl or phenyl substituted by $SR_9$, and which $C_1-C_{12}$alkyl optionally is interrupted by —O— or —NH—(CO)—;

$R_2$ is $C_2-C_{12}$alkanoyl which is unsubstituted or substituted by one or more halogen or CN; or $R_2$ is $C_4-C_6$alkenoyl, provided that the double bond is not conjugated with the carbonyl group; or $R_2$ is benzoyl which is unsubstituted or substituted by one or more $C_1-C_6$alkyl, halogen, CN, $OR_8$, $SR_9$ or $NR_{10}R_{11}$; or $R_2$ is $C_2-C_6$alkoxycarbonyl; or phenoxycarbonyl which is unsubstituted or substituted by $C_1-C_6$alkyl or halogen;

$R_3$, $R_4$, $R_5$, $R_6$ and $R_7$ independently of one another are hydrogen, halogen, $C_1-C_{12}$alkyl, cyclopentyl, cyclohexyl; or phenyl which is unsubstituted or substituted by one or more $OR_8$, $SR_9$ or $NR_{10}R_{11}$; or $R_3$, $R_4$, $R_5$, $R_6$ and $R_7$ are benzyl, benzoyl, $C_2-C_{12}$alkanoyl; $C_2-C_{12}$alkoxycarbonyl optionally interrupted by one or more —O— and/or optionally substituted by one or more hydroxyl groups; or $R_3$, $R_4$, $R_5$, $R_6$ and $R_7$ are phenoxycarbonyl or a group $OR_8$, $SR_9$, $SOR_9$, $SO_2R_9$ or $NR_{10}R_{11}$, wherein the substituents $OR_8$, $SR_9$ and $NR_{10}R_{11}$ optionally form 5- or 6-membered rings via the radicals $R_8$, $R_9$, $R_{10}$ and/or $R_{11}$ with further substituents on the phenyl ring or with one of the carbon atoms of the phenyl ring;

provided that at least one of the groups $R_3$, $R_4$, $R_5$, $R_6$ or $R_7$ is $SR_9$ or $NR_{10}R_{11}$;

$R_4'$, $R_5'$ and $R_6'$ independently of one another are hydrogen, halogen, $C_1-C_{12}$alkyl, cyclopentyl, cyclohexyl; phenyl which is unsubstituted or substituted by $OR_8$, $SR_9$ or $NR_{10}R_{11}$; or $R_4'$, $R_5'$ and $R_6'$ are benzyl, benzoyl, $C_2-C_{12}$alkanoyl; $C_2-C_{12}$alkoxycarbonyl optionally interrupted by one or more —O— and/or optionally substituted by one or more hydroxyl groups; or $R_4'$, $R_5'$ and $R_6'$ are phenoxycarbonyl; or are a group $OR_8$, $SR_9$, $SOR_9$, $SO_2R_9$, $NR_{10}R_{11}$, wherein the substituents $OR_8$, $SR_9$ and $NR_{10}R_{11}$ optionally form 5- or 6-membered rings via the radicals $R_8$, $R_9$, $R_{10}$ and/or $R_{11}$ with further substituents on the phenyl ring or with one of the carbon atoms of the phenyl ring;

provided that at least one of $R'_4$, $R'_5$ and $R'_6$ is $SR_9$ or $NR_{10}R_{11}$;

$R_8$ is hydrogen, $C_1-C_{12}$alkyl; or $C_2-C_6$alkyl which is substituted by —OH, —SH, —CN, $C_1-C_4$alkoxy, $C_3-C_6$alkenoxy, —$OCH_2CH_2CN$, —$OCH_2CH_2(CO)O(C_1-C_4$alkyl), —$O(CO)$—$C_1-C_4$alkyl, —$O(CO)$-phenyl, —(CO)OH or —(CO)O($C_1-C_4$alkyl); or $R_8$ is $C_2-C_6$alkyl which is interrupted by one or more —O—; or $R_8$ is —$(CH_2CH_2O)_nH$, $C_2-C_8$alkanoyl, $C_3-C_{12}$alkenyl, $C_3-C_6$alkenoyl, cyclohexyl; or phenyl which is unsubstituted or substituted by halogen, $C_1-C_{12}$alkyl or $C_1-C_4$alkoxy; or $R_8$ is phenyl-$C_1-C_3$alkyl, $Si(C_1-C_8$alkyl$)_r$(phenyl$)_{3-r}$, or a group

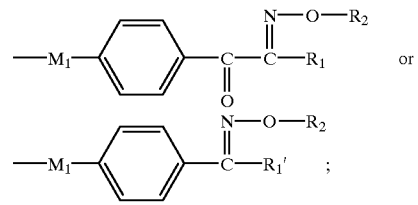

n is 1–20;
r is 1, 2 or 3;

$R_9$ is hydrogen, $C_1-C_{12}$alkyl, $C_3-C_{12}$alkenyl, cyclohexyl; $C_2-C_6$alkyl which is substituted by —OH, —SH, —CN, $C_1-C_4$alkoxy, $C_3-C_6$alkenoxy, —$OCH_2CH_2CN$, —$OCH_2CH_2(CO)O(C_1-C_4$alkyl), —$O(CO)$—$C_1-C_4$alkyl, —$O(CO)$-phenyl, —(CO)OH or —(CO)O($C_1-C_4$alkyl); or $R_9$ is $C_2-C_{12}$alkyl which is interrupted by one or more —O— or —S—; or $R_9$ is phenyl which is unsubstituted or substituted by halogen, $C_1-C_{12}$alkyl or $C_1-C_4$alkoxy; or $R_9$ is phenyl-$C_1-C_3$alkyl or a group

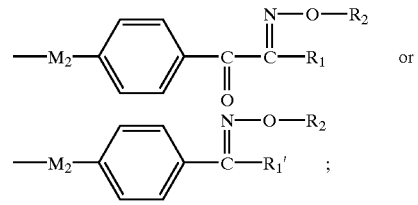

$R_{10}$ and $R_{11}$ independently of each other are hydrogen, $C_1-C_{12}$alkyl, $C_2-C_4$hydroxyalkyl, $C_2-C_{10}$alkoxyalkyl, $C_3-C_5$alkenyl, $C_5-C_{12}$cycloalkyl, phenyl-$C_1-C_3$alkyl; phenyl which is unsubstituted or substituted by $C_1-C_{12}$alkyl or $C_1-C_4$alkoxy; or $R_{10}$ and $R_{11}$ are $C_2-C_3$alkanoyl, $C_3-C_6$alkenoyl or benzoyl; or $R_{10}$ and $R_{11}$ together are $C_2-C_6$alkylene optionally interrupted by —O— or —$NR_8$— and/or optionally substituted by hydroxyl, $C_1-C_4$alkoxy, $C_2-C_4$alkanoyloxy or benzoyloxy; or, when $R_{10}$ is hydrogen, $R_{11}$ may be a group of formula

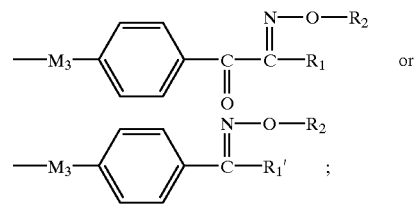

M is $C_1-C_{12}$alkylene, cyclohexylene, phenylene, —(CO)O—($C_2-C_{12}$alkylene)-O(CO)—, —(CO)O—($CH_2CH_2O)_n$—(CO)— or —(CO)—($C_2-C_{12}$-alkylene)—(CO)—;

$M_1$ is a direct bond; or $C_1-C_{12}$alkyleneoxy-, optionally interrupted by 1 to 5 —O—, —S— and/or —$NR_{10}$—;

$M_2$ is a direct bond; or $C_1$–$C_{12}$alkylene-S—, optionally interrupted by 1 to 5 —O—, —S— and/or —$NR_{10}$—;

$M_3$ is a direct bond, a piperazino group; or $C_1$–$C_{12}$alkylene-NH— optionally interrupted by 1 to 5 —O—, —S— and/or —$NR_{10}$—;

provided that
(i) if $R_5$ is methoxy and $R_2$ is benzoyl or acetyl, then $R_1$ is not phenyl;
(ii) if $R_5$ is methoxy and $R_1$ is ethoxycarbonyl, then $R_2$ is not benzoyl or ethoxycarbonyl;
(iii) if $R_5$ is methoxy and $R_1$ is 4-methoxybenzoyl, then $R_2$ is not ethoxycarbonyl;
(iv) if $R_5$ is methacryloylamino and $R_1$ is methyl, then $R_2$ is not benzoyl;
(v) if both, $R_5$ and $R_4$ or $R_5$ and $R_6$, are $OR_8$ and these $OR_8$ groups together form a ring via $R_8$ and thereby give —O—$CH_2$—O—, and $R_1$ is methyl, then $R_2$ is not acetyl;
(vi) if $R_4$, $R_5$ and $R_6$ simultaneously are methoxy and $R_1$ is ethoxycarbonyl, then $R_2$ is not acetyl;
(vii) if $R_5$ is methoxy and simultaneously $R_4$ or $R_6$ are acetoxy and $R_1$ is ethyl, then $R_2$ is not acetyl;
(viii) if, in formula III, $R_1'$ is methyl, $R_5'$ is phenylthio, and $R_4'$ and $R_6'$ both are H, then $R_2$ is not 4-chlorobenzoyl.

2. Compounds of formula I and III according to claim 1, wherein $R_1$ is phenyl which is unsubstituted or substituted by $C_1$–$C_6$alkyl, phenyl, $OR_8$, $SR_9$ or $NR_{10}R_{11}$; or $R_1$ is $C_1$–$C_{20}$alkyl, optionally interrupted by one or more —O— and/or optionally substituted by one or more hydroxyl groups; or $R_1$ is $C_1$–$C_4$haloalkyl;

$R_1'$ is phenoxycarbonyl which is unsubstituted or substituted by $C_1$–$C_6$alkyl, halogen, phenyl, $OR_8$, $NR_{10}R_{11}$; or $R_1'$ is —$CONR_{10}R_{11}$; or, if at least one of $R_4'$, $R_5'$ or $R_6'$ is —$SR_9$, $R_1'$ additionally is $C_1$–$C_{12}$alkyl which is unsubstituted or substituted by one or more halogen, OH, $OR_2$, phenyl, halogenated phenyl or phenyl substituted by $SR_9$, and which $C_1$–$C_{12}$alkyl optionally is interrupted by —O— or —NH—(CO)—;

$R_2$ is $C_2$–$C_{12}$alkanoyl which is unsubstituted or substituted by halogen; or $R_2$ is $C_4$–$C_6$alkenoyl provided that the double bond is not conjugated with the carbonyl group; or $R_2$ is benzoyl which is unsubstituted or substituted by one or more $C_1$–$C_6$alkyl or halogen;

$R_3$ and $R_7$ are hydrogen;

$R_4$, $R_6$, $R_4'$ and $R_6'$ independently of one another are hydrogen, halogen, $C_1$–$C_{12}$alkyl, $OR_8$ or $SR_9$, wherein the substituents $OR_8$ and $SR_9$ optionally form 5- or 6-membered rings via the radicals $R_8$ and/or $R_9$ with further substituents on the phenyl ring or with one of the carbon atoms of the phenyl ring; and $R_5$ and $R_5'$ are $OR_8$ or $SR_9$.

3. Compounds of formula I and III according to claim 1, wherein $R_3$, $R_4$ and $R_7$ or $R_4'$ and $R_6'$ are hydrogen and $R_5$ or $R_5'$ is $SR_9$.

4. Compounds of formula I according to claim 1, wherein $R_3$ and $R_7$ are hydrogen and $R_4$ and $R_5$ both are $OR_8$.

5. Compounds of formula III according to claim 1, wherein $R_1'$ is $C_1$–$C_{12}$alkyl which is unsubstituted or substituted by halogen or phenyl.

6. Compounds according to claim 1 of formula I, II, III or IV wherein $R_1$ is phenyl or $C_1$–$C_{12}$alkyl;

$R_1'$ is $C_2$–$C_4$alkoxycarbonyl, or phenyl which is substituted by $SR_9$, wherein a 5- or 6-membered ring is formed via the group $R_9$ by building a link to a carbon atom of the phenyl ring bearing the groups $R_4'$, $R_5'$ and $R_6'$; or, if at least one of $R_4'$, $R_5'$ or $R_6'$ is —$SR_9$, $R_1'$ is $C_1$–$C_{12}$alkyl substituted by phenyl or one or more fluorine;

$R_2$ is $C_2$–$C_4$alkanoyl, or benzoyl which is unsubstituted or substituted by one or more $C_1$–$C_4$alkyl or halogen;

$R_3$, $R_6$ and $R_7$ are hydrogen;

$R_4$ and $R_5$ independently of one another are hydrogen or a group $OR_8$, $SR_9$, or $NR_{10}R_{11}$;

$R_4'$ and $R_5'$ independently of one another are hydrogen or a group $OR_8$, $SR_9$, or $NR_{10}R_{11}$;

$R_6'$ is hydrogen;

$R_8$ and $R_9$ are $C_1$–$C_4$alkyl, phenyl or a group

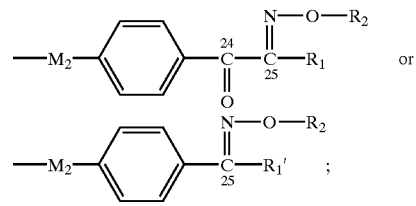

$R_{10}$ and $R_{11}$ are methyl or ethyl, or $R_{10}$ and $R_{11}$ together are $C_2$–$C_6$alkylene which is interrupted by —O—

M is $C_1$–$C_{12}$alkylene; and $M_2$ is a direct bond.

7. A color filter prepared by providing red, green and blue picture elements and a black matrix, all comprising a photosensitive resin and a pigment on a transparent substrate and providing a transparent electrode either on the surface of the substrate or on the surface of the color filter layer, wherein said photosensitive resin comprises a polyfunctional acrylate monomer, an organic polymer binder and a photopolymerization initiator of formula I, II, III or IV according to claim 1.

8. A photopolymerizable composition comprising
(a) at least one ethylenically unsaturated photopolymerizable compound and
(b) as photoinitiator, at least one compound of the formula I, II, III and/or

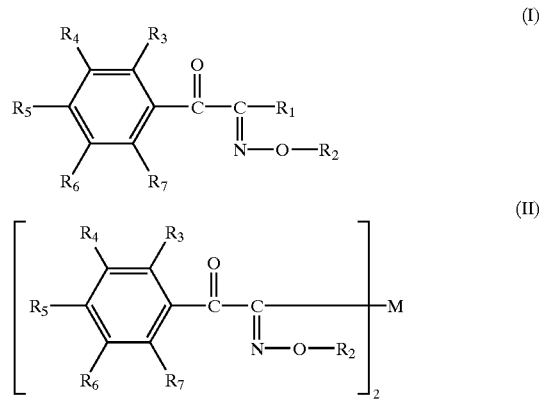

-continued

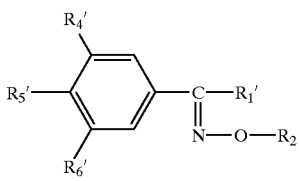
(III)

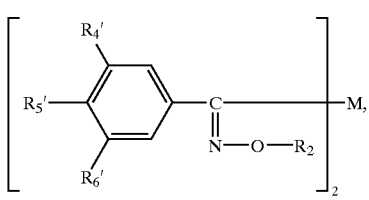
(IV)

wherein
R₁ is phenyl which is unsubstituted or substituted by one or more $C_1$–$C_6$alkyl, phenyl, halogen, $OR_8$, $SR_9$ or $NR_{10}R_{11}$; or R₁ is $C_5$–$C_8$cycloalkyl, $C_1$–$C_{20}$alkyl; or $C_2$–$C_{20}$alkyl optionally interrupted by one or more —O— and/or optionally substituted by one or more hydroxyl groups; or R₁ is $C_2$–$C_{20}$alkanoyl; or is benzoyl which is unsubstituted or substituted by one or more $C_1$–$C_6$alkyl, phenyl, $OR_8$, $SR_9$ or $NR_{10}R_{11}$; or R₁ is $C_2$–$C_{12}$alkoxycarbonyl optionally interrupted by one or more —O— and/or optionally substituted by one or more hydroxyl groups; or R₁ is phenoxycarbonyl which is unsubstituted or substituted by $C_1$–$C_6$alkyl, halogen, phenyl, $OR_8$ or $NR_{10}R_{11}$; or R₁ is —$CONR_{10}R_{11}$, CN, $NO_2$, $C_1$–$C_4$haloalkyl, $S(O)_mC_1$–$C_6$alkyl; unsubstituted or $C_1$–$C_{12}$alkyl-substituted $S(O)_m$—$C_6$–$C_{12}$aryl; $SO_2O$—$C_1$–$C_6$alkyl, $SO_2O$—$C_6$–$C_{10}$aryl, or diphenyl-phosphinoyl;
m is 1 or 2;

R₁' is $C_2$–$C_{12}$alkoxycarbonyl optionally interrupted by one or more —O— and/or optionally substituted by one or more hydroxyl groups; or R₁' is phenoxycarbonyl which is unsubstituted or substituted by one or more $C_1$–$C_6$alkyl, halogen, phenyl, $OR_8$ or $NR_{10}R_{11}$; or R₁' is $C_5$–$C_8$cycloalkyl, —$CONR_{10}R_{11}$, CN; or phenyl which is substituted by $SR_9$, wherein optionally a 5- or 6-membered ring is formed via the group $R_9$ by building a link to a carbon atom of the phenyl ring bearing the groups $R_4'$, $R_5'$ and $R_6'$; or, if at least one of $R_4'$, $R_5'$ or $R_6'$ is —$SR_9$ $R_1'$ additionally is $C_1$–$C_{12}$alkyl which is unsubstituted or substituted by one or more halogen, OH, $OR_2$, phenyl, halogenated phenyl or phenyl substituted by $SR_9$, and which $C_1$–$C_{12}$alkyl optionally is interrupted by —O— or —NH—(CO)—;

R₂ is $C_2$–$C_{12}$alkanoyl which is unsubstituted or substituted by one or more halogen or CN; or R₂ is $C_4$–$C_6$alkenoyl, provided that the double bond is not conjugated with the carbonyl group; or R₂ is benzoyl which is unsubstituted or substituted by one or more $C_1$–$C_6$alkyl, halogen CN, $OR_8$, $SR_9$ or $NR_{10}R_{11}$; or R₂ is $C_2$–$C_6$alkoxycarbonyl; or phenoxycarbonyl which is unsubstituted or substituted by $C_1$–$C_6$alkyl or halogen;

$R_3$, $R_4$, $R_5$, $R_6$ and $R_7$ independently of one another are hydrogen, halogen, $C_1$–$C_{12}$alkyl, cyclopentyl, cyclohexyl; or phenyl which is unsubstituted or substituted by one or more $OR_8$, $SR_9$ or $NR_{10}R_{11}$; or $R_3$, $R_4$, $R_5$, $R_6$ and $R_7$ are benzyl, benzoyl, $C_2$–$C_{12}$alkanoyl; $C_2$–$C_{12}$alkoxycarbonyl optionally interrupted by one or more —O— and/or optionally substituted by one or more hydroxyl groups; or $R_3$, $R_4$, $R_5$, $R_6$ and $R_7$ are phenoxycarbonyl; $OR_8$, $SR_9$, $SOR_9$, $SO_2R_9$ or $NR_{10}R_{11}$, wherein the substituents $OR_8$, $SR_9$ and $NR_{10}R_{11}$ optionally form 5- or 6-membered rings via the radicals $R_8$, $R_9$, $R_{10}$ and/or $R_{11}$ with further substituents on the phenyl ring or with one of the carbon atoms of the phenyl ring;

provided that at least one of the groups $R_3$, $R_4$, $R_5$, $R_6$ or $R_7$ is $SR_9$ or $NR_{10}R_{11}$;

$R_4'$, $R_5'$ and $R_6'$ independently of one another are hydrogen, halogen, $C_1$–$C_{12}$alkyl, cyclopentyl, cyclohexyl; phenyl which is unsubstituted or substituted by $OR_8$, $SR_9$ or $NR_{10}R_{11}$; or $R_4'$, $R_5'$ and $R_6'$ are benzyl, benzoyl, $C_2$–$C_{12}$alkanoyl; $C_2$–$C_{12}$alkoxycarbonyl optionally interrupted by one or more —O— and/or optionally substituted by one or more hydroxyl groups; or $R_4'$, $R_5'$ and $R_6'$ are phenoxycarbonyl; $OR_8$, $SR_9$, $SOR_9$, $SO_2R_9$, $NR_{10}R_{11}$, wherein the substituents $OR_8$, $SR_9$ and $NR_{10}R_{11}$ optionally form 5- or 6-membered rings via the radicals $R_8$, $R_9$, $R_{10}$ and/or $R_{11}$ with further substituents on the phenyl ring or with one of the carbon atoms of the phenyl ring;

provided that at least one of $R'_4$, $R'_5$ and $R'_6$ is $SR_9$ or $NR_{10}R_{11}$, $R_8$ is hydrogen, $C_1$–$C_{12}$alkyl; or $C_2$–$C_6$alkyl which is substituted by —OH, —SH, —CN, $C_1$–$C_4$alkoxy, $C_3$–$C_6$alkenoxy, —$OCH_2CH_2CN$, —$OCH_2CH_2$(CO)O($C_1$–$C_4$alkyl), —O(CO)—$C_1$–$C_4$alkyl, —O(CO)-phenyl, —(CO)OH or —(CO)O ($C_1$–$C_4$alkyl); or $R_8$ is $C_2$–$C_6$alkyl which is interrupted by one or more —O—; or $R_8$ is —$(CH_2CH_2O)_nH$, $C_2$–$C_8$alkanoyl, $C_3$–$C_{12}$alkenyl, $C_3$–$C_6$alkenoyl, cyclohexyl; or is phenyl which is unsubstituted or substituted by halogen, $C_1$–$C_{12}$alkyl or $C_1$–$C_4$alkoxy; or $R_8$ is phenyl-$C_1$–$C_3$alkyl, $Si(C_1$–$C_8$alkyl)$_r$(phenyl)$_{3-r}$, or a group

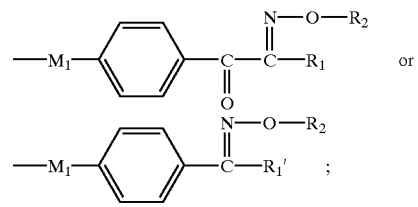

n is 1–20;
r is 1, 2 or 3;
$R_9$ is hydrogen, $C_1$–$C_{12}$alkyl, $C_3$–$C_{12}$alkenyl, cyclohexyl; $C_2$–$C_6$ alkyl which is substituted by —OH, —SH, —CN, $C_1$–$C_4$alkoxy, $C_3$–$C_6$alkenoxy, —$OCH_2CH_2CN$, —$OCH_2CH_2$(CO)O($C_1$–$C_4$alkyl), —O(CO)—$C_1$–$C_4$alkyl, —O(CO)-phenyl, —(CO)OH or —(CO)O($C_1$–$C_4$alkyl); or $R_9$ is $C_2$–$C_{12}$alkyl which is interrupted by one or more —O— or —S—; or $R_9$ is phenyl which is unsubstituted or substituted by halogen, $C_1$–$C_{12}$alkyl or $C_1$–$C_4$alkoxy; or $R_9$ is phenyl-$C_1$–$C_3$alkyl or a group

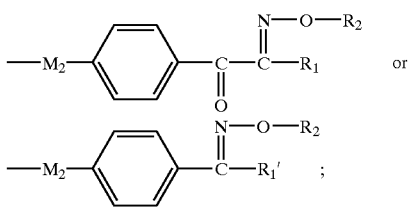

$R_{10}$ and $R_{11}$ independently of each other are hydrogen, $C_1$–$C_{12}$alkyl, $C_2$–$C_4$hydroxyalkyl, $C_2$–$C_{10}$alkoxyalkyl, $C_3$–$C_5$alkenyl, $C_5$–$C_{12}$cycloalkyl, phenyl-$C_1$–$C_3$alkyl; phenyl which is unsubstituted or substituted by $C_1$–$C_{12}$alkyl or $C_1$–$C_4$alkoxy; or $R_{10}$ and $R_{11}$, are $C_2$–$C_3$alkanoyl, $C_3$–$C_6$alkenoyl or benzoyl. or $R_{10}$ and $R_{11}$ together are $C_2$–$C_6$alkylene optionally interrupted by —O— or —$NR_8$—, and/or optionally substituted by hydroxyl, $C_1$–$C_4$alkoxy, $C_2$–$C_4$alkanoyloxy or benzoyloxy; or, when $R_{10}$ is hydrogen, $R_{11}$ may be a group of formula

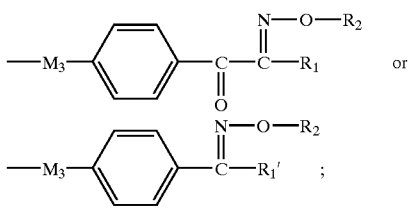

M is $C_1$–$C_{12}$alkylene, cyclohexylene, phenylene, —(CO)O—($C_2$–$C_{12}$alkylene)—O(CO)—, —(CO)O—($CH_2CH_2O$)$_n$—(CO)— or —(CO)—($C_2$–$C_{12}$alkylene)-(CO)—;

$M_1$ is a direct bond; or $C_1$–$C_{12}$alkyleneoxy-, optionally interrupted by 1 to 5 —O—, —S— and/or —$NR_{10}$—;

$M_2$ is a direct bond; or $C_1$–$C_{12}$alkylene-S—, optionally interrupted by 1 to 5 —O—, —S— and/or —$NR_{10}$—;

$M_3$ is a direct bond, a piperazino group; or $C_1$–$C_{12}$alkylene-NH—, optionally interrupted by 1 to 5 —O—, —S— and/or —$NR_{10}$—;

provided that
(i) if $R_5$ is methoxy and $R_2$ is benzoyl or acetyl, then $R_1$ is not phenyl;
(ii) if $R_5$ is methoxy and $R_1$ is ethoxycarbonyl, then $R_2$ is not benzoyl or ethoxycarbonyl;
(iii) if $R_5$ is methoxy and $R_1$ is 4-methoxybenzoyl, then $R_2$ is not ethoxycarbonyl;
(iv) if $R_5$ is methacryloylamino and $R_1$ is methyl, then $R_2$ is not benzoyl;
(v) if both, $R_5$ and $R_4$ or $R_5$ and $R_6$, are $OR_8$ and these $OR_8$ groups together form a ring via $R_8$ and thereby give —O—$CH_2$—, and $R_1$ is methyl, then $R_2$ is not acetyl;
(vi) if $R_4$, $R_5$ and $R_6$ simultaneously are methoxy and $R_1$ is ethoxycarbonyl, then $R_2$ is not acetyl.

9. A photopolymerizable composition according to claim 8, comprising in addition to the photoinitiator (b) at least one further photoinitiator (c) and/or other additives (d).

10. A photopolymerizable composition according to claim 9, comprising 0.05 to 20% by weight of the photoinitiator (b), or the photoinitiators (b) and (c), based on the composition.

11. A photopolymerizable composition according to claim 9 as further additive (d) comprising a photosensitizer a compound selection from the group consisting of benzophenone and its derivatives, thioxanthone and its derivatives, anthraquinone and its derivatives and coumarin and its derivatives.

12. A process for the photopolymerization of compounds containing ethylenically unsaturated double bonds, which comprises irradiating a composition according to claim 8 with electromagnetic radiation in the range from 190 to 600 nm, with electron beam or with X-rays.

13. A process according to claim 12 for producing pigmented and non-pigmented paints and varnishes, powder coatings, printing inks, printing plates, adhesives, dental compositions, composite compositions, resists, including photoresists, color filter materials, compositions for encapsulating electrical and electronic components, for producing magnetic recording materials, micromechanical parts, waveguides, optical switches, plating masks, etch masks, colour proofing systems, glass fibre cable coatings, screen printing stencils, for producing three-dimensional objects by means of microlithography, plating, stereolithography, for producing image recording materials, microelectronic circuits, decolorizing materials, decolorizing materials for image recording materials, for image recording materials using microcapsules.

14. Coated substrate which is coated on at least one surface with a composition according to claim 8.

15. Process for the photographic production of relief images, in which a coated substrate according to claim 14 is subjected to imagewise exposure and then the unexposed portions are removed with a developer.

16. A photopolymerizable composition according to claim 8, comprising 0.05 to 20% by weight of the photoinitiator (b) based on the composition.

17. A photopolymerizable composition according to claim 8 additionally comprising a binder polymer (e).

18. A photopolymerizable composition according to claim 17 wherein the binder polymer (e) is a copolymer of methacrylate and methacrylic acid.

* * * * *